United States Patent
Misener et al.

(10) Patent No.: US 12,349,984 B2
(45) Date of Patent: Jul. 8, 2025

(54) SYSTEM, METHOD, AND APPARATUS FOR IMPROVED CONFIRM OF AN ANATOMICAL POSITION OF A MEDICAL INSTRUMENT

(71) Applicant: Bard Access Systems, Inc., Salt Lake City, UT (US)

(72) Inventors: Anthony K. Misener, Bountiful, UT (US); Steffan Sowards, Salt Lake City, UT (US); William Robert McLaughlin, Bountiful, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 312 days.

(21) Appl. No.: 17/853,590

(22) Filed: Jun. 29, 2022

(65) Prior Publication Data

US 2024/0000515 A1   Jan. 4, 2024

(51) Int. Cl.
*A61B 5/05* (2021.01)
*A61B 5/0205* (2006.01)
(Continued)

(52) U.S. Cl.
CPC .......... *A61B 34/20* (2016.02); *A61B 5/02055* (2013.01); *A61B 5/026* (2013.01); *A61B 5/318* (2021.01); *A61B 2034/2055* (2016.02)

(58) Field of Classification Search
CPC ......... A61B 34/20; A61B 5/318; A61B 5/026; A61B 5/02055
See application file for complete search history.

(56) References Cited

U.S. PATENT DOCUMENTS

| 4,813,429 A | 3/1989 | Eshel et al. |
| 5,099,845 A | 3/1992 | Besz et al. |

(Continued)

FOREIGN PATENT DOCUMENTS

| CN | 101132730 A | 2/2008 |
| CN | 111265309 A | 6/2020 |

(Continued)

OTHER PUBLICATIONS

PCT/US2018/026493 filed Apr. 6, 2018 International Search Report and Written Opinion dated Jun. 22, 2018.

(Continued)

*Primary Examiner* — Joel F Brutus
(74) *Attorney, Agent, or Firm* — Rutan & Tucker LLP

(57) ABSTRACT

Disclosed herein is a system, apparatus and method directed to obtaining first data indicative of a first location within the patient vasculature, obtaining second data that is indicative of a second location within the patient vasculature, performing a confirmation process that includes determining whether the second location corresponds to the first location within a predetermined threshold, and when the second location is determined to correspond to the first location within the predetermined threshold, determining the first location accurately indicates the current location of the distal tip of the medical device. The first modality may be any of a fiber optic modality, a magnetically-based tip location system modality, or an electrocardiogram monitoring system modality and the second data may represent fluctuations of the distal tip of the medical device. The medical device may be an introducer wire, a guidewire, a stylet, a stylet within a needle, a needle, or a catheter.

24 Claims, 17 Drawing Sheets

(51) Int. Cl.
  *A61B 5/026* (2006.01)
  *A61B 5/318* (2021.01)
  *A61B 34/20* (2016.01)

(56) References Cited

U.S. PATENT DOCUMENTS

| | | | |
|---|---|---|---|
| 5,163,935 A | 11/1992 | Black et al. |
| 5,207,672 A | 5/1993 | Roth et al. |
| 5,211,165 A | 5/1993 | Dumoulin et al. |
| 5,275,151 A | 1/1994 | Shockey et al. |
| 5,280,786 A | 1/1994 | Wlodarczyk et al. |
| 5,423,321 A | 6/1995 | Fontenot |
| 5,454,807 A | 10/1995 | Lennox et al. |
| 5,460,182 A | 10/1995 | Goodman et al. |
| 5,517,997 A | 5/1996 | Fontenot |
| 5,622,170 A | 4/1997 | Schulz |
| 5,740,808 A | 4/1998 | Panescu et al. |
| 5,841,131 A | 11/1998 | Schroeder et al. |
| 5,872,879 A | 2/1999 | Hamm |
| 5,873,842 A | 2/1999 | Brennen et al. |
| 5,879,306 A | 3/1999 | Fontenot et al. |
| 5,906,579 A | 5/1999 | Vander Salm et al. |
| 6,069,698 A | 5/2000 | Ozawa et al. |
| 6,081,741 A | 6/2000 | Hollis |
| 6,178,346 B1 | 1/2001 | Amundson et al. |
| 6,208,887 B1 | 3/2001 | Clarke |
| 6,319,227 B1 | 11/2001 | Mansouri-Ruiz |
| 6,343,227 B1 | 1/2002 | Crowley |
| 6,398,721 B1 | 6/2002 | Nakamura et al. |
| 6,485,482 B1 | 11/2002 | Belef |
| 6,564,089 B2 | 5/2003 | Izatt et al. |
| 6,593,884 B1 | 7/2003 | Gilboa et al. |
| 6,597,941 B2 | 7/2003 | Fontenot et al. |
| 6,650,923 B1 | 11/2003 | Lesh et al. |
| 6,673,214 B1 | 1/2004 | Marchitto et al. |
| 6,685,666 B1 | 2/2004 | Fontenot |
| 6,687,010 B1 | 2/2004 | Horii et al. |
| 6,690,966 B1 | 2/2004 | Rava et al. |
| 6,701,181 B2 | 3/2004 | Tang et al. |
| 6,711,426 B2 | 3/2004 | Benaron et al. |
| 6,816,743 B2 | 11/2004 | Moreno et al. |
| 6,892,090 B2 | 5/2005 | Verard et al. |
| 6,895,267 B2 | 5/2005 | Panescu et al. |
| 7,132,645 B2 | 11/2006 | Kom |
| 7,273,056 B2 | 9/2007 | Wilson et al. |
| 7,344,533 B2 | 3/2008 | Pearson et al. |
| 7,366,562 B2 | 4/2008 | Dukesherer et al. |
| 7,366,563 B2 | 4/2008 | Kleen et al. |
| 7,396,354 B2 | 7/2008 | Rychnovsky et al. |
| 7,406,346 B2 | 7/2008 | Kleen et al. |
| 7,515,265 B2 | 4/2009 | Alfano et al. |
| 7,532,920 B1 | 5/2009 | Ainsworth et al. |
| 7,587,236 B2 | 9/2009 | Demos et al. |
| 7,603,166 B2 | 10/2009 | Casscells, III et al. |
| 7,729,735 B1 | 6/2010 | Burchman |
| 7,757,695 B2 | 7/2010 | Wilson et al. |
| 7,758,499 B2 | 7/2010 | Adler |
| 7,840,253 B2 | 11/2010 | Tremblay et al. |
| 7,992,573 B2 | 8/2011 | Wilson et al. |
| 8,032,200 B2 | 10/2011 | Tearney et al. |
| 8,054,469 B2 | 11/2011 | Nakabayashi et al. |
| 8,060,187 B2 | 11/2011 | Marshik-Geurts et al. |
| 8,073,517 B1 | 12/2011 | Burchman |
| 8,078,261 B2 | 12/2011 | Imam |
| 8,187,189 B2 | 5/2012 | Jung et al. |
| 8,267,932 B2 | 9/2012 | Baxter et al. |
| 8,369,932 B2 | 2/2013 | Cinbis et al. |
| 8,388,541 B2 | 3/2013 | Messerly et al. |
| 8,571,640 B2 | 10/2013 | Holman |
| 8,597,315 B2 | 12/2013 | Snow et al. |
| 8,700,358 B1 | 4/2014 | Parker, Jr. |
| 8,781,555 B2 | 7/2014 | Burnside et al. |
| 8,798,721 B2 | 8/2014 | Dib |
| 8,968,331 B1 | 3/2015 | Sochor |
| 8,979,871 B2 | 3/2015 | Tyc et al. |
| 9,060,687 B2 | 6/2015 | Yamanaka et al. |
| 9,114,226 B1 | 8/2015 | Lash et al. |
| 9,206,309 B2 | 12/2015 | Appleby et al. |
| 9,360,630 B2 | 6/2016 | Jenner et al. |
| 9,504,392 B2 | 11/2016 | Caron et al. |
| 9,560,954 B2 | 2/2017 | Jacobs et al. |
| 9,622,706 B2 | 4/2017 | Dick et al. |
| 9,678,275 B1 | 6/2017 | Griffin |
| 10,231,753 B2 | 3/2019 | Burnside et al. |
| 10,258,240 B1 | 4/2019 | Eberle et al. |
| 10,327,830 B2 | 6/2019 | Grant et al. |
| 10,349,890 B2 | 7/2019 | Misener et al. |
| 10,492,876 B2 | 12/2019 | Anastassiou et al. |
| 10,568,586 B2 | 2/2020 | Begin et al. |
| 10,631,718 B2 | 4/2020 | Petroff et al. |
| 10,992,078 B2 | 4/2021 | Thompson et al. |
| 11,123,047 B2 | 9/2021 | Jaffer et al. |
| 11,525,670 B2 | 12/2022 | Messerly et al. |
| 2001/0014793 A1 | 8/2001 | Brugger et al. |
| 2002/0198457 A1 | 12/2002 | Tearney et al. |
| 2003/0092995 A1 | 5/2003 | Thompson |
| 2004/0129555 A1 | 7/2004 | Marchitto et al. |
| 2004/0161362 A1 | 8/2004 | Bogert |
| 2004/0242995 A1 | 12/2004 | Maschke |
| 2005/0033264 A1 | 2/2005 | Redinger |
| 2005/0163424 A1 | 7/2005 | Chen |
| 2005/0261598 A1 | 11/2005 | Banet et al. |
| 2005/0278010 A1 | 12/2005 | Richardson |
| 2006/0013523 A1 | 1/2006 | Childlers et al. |
| 2006/0015136 A1 | 1/2006 | Besselink |
| 2006/0036164 A1 | 2/2006 | Wilson et al. |
| 2006/0189959 A1 | 8/2006 | Schneiter |
| 2006/0200049 A1 | 9/2006 | Leo et al. |
| 2006/0241395 A1 | 10/2006 | Kruger et al. |
| 2006/0241492 A1 | 10/2006 | Boese et al. |
| 2007/0156019 A1 | 7/2007 | Larkin et al. |
| 2007/0201793 A1 | 8/2007 | Askins et al. |
| 2007/0287886 A1 | 12/2007 | Saadat |
| 2007/0287934 A1 | 12/2007 | Babaev |
| 2007/0299425 A1 | 12/2007 | Waner et al. |
| 2008/0039715 A1 | 2/2008 | Wilson et al. |
| 2008/0077225 A1 | 3/2008 | Carlin et al. |
| 2008/0082004 A1 | 4/2008 | Banet et al. |
| 2008/0172119 A1 | 7/2008 | Yamasaki et al. |
| 2008/0183128 A1 | 7/2008 | Morriss et al. |
| 2008/0212082 A1 | 9/2008 | Froggatt et al. |
| 2008/0285909 A1 | 11/2008 | Younge et al. |
| 2008/0319290 A1 | 12/2008 | Mao et al. |
| 2009/0054908 A1 | 2/2009 | Zand et al. |
| 2009/0062634 A1 | 3/2009 | Say et al. |
| 2009/0118612 A1 | 5/2009 | Grunwald et al. |
| 2009/0137952 A1 | 5/2009 | Ramamurthy et al. |
| 2009/0234328 A1 | 9/2009 | Cox et al. |
| 2009/0304582 A1 | 12/2009 | Rousso et al. |
| 2009/0314925 A1 | 12/2009 | Van Vorhis et al. |
| 2010/0016729 A1 | 1/2010 | Futrell |
| 2010/0030063 A1 | 2/2010 | Lee et al. |
| 2010/0030132 A1 | 2/2010 | Niezgoda et al. |
| 2010/0063534 A1 | 3/2010 | Kugler et al. |
| 2010/0114115 A1 | 5/2010 | Schlesinger et al. |
| 2010/0286531 A1 | 11/2010 | Ryan et al. |
| 2010/0312095 A1 | 12/2010 | Jenkins et al. |
| 2011/0060229 A1 | 3/2011 | Hulvershorn et al. |
| 2011/0090486 A1 | 4/2011 | Udd |
| 2011/0144481 A1 | 6/2011 | Feer et al. |
| 2011/0166442 A1 | 7/2011 | Sarvazyan |
| 2011/0172591 A1 | 7/2011 | Babaev |
| 2011/0172680 A1 | 7/2011 | Younge et al. |
| 2011/0237958 A1 | 9/2011 | Onimura |
| 2011/0242532 A1 | 10/2011 | McKenna |
| 2011/0245662 A1 | 10/2011 | Eggers et al. |
| 2011/0288405 A1 | 11/2011 | Razavi et al. |
| 2011/0295108 A1 | 12/2011 | Cox et al. |
| 2011/0313280 A1 | 12/2011 | Govari et al. |
| 2012/0046562 A1 | 2/2012 | Powers et al. |
| 2012/0065481 A1 | 3/2012 | Hunter et al. |
| 2012/0101413 A1 | 4/2012 | Beetel et al. |
| 2012/0136242 A1 | 5/2012 | Qi et al. |
| 2012/0143029 A1 | 6/2012 | Silverstein et al. |

(56) References Cited

U.S. PATENT DOCUMENTS

| | | |
|---|---|---|
| 2012/0184827 A1 | 7/2012 | Shwartz et al. |
| 2012/0184955 A1 | 7/2012 | Pivotto et al. |
| 2012/0283747 A1 | 11/2012 | Popovic |
| 2012/0289783 A1 | 11/2012 | Duindam et al. |
| 2012/0321243 A1 | 12/2012 | Younge et al. |
| 2013/0028554 A1 | 1/2013 | Wong et al. |
| 2013/0072943 A1 | 3/2013 | Parmar |
| 2013/0096482 A1 | 4/2013 | Bertrand et al. |
| 2013/0104884 A1 | 5/2013 | Vazales et al. |
| 2013/0188855 A1 | 7/2013 | Desjardins et al. |
| 2013/0204124 A1 | 8/2013 | Duindam et al. |
| 2013/0211246 A1 | 8/2013 | Parasher |
| 2013/0296693 A1 | 11/2013 | Wenzel et al. |
| 2013/0310668 A1 | 11/2013 | Young |
| 2013/0317372 A1 | 11/2013 | Eberle et al. |
| 2013/0324840 A1 | 12/2013 | Zhongping et al. |
| 2014/0121468 A1 | 5/2014 | Eichenholz |
| 2014/0221829 A1 | 8/2014 | Maitland et al. |
| 2014/0275997 A1 | 9/2014 | Chopra et al. |
| 2015/0029511 A1 | 1/2015 | 'T Hooft et al. |
| 2015/0031987 A1 | 1/2015 | Pameijer et al. |
| 2015/0080688 A1 | 3/2015 | Cinbis et al. |
| 2015/0099979 A1 | 4/2015 | Caves et al. |
| 2015/0119700 A1 | 4/2015 | Liang et al. |
| 2015/0124264 A1 | 5/2015 | Ramachandran et al. |
| 2015/0141854 A1 | 5/2015 | Eberle et al. |
| 2015/0164571 A1 | 6/2015 | Saadat |
| 2015/0190221 A1 | 7/2015 | Schaefer et al. |
| 2015/0209113 A1 | 7/2015 | Burkholz et al. |
| 2015/0209117 A1 | 7/2015 | Flexman et al. |
| 2015/0254526 A1 | 9/2015 | Denissen |
| 2015/0320977 A1 | 11/2015 | Vitullo et al. |
| 2016/0018602 A1 | 1/2016 | Govari et al. |
| 2016/0067449 A1 | 3/2016 | Misener et al. |
| 2016/0102969 A1 | 4/2016 | Verstege et al. |
| 2016/0166326 A1 | 6/2016 | Bakker et al. |
| 2016/0166341 A1 | 6/2016 | Iordachita et al. |
| 2016/0184020 A1 | 6/2016 | Kowalewski et al. |
| 2016/0213432 A1 | 7/2016 | Flexman et al. |
| 2016/0331461 A1 | 11/2016 | Cheatham, III et al. |
| 2016/0349044 A1 | 12/2016 | Marell et al. |
| 2016/0354038 A1 | 12/2016 | Demirtas et al. |
| 2017/0020394 A1 | 1/2017 | Harrington |
| 2017/0079681 A1 | 3/2017 | Burnside et al. |
| 2017/0082806 A1 | 3/2017 | Van Der Mark et al. |
| 2017/0151027 A1 | 6/2017 | Walker et al. |
| 2017/0173349 A1 | 6/2017 | Pfleiderer et al. |
| 2017/0196479 A1 | 7/2017 | Liu et al. |
| 2017/0201036 A1 | 7/2017 | Cohen et al. |
| 2017/0215973 A1 | 8/2017 | Flexman et al. |
| 2017/0231699 A1 | 8/2017 | Flexman et al. |
| 2017/0273542 A1 | 9/2017 | Au |
| 2017/0273565 A1 | 9/2017 | Ma et al. |
| 2017/0273628 A1 | 9/2017 | Ofek et al. |
| 2017/0290563 A1 | 10/2017 | Cole et al. |
| 2017/0311901 A1 | 11/2017 | Zhao et al. |
| 2017/0319279 A1 | 11/2017 | Fish et al. |
| 2018/0008443 A1 | 1/2018 | Cole et al. |
| 2018/0031493 A1 | 2/2018 | Tojo et al. |
| 2018/0095231 A1 | 4/2018 | Lowell et al. |
| 2018/0113038 A1 | 4/2018 | Janabi-Sharifi et al. |
| 2018/0116551 A1* | 5/2018 | Newman .............. A61B 8/0841 |
| 2018/0140170 A1 | 5/2018 | Van Putten et al. |
| 2018/0235709 A1 | 8/2018 | Donhowe et al. |
| 2018/0239124 A1 | 8/2018 | Naruse et al. |
| 2018/0240237 A1 | 8/2018 | Donhowe et al. |
| 2018/0250088 A1 | 9/2018 | Brennan et al. |
| 2018/0264227 A1 | 9/2018 | Flexman et al. |
| 2018/0279909 A1 | 10/2018 | Noonan et al. |
| 2018/0289390 A1 | 10/2018 | Amorizzo et al. |
| 2018/0289927 A1* | 10/2018 | Messerly ................ G01L 1/242 |
| 2018/0339134 A1 | 11/2018 | Leo |
| 2018/0360545 A1 | 12/2018 | Cole et al. |
| 2019/0059743 A1 | 2/2019 | Ramachandran et al. |
| 2019/0110844 A1 | 4/2019 | Misener et al. |
| 2019/0231272 A1 | 8/2019 | Yamaji |
| 2019/0237902 A1 | 8/2019 | Thompson et al. |
| 2019/0247132 A1 | 8/2019 | Harks et al. |
| 2019/0307331 A1 | 10/2019 | Saadat et al. |
| 2019/0321110 A1 | 10/2019 | Grunwald et al. |
| 2019/0343424 A1 | 11/2019 | Blumenkranz et al. |
| 2019/0343702 A1 | 11/2019 | Smith |
| 2019/0357875 A1 | 11/2019 | Qi et al. |
| 2019/0365199 A1 | 12/2019 | Zhao et al. |
| 2019/0374130 A1 | 12/2019 | Bydlon et al. |
| 2020/0000526 A1 | 1/2020 | Zhao |
| 2020/0030575 A1 | 1/2020 | Bogusky et al. |
| 2020/0046434 A1 | 2/2020 | Graetzel et al. |
| 2020/0054399 A1 | 2/2020 | Duindam et al. |
| 2020/0121482 A1 | 4/2020 | Spector et al. |
| 2020/0188036 A1 | 6/2020 | Ding et al. |
| 2020/0297442 A1 | 9/2020 | Adebar et al. |
| 2020/0305983 A1 | 10/2020 | Yampolsky et al. |
| 2020/0315770 A1 | 10/2020 | Dupont et al. |
| 2020/0394789 A1 | 12/2020 | Freund et al. |
| 2021/0015470 A1 | 1/2021 | Prisco et al. |
| 2021/0023341 A1 | 1/2021 | Decheek et al. |
| 2021/0045814 A1 | 2/2021 | Thompson et al. |
| 2021/0068911 A1 | 3/2021 | Walker et al. |
| 2021/0298680 A1 | 3/2021 | Sowards et al. |
| 2021/0100627 A1 | 4/2021 | Soper et al. |
| 2021/0244311 A1 | 8/2021 | Zhao et al. |
| 2021/0268229 A1 | 9/2021 | Sowards et al. |
| 2021/0271035 A1 | 9/2021 | Sowards et al. |
| 2021/0275257 A1 | 9/2021 | Prior et al. |
| 2021/0330399 A1 | 10/2021 | Netravali et al. |
| 2021/0401456 A1 | 12/2021 | Cox et al. |
| 2021/0401509 A1 | 12/2021 | Misener et al. |
| 2021/0402144 A1 | 12/2021 | Messerly |
| 2022/0011192 A1 | 1/2022 | Misener et al. |
| 2022/0034733 A1 | 2/2022 | Misener et al. |
| 2022/0079683 A1 | 3/2022 | Bydlon et al. |
| 2022/0096796 A1 | 3/2022 | McLaughlin et al. |
| 2022/0110508 A1 | 4/2022 | Van Roosbroeck et al. |
| 2022/0110695 A1 | 4/2022 | Sowards et al. |
| 2022/0151568 A1 | 5/2022 | Yao et al. |
| 2022/0152349 A1 | 5/2022 | Sowards et al. |
| 2022/0160209 A1 | 5/2022 | Sowards et al. |
| 2022/0172354 A1 | 6/2022 | Misener et al. |
| 2022/0211442 A1 | 7/2022 | McLaughlin et al. |
| 2022/0233246 A1 | 7/2022 | Misener et al. |
| 2022/0369934 A1 | 11/2022 | Sowards et al. |
| 2023/0081198 A1 | 3/2023 | Sowards et al. |
| 2023/0097431 A1 | 3/2023 | Sowards et al. |
| 2023/0101030 A1 | 3/2023 | Misener et al. |
| 2023/0108604 A1 | 4/2023 | Messerly et al. |
| 2023/0126813 A1 | 4/2023 | Sowards et al. |
| 2023/0243715 A1 | 8/2023 | Misener et al. |
| 2023/0248444 A1 | 8/2023 | Misener et al. |
| 2023/0251150 A1 | 8/2023 | Misener et al. |
| 2023/0337985 A1 | 10/2023 | Sowards et al. |
| 2023/0346479 A1 | 11/2023 | Muller et al. |
| 2023/0414112 A1 | 12/2023 | Misener et al. |
| 2024/0050708 A1 | 2/2024 | Misener |
| 2024/0099659 A1 | 3/2024 | Sowards et al. |
| 2024/0108856 A1 | 4/2024 | Messerly |
| 2024/0216077 A1 | 7/2024 | Thompson et al. |
| 2024/0335237 A1 | 10/2024 | Sowards et al. |
| 2024/0353275 A1 | 10/2024 | Misener et al. |
| 2024/0383133 A1 | 11/2024 | Bydlon et al. |
| 2024/0390644 A1 | 11/2024 | McLaughlin et al. |
| 2025/0020453 A1 | 1/2025 | Thompson et al. |
| 2025/0060266 A1 | 2/2025 | Messerly |

FOREIGN PATENT DOCUMENTS

| | | |
|---|---|---|
| CN | 113080937 A | 7/2021 |
| DE | 102016109601 A1 | 11/2017 |
| EP | 2240111 A2 | 10/2010 |
| EP | 2907445 A1 | 8/2015 |
| EP | 3545849 A1 | 10/2019 |
| EP | 3705020 A1 | 9/2020 |
| JP | 7366562 B2 | 10/2023 |
| KR | 20190098512 A | 8/2019 |

(56) References Cited

FOREIGN PATENT DOCUMENTS

| | | | |
|---|---|---|---|
| WO | 99/64099 | A1 | 12/1999 |
| WO | 2006113394 | A2 | 10/2006 |
| WO | 2006122001 | A2 | 11/2006 |
| WO | 2007002323 | A2 | 1/2007 |
| WO | 2009/155325 | A2 | 12/2009 |
| WO | 2011121516 | A2 | 10/2011 |
| WO | 2011141830 | A1 | 11/2011 |
| WO | 2011150376 | A1 | 12/2011 |
| WO | 2012064769 | A2 | 5/2012 |
| WO | 2015044930 | A1 | 4/2015 |
| WO | 2015074045 | A2 | 5/2015 |
| WO | 2016038492 | A1 | 3/2016 |
| WO | 2016/061431 | A1 | 4/2016 |
| WO | 2016051302 | A1 | 4/2016 |
| WO | 2016149819 | A1 | 9/2016 |
| WO | 2018/096491 | A1 | 5/2018 |
| WO | 2019037071 | A1 | 2/2019 |
| WO | 2019/046769 | A1 | 3/2019 |
| WO | 2019070423 | A1 | 4/2019 |
| WO | 2019230713 | A1 | 12/2019 |
| WO | 2020/182997 | A1 | 9/2020 |
| WO | 2021030092 | A1 | 2/2021 |
| WO | 2021108688 | A1 | 6/2021 |
| WO | 2021108697 | A1 | 6/2021 |
| WO | 2021/138096 | A1 | 7/2021 |
| WO | 2021216089 | A1 | 10/2021 |
| WO | 2022/031613 | A1 | 2/2022 |
| WO | 2022/081723 | A1 | 4/2022 |
| WO | 2022150411 | A1 | 7/2022 |
| WO | 2022/164902 | A1 | 8/2022 |
| WO | 2022/245987 | A1 | 11/2022 |
| WO | 2023043954 | A1 | 3/2023 |
| WO | 2023049443 | A1 | 3/2023 |
| WO | 2023055810 | A1 | 4/2023 |
| WO | 2023076143 | A1 | 5/2023 |
| WO | 2023211752 | A1 | 11/2023 |
| WO | 2024006384 | A1 | 1/2024 |
| WO | 2024006441 | A1 | 1/2024 |
| WO | 2024064334 | A1 | 3/2024 |

OTHER PUBLICATIONS

PCT/US2020/044801 filed Aug. 3, 2020 International Search Report and Written Opinion dated Oct. 26, 2020.
PCT/US2020/062396 filed Nov. 25, 2020 International Preliminary Report on Patentability dated Jan. 29, 2021.
PCT/US2020/062396 filed Nov. 25, 2020 International Search Report and Written Opinion dated Mar. 2, 2021.
PCT/US2020/062407 filed Nov. 25, 2020 International Preliminary Report on Patentability dated Jan. 25, 2021.
PCT/US2020/062407 filed Nov. 25, 2020 International Search Report and Written Opinion dated Mar. 11, 2021.
PCT/US2021/038899 filed Jun. 24, 2021 International Search Report and Written Opinion dated Oct. 6, 2021.
PCT/US2021/038954 filed Jun. 24, 2021 International Search Report and Written Opinion dated Oct. 28, 2021.
PCT/US2021/041128 filed Jul. 9, 2021 International Search Report and Written Opinion dated Oct. 25, 2021.
PCT/US2021/044216 filed Aug. 2, 2021 International Search Report and Written Opinion dated Nov. 18, 2021.
PCT/US2021/054802 filed Oct. 13, 2021 International Search Report and Written Opinion dated Feb. 2, 2022.
PCT/US2022/011347 filed Jan. 5, 2022 International Search Report and Written Opinion dated May 3, 2022.
PCT/US2022/013897 filed Jan. 26, 2022 International Search Report and Written Opinion dated May 11, 2022.
U.S. Appl. No. 15/947,267, filed Apr. 6, 2018 Final Office Action dated Apr. 22, 2022.
U.S. Appl. No. 17/105,259, filed Nov. 25, 2020, Notice of Allowance dated Jul. 20, 2022.
U.S. Appl. No. 17/371,993, filed Jul. 9, 2021 Non-Final Office Action dated Jul. 12, 2022.
U.S. Appl. No. 15/947,267, filed Apr. 6, 2018 Final Office Action dated Jun. 30, 2021.
U.S. Appl. No. 15/947,267, filed Apr. 6, 2018 Final Office Action dated Nov. 10, 2020.
U.S. Appl. No. 15/947,267, filed Apr. 6, 2018 Non-Final Office Action dated Mar. 12, 2021.
U.S. Appl. No. 15/947,267, filed Apr. 6, 2018 Non-Final Office Action dated May 29, 2020.
U.S. Appl. No. 15/947,267, filed Apr. 6, 2018 Non-Final Office Action dated Oct. 13, 2021.
EP 20853352.1 filed Mar. 7, 2022 Extended European Search Report dated Jul. 27, 2023.
PCT/US2021/052046 filed Sep. 24, 2021 International Search Report and Written Opinion dated Jan. 11, 2022.
PCT/US2023/019239 filed Apr. 20, 2023 International Search Report and Written Opinion dated Jul. 20, 2023.
PCT/US2023/026487 filed Jun. 28, 2023 International Search Report and Written Opinion dated Sep. 6, 2023.
U.S. Appl. No. 16/984,104, filed Aug. 3, 2020 Final Office Action dated Sep. 21, 2023.
U.S. Appl. No. 16/984,104, filed Aug. 3, 2020 Non-Final Office Action dated Jun. 22, 2023.
U.S. Appl. No. 17/105,310, filed Nov. 25, 2020 Notice of Allowance dated Aug. 2, 2023.
U.S. Appl. No. 17/357,186, filed Jun. 24, 2021 Non Final Office Action dated May 30, 2023.
U.S. Appl. No. 17/357,186, filed Jun. 24, 2021 Notice of Allowance dated Aug. 23, 2023.
U.S. Appl. No. 17/484,960, filed Sep. 24, 2021 Non-Final Office Action dated Oct. 5, 2023.
U.S. Appl. No. 17/500,678, filed Oct. 13, 2021 Final Office Action dated Sep. 21, 2023.
Jackle Sonja et al. "Three-dimensional guidance including shape sensing of a stentgraft system for endovascular aneurysm repair." International Journal of Computer Assisted Radiology and Surgery, Springer DE. vol. 15, No. 6, May 7, 2020.
PCT/US2022/029894 filed May 18, 2022, International Search Report and Written Opinion dated Sep. 1, 2022.
PCT/US2022/043706 filed Sep. 16, 2022 International Search Report and Written Opinion dated Nov. 24, 2022.
PCT/US2022/044696 filed Sep. 26, 2022 International Search Report and Written Opinion dated Jan. 23, 2023.
PCT/US2022/045051 filed Sep. 28, 2022 International Search Report and Written Opinion dated Jan. 2, 2023.
PCT/US2022/047538 filed Oct. 24, 2022 International Search Report and Written Opinion dated Jan. 26, 2023.
U.S. Appl. No. 15/947,267, filed Apr. 6, 2018 Examiner's Answer dated Nov. 28, 2022.
U.S. Appl. No. 17/357,561, filed Jun. 24, 2021 Non-Final Office Action dated Aug. 11, 2022.
U.S. Appl. No. 17/357,561, filed Jun. 24, 2021 Notice of Allowance dated Dec. 9, 2022.
U.S. Appl. No. 17/371,993, filed Jul. 9, 2021 Notice of Allowance dated Nov. 3, 2022.
U.S. Appl. No. 17/392,002, filed Aug. 2, 2021, Non-Final Office Action dated Sep. 12, 2022.
U.S. Appl. No. 17/392,002, filed Aug. 2, 2021, Notice of Allowance dated Jan. 19, 2023.
U.S. Appl. No. 15/947,267, filed Apr. 6, 2018 Notice of Allowance dated Jul. 16, 2024.
U.S. Appl. No. 17/484,960, filed Sep. 24, 2021 Notice of Allowance dated Apr. 12, 2024.
U.S. Appl. No. 17/569,350, filed Jan. 5, 2022 Advisory Action dated Jul. 12, 2024.
U.S. Appl. No. 17/569,350, filed Jan. 5, 2022 Final Office Action dated Apr. 23, 2024.
U.S. Appl. No. 17/747,903, filed May 18, 2022 Restriction Requirement dated May 28, 2024.
U.S. Appl. No. 17/955,019, filed Sep. 28, 2022 Restriction Requirement dated Jun. 6, 2024.
U.S. Appl. No. 18/079,653, filed Dec. 12, 2022 Non-Final Office Action dated Feb. 6, 2024.

(56) References Cited

OTHER PUBLICATIONS

U.S. Appl. No. 18/079,653, filed Dec. 12, 2022 Notice of Allowance dated Jun. 4, 2024.
U.S. Appl. No. 18/132,231, filed Apr. 7, 2023 Non-Final Office Action dated Jul. 12, 2024.
U.S. Appl. No. 18/132,623, filed Apr. 10, 2023, Non-Final Office Action dated May 3, 2024.
U.S. Appl. No. 18/135,337, filed Apr. 17, 2023 Notice of Allowance dated Mar. 8, 2024.
U.S. Appl. No. 17/971,873, filed Oct. 24, 2022 Non-Final Office Action dated Jun. 6, 2024.
Fiber Optic RealShape (FORS) technology—research. Philips. (Oct. 18, 2018). Retrieved Feb. 28, 2023, from https:// www.philips.com/a-w/research/research-programs/fors.html (Year: 2018).
U.S. Appl. No. 16/984,104, filed Aug. 3, 2020 Restriction Requirement dated Mar. 13, 2023.
U.S. Appl. No. 17/105,310, filed Nov. 25, 2020 Non-Final Office Action dated Feb. 22, 2023.
U.S. Appl. No. 17/357,186, filed Jun. 24, 2021 Restriction Requirement dated Mar. 7, 2023.
U.S. Appl. No. 17/392,002, filed Aug. 2, 2021, Corrected Notice of Allowability dated Feb. 23, 2023.
U.S. Appl. No. 17/500,678, filed Oct. 13, 2021 Non-Final Office Action dated Mar. 15, 2023.
Dziuda L et al: "Monitoring Respiration and Cardiac Activity Using Fiber Bragg Grating-Based Sensor", IEEE Transactions on Biomedical Engineering vol. 59, No. 7, Jul. 2012 pp. 1934-1942.
Dziuda L et al: "Fiber-optic sensor for monitoring respiration and cardiac activity", 2011 IEEE Sensors Proceedings : Limerick, Ireland, Oct. 2011 pp. 413-416.
EP 20893677.3 filed Jun. 22, 2022 Extended European Search Report dated Oct. 13, 2023.
EP 20894633.5 filed Jun. 22, 2022 Extended European Search Report dated Oct. 16, 2023.
PCT/US2023/026581 filed Jun. 29, 2023 International Search Report and Written Opinion dated Oct. 27, 2023.
PCT/US2023/033471 filed Sep. 22, 2023 International Search Report and Written Opinion dated Dec. 21, 2023.
U.S. Appl. No. 16/984,104, filed Aug. 3, 2020 Notice of Allowance dated Nov. 21, 2023.
U.S. Appl. No. 17/500,678, filed Oct. 13, 2021 Advisory Action dated Dec. 7, 2023.
U.S. Appl. No. 17/500,678, filed Oct. 13, 2021 Non-Final Office Action dated Jan. 19, 2024.
U.S. Appl. No. 18/135,337, filed Apr. 17, 2023 Non-Final Office Action dated Dec. 22, 2023.
U.S. Appl. No. 17/569,350, filed Jan. 5, 2022 Non-Final Office Action dated Jan. 8, 2024.
Mayoral et al. Fiber Optic Sensors for Vital Signs Monitoring. A Review of Its Practicality in the Health Field. Biosensors (Basel). Feb. 23, 2021;11(2):58. doi: 10.3390/bios11020058.
P.J. de Feyter, P. Kay, C. Disco, P.W. Serruys, "Reference chart derived from post-stent-implantation intravascular ultrasound predictors of 6-month expected restenosis on quantitative coronary angiography." Circulation. vol. 100, No. 17 (Year: 1999).
PCT/US2023/026581 filed Jun. 29, 2023 International Preliminary Report on Patentability dated Dec. 18, 2024.
U.S. Appl. No. 17/500,678, filed Oct. 13, 2021 Advisory Action dated Nov. 6, 2024.
U.S. Appl. No. 17/500,678, filed Oct. 13, 2021 Final Office Action dated Aug. 27, 2024.
U.S. Appl. No. 17/500,678, filed Oct. 13, 2021 Non-Final Office Action dated Dec. 4, 2024.
U.S. Appl. No. 17/569,350, filed Jan. 5, 2022 Notice of Allowance dated Nov. 7, 2024.
U.S. Appl. No. 17/585,219, filed Jan. 26, 2022 Restriction Requirement dated Dec. 2, 2024.
U.S. Appl. No. 17/728,802, filed Apr. 25, 2022 Final Office Action dated Jan. 17, 2025.
U.S. Appl. No. 17/728,802, filed Apr. 25, 2022 Non-Final Office Action dated Aug. 28, 2024.
U.S. Appl. No. 17/747,903, filed May 18, 2022 Final Office Action dated Jan. 27, 2025.
U.S. Appl. No. 17/747,903, filed May 18, 2022 Non-Final Office Action dated Aug. 15, 2024.
U.S. Appl. No. 17/852,138, filed Jun. 28, 2022 Non-Final Office Action dated Sep. 18, 2024.
U.S. Appl. No. 17/955,019, filed Sep. 28, 2022 Final Office Action dated Feb. 4, 2025.
U.S. Appl. No. 17/955,019, filed Sep. 28, 2022 Non-Final Office Action dated Sep. 27, 2024.
U.S. Appl. No. 17/971,873, filed Oct. 24, 2022 Non-Final Office Action dated Dec. 27, 2024.
U.S. Appl. No. 18/132,231, filed Apr. 7, 2023 Final Office Action dated Jan. 31, 2025.
U.S. Appl. No. 18/132,623, filed Apr. 10, 2023, Final Office Action dated Sep. 6, 2024.
U.S. Appl. No. 18/132,623, filed Apr. 10, 2023, Notice of Allowance dated Nov. 19, 2024.
U.S. Appl. No. 18/383,809, filed Oct. 25, 2023 Non-Final Office Action dated Dec. 16, 2024.
U.S. Appl. No. 18/538,111, filed Dec. 13, 2023 Final Office Action dated Feb. 4, 2025.
U.S. Appl. No. 18/538,111, filed Dec. 13, 2023 Non-Final Office Action dated Aug. 9, 2024.
U.S. Appl. No. 18/607,144, filed Mar. 15, 2024 Non-Final Office Action dated Sep. 24, 2024.
U.S. Appl. No. 17/569,350, filed Jan. 5, 2022 Non-Final Office Action dated Aug. 12, 2024.
U.S. Appl. No. 17/585,219, filed Jan. 26, 2022 Non-Final Office Action dated Feb. 27, 2025.
U.S. Appl. No. 17/728,802, filed Apr. 25, 2022 Advisory Action dated Apr. 4, 2025.
U.S. Appl. No. 17/852,138 filed Jun. 28, 2022 Notice of Allowance dated Feb. 12, 2025.
U.S. Appl. No. 17/952,645, filed Sep. 26, 2022 Non-Final Office Action dated Feb. 28, 2025.
U.S. Appl. No. 18/132,231, filed Apr. 7, 2023 Notice of Allowance dated Apr. 10, 2025.
U.S. 18/607,144 filed Mar. 15, 2024 Final Office Action dated Feb. 19, 2025.

* cited by examiner

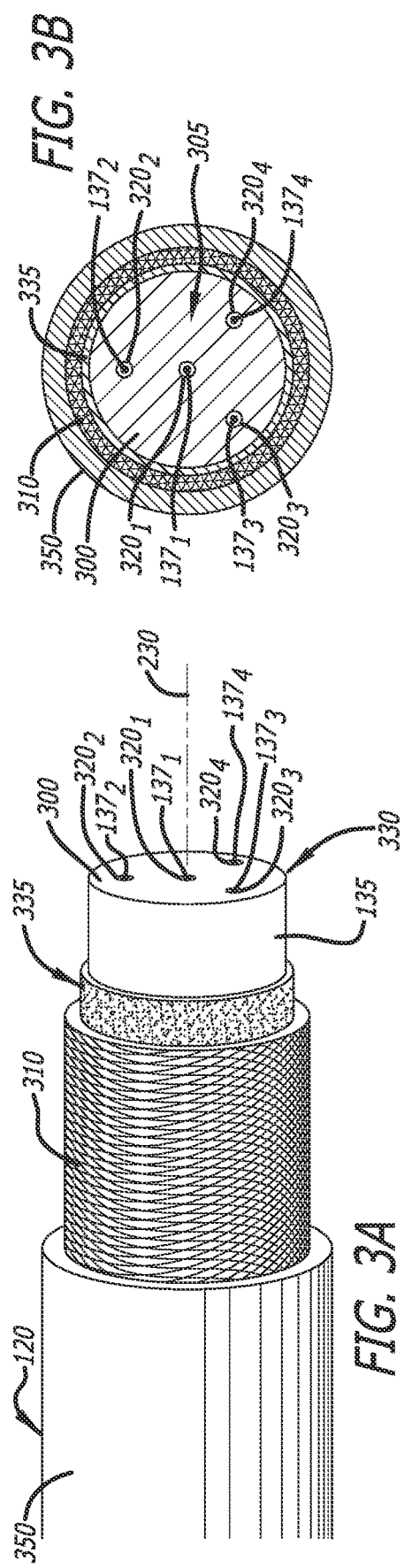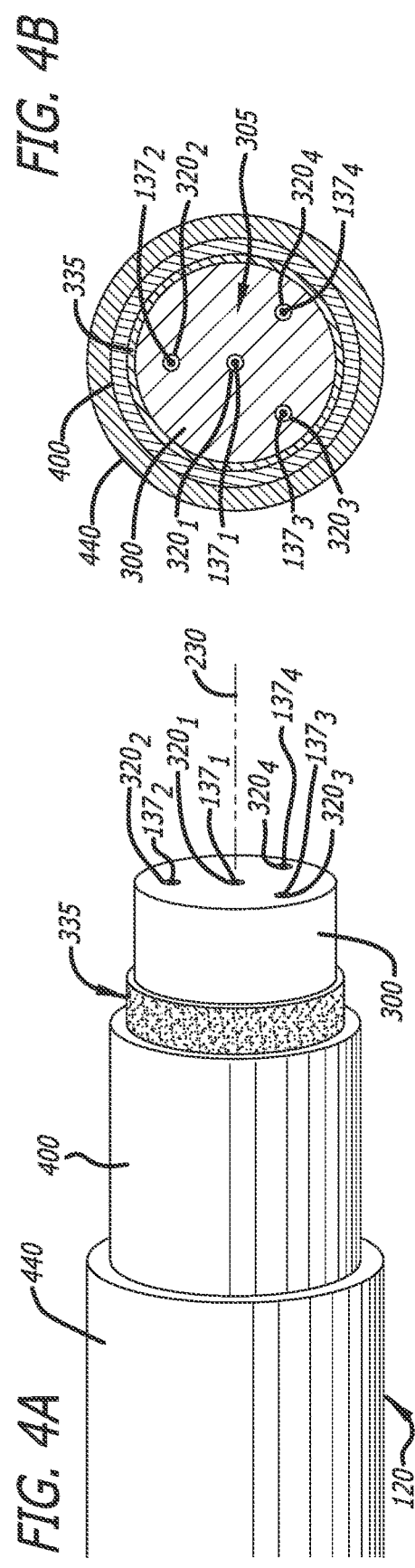

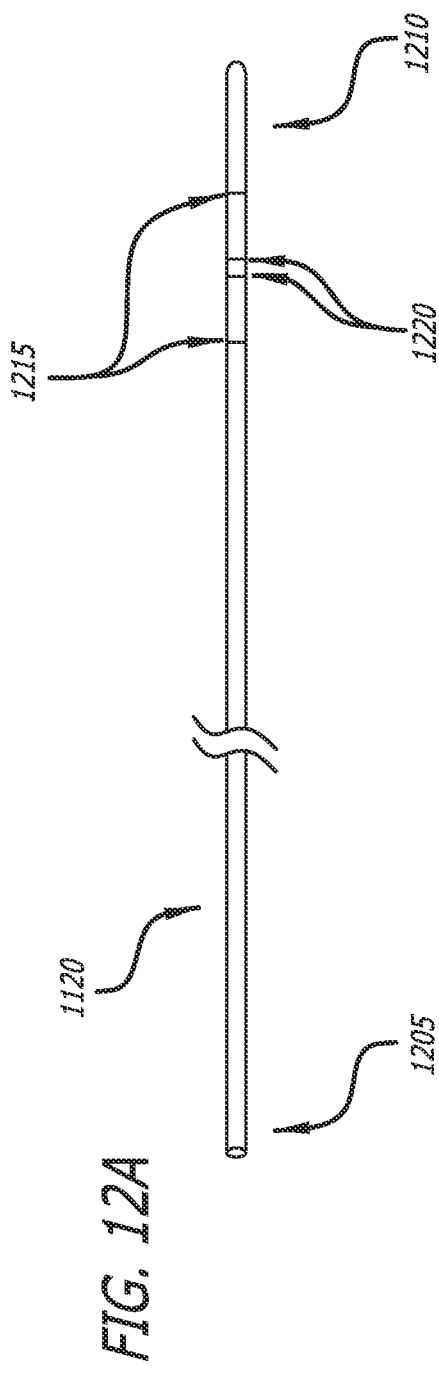
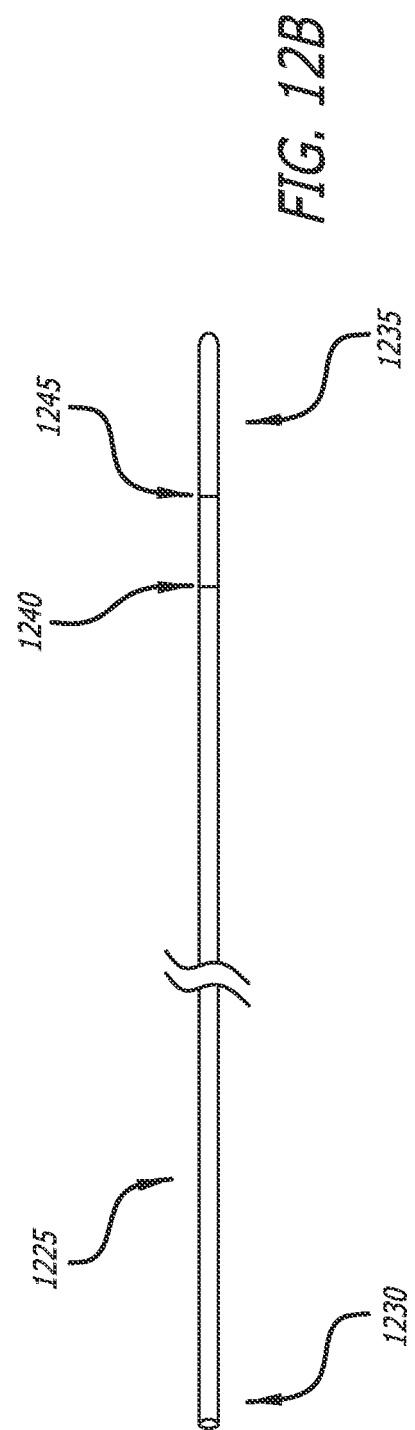

SYSTEM, METHOD, AND APPARATUS FOR IMPROVED CONFIRM OF AN ANATOMICAL POSITION OF A MEDICAL INSTRUMENT

BACKGROUND

In the past, certain intravascular guidance of medical devices, such as guidewires and catheters for example, have used fluoroscopic methods for tracking tips of the medical devices and determining whether distal tips are appropriately localized in their target anatomical structures. However, such fluoroscopic methods expose patients and their attending clinicians to harmful X-ray radiation. Moreover, in some cases, the patients are exposed to potentially harmful contrast media needed for the fluoroscopic methods.

More recently, electromagnetic tracking systems have been used involving stylets. Generally, electromagnetic tracking systems feature three components: a field generator, a sensor unit and control unit. The field generator uses several coils to generate a position-varying magnetic field, which is used to establish a coordinate space. Attached to the stylet, such as near a distal end (tip) of the stylet for example, the sensor unit includes small coils in which current is induced via the magnetic field. Based on the electrical properties of each coil, the position and orientation of the medical device may be determined within the coordinate space. The control unit controls the field generator and captures data from the sensor unit.

Although electromagnetic tracking systems avoid line-of-sight reliance in tracking the tip of a stylet while obviating radiation exposure and potentially harmful contrast media associated with fluoroscopic methods, electromagnetic tracking systems are prone to interference. More specifically, since electromagnetic tracking systems depend on the measurement of magnetic fields produced by the field generator, these systems are subject to electromagnetic field interference, which may be caused by the presence of many different types of consumer electronics such as cellular telephones. Additionally, electromagnetic tracking systems are subject to signal drop out, depend on an external sensor, and are defined to a limited depth range.

Disclosed herein is a system, apparatus and methods performed thereby where the system or apparatus is configured to obtain (e.g., receive, retrieve, measure, compute, etc.) first data indicative of a first location within a patient vasculature and second data indicative of a second location within the patient vasculature, where the first data is obtained through a first modality and the second data is obtained through a second modality. The system or apparatus is further configured to compare the first and second locations such that, when the two locations correspond or substantially correspond (e.g., are within a predetermined threshold distance from each other), determine that the first location accurately indicates a current position of a distal tip of a medical device within the patient vasculature.

SUMMARY

Briefly summarized, embodiments disclosed herein are directed to systems, apparatus and methods for obtaining measurements indicating fluctuations of a distal tip of a medical instrument (also referred to as a body of implementation), such as a catheter, a guidewire, or a stylet, via a fiber optic core during advancement through a vasculature of a patient. The systems, apparatus and methods may then further include correlation of the tip fluctuation measurements to stored data (e.g., experiential knowledge of previously measured tip fluctuations) in order to confirm a location of the distal tip of the medical device or detect a defect affecting a blood vessel. Although embodiments primarily discuss obtaining measurements indicating fluctuations of a distal tip of the medical device, the disclosure is not intended to be limited to such a particular portion of the medical device. Instead, the embodiments and methodologies described herein with respect to the distal tip may be applied to other portions of the medical device.

More particularly, in some embodiments, the medical instrument includes optical fiber core configured with an array of sensors (reflective gratings), which are spatially distributed over a prescribed length of the core fiber to generally sense external strain on those regions of the core fiber occupied by the sensor. The optical fiber core is configured to receive broadband light from a console during advancement through the vasculature of a patient, where the broadband light propagates along at least a partial distance of the optical fiber core toward the distal end. Given that each sensor positioned along the optical fiber core is configured to reflect light of a different, specific spectral width, the array of sensors enables distributed measurements throughout the prescribed length of the multi-core optical fiber. These distributed measurements may include wavelength shifts having a correlation with strain experienced by the sensor.

The reflected light from the sensors (reflective gratings) within the optical fiber core is returned from the medical instrument for processing by the console. The physical state of the medical instrument may be ascertained based on analytics of the wavelength shifts of the reflected light. For example, the strain caused through bending of the medical instrument, and hence angular modification of the optical fiber core, causes different degrees of deformation. The different degrees of deformation alter the shape of the sensors (reflective grating) positioned on the optical fiber core, which may cause variations (shifts) in the wavelength of the reflected light from the sensors positioned on the optical fiber core. The optical fiber core may comprise a single optical fiber, or a plurality of optical fibers (in which case, the optical fiber core is referred to as a "multi-core optical fiber").

As used herein, the term "core fiber," generally refers to a single optical fiber core disposed within a medical device. Thus, discussion of a core fiber refers to single optical fiber core and discussion of a multi-core optical fiber refers to a plurality of core fibers. Various embodiments discussed below to detection of the health (and particularly the damage) that occurs in each of an optical fiber core of medical device including (i) a single core fiber, and (ii) a plurality of core fibers.

Specific embodiments of the disclosure include utilization of a medical instrument, such as a stylet, featuring a multi-core optical fiber and a conductive medium that collectively operate for tracking placement with a body of a patient of the stylet or another medical device (such as a catheter) in which the stylet is disposed. In lieu of a stylet, a guidewire may be utilized. For convenience, embodiments are generally discussed where the optical fiber core is disposed within a stylet; however, the disclosure is not intended to be so limited as the functionality involving detection of the health of an optical fiber core disclosed herein may be implemented regardless of the medical device in which the optical fiber core is disposed.

In some embodiments, the optical fiber core of a stylet is configured to return information for use in identifying its physical state (e.g., shape length, shape, and/or form) of (i) a portion of the stylet (e.g., tip, segment of stylet, etc.) or a portion of a catheter inclusive of at least a portion of the stylet (e.g., tip, segment of catheter, etc.) or (ii) the entirety or a substantial portion of the stylet or catheter within the body of a patient (hereinafter, described as the "physical state of the stylet" or the "physical state of the catheter"). According to one embodiment of the disclosure, the returned information may be obtained from reflected light signals of different spectral widths, where each reflected light signal corresponds to a portion of broadband incident light propagating along a core of the multi-core optical fiber (hereinafter, "core fiber") that is reflected back over the core fiber by a particular sensor located on the core fiber. One illustrative example of the returned information may pertain to a change in signal characteristics of the reflected light signal returned from the sensor, where wavelength shift is correlated to (mechanical) strain on the core fiber.

In some embodiments, the core fiber utilizes a plurality of sensors and each sensor is configured to reflect a different spectral range of the incident light (e.g., different light frequency range). Based on the type and degree of strain asserted on each core fiber, the sensors associated with that core fiber may alter (shift) the wavelength of the reflected light to convey the type and degree of stain on that core fiber at those locations of the stylet occupied by the sensors. The sensors are spatially distributed at various locations of the core fiber between a proximal end and a distal end of the stylet so that shape sensing of the stylet may be conducted based on analytics of the wavelength shifts. Herein, the shape sensing functionality is paired with the ability to simultaneously pass an electrical signal through the same member (stylet) through conductive medium included as part of the stylet.

More specifically, in some embodiments each core fiber of the multi-core optical fiber is configured with an array of sensors, which are spatially distributed over a prescribed length of the core fiber to generally sense external strain those regions of the core fiber occupied by the sensor. Given that each sensor positioned along the same core fiber is configured to reflect light of a different, specific spectral width, the array of sensors enables distributed measurements throughout the prescribed length of the multi-core optical fiber. These distributed measurements may include wavelength shifts having a correlation with strain experienced by the sensor.

According to one embodiment of the disclosure, each sensor may operate as a reflective grating such as a fiber Bragg grating (FBG), namely an intrinsic sensor corresponding to a permanent, periodic refractive index change inscribed into the core fiber. Stated differently, the sensor operates as a light reflective mirror for a specific spectral width (e.g., a specific wavelength or specific range of wavelengths). As a result, as broadband incident light is supplied by an optical light source and propagates through a particular core fiber, upon reaching a first sensor of the distributed array of sensors for that core fiber, light of a prescribed spectral width associated with the first sensor is reflected back to an optical receiver within a console, including a display and the optical light source. The remaining spectrum of the incident light continues propagation through the core fiber toward a distal end of the stylet. The remaining spectrum of the incident light may encounter other sensors from the distributed array of sensors, where each of these sensors is fabricated to reflect light with different specific spectral widths to provide distributed measurements, as described above.

During operation, multiple light reflections (also referred to as "reflected light signals") are returned to the console from each of the plurality of core fibers of the multi-core optical fiber. Each reflected light signal may be uniquely associated with a different spectral width. Information associated with the reflected light signals may be used to determine a three-dimensional representation of the physical state of the stylet within the body of a patient. Herein, the core fibers are spatially separated with the cladding of the multi-mode optical fiber and each core fiber is configured to separately return light of different spectral widths (e.g., specific light wavelength or a range of light wavelengths) reflected from the distributed array of sensors fabricated in each of the core fibers. A comparison of detected shifts in wavelength of the reflected light returned by a center core fiber (operating as a reference) and the surrounding, periphery core fibers may be used to determine the physical state of the stylet.

During vasculature insertion and advancement of the catheter, the clinician may rely on the console to visualize a current physical state (e.g., shape) of a catheter guided by the stylet to avoid potential path deviations. As the periphery core fibers reside at spatially different locations within the cladding of the multi-mode optical fiber, changes in angular orientation (such as bending with respect to the center core fiber, etc.) of the stylet imposes different types (e.g., compression or tension) and degrees of strain on each of the periphery core fibers as well as the center core fiber. The different types and/or degree of strain may cause the sensors of the core fibers to apply different wavelength shifts, which can be measured to extrapolate the physical state of the stylet (catheter).

Embodiments of the disclosure may include a combination of one or more of the methodologies to determine the location of a distal tip of a body of implementation (e.g., an introducer wire, a guidewire, a stylet within a needle, a needle with fiber optic inlayed into the cannula, a stylet configured for use with a catheter, an optical fiber between a needle and a catheter, and/or an optical fiber integrated into a catheter) and/or various defects of a vessel of a patient through which the body of implementation is advancing. For example, some embodiments are directed to detection of the distal tip of the body of implementation advancing through the Super Vena Cava (SVC) toward the right atrium of the patient's heart, where the detection may be based at least in part on detecting fluctuations in the tip of the body of implementation and correlated against expected fluctuations caused by the rhythm of the heart. For instance, certain embodiments include the logic configured to perform runtime analytics, heuristics and/or machine-learning techniques to correlate detected fluctuations of the distal tip of the body of implementation with previously detected tip fluctuations (e.g., experiential knowledge).

Further embodiments of the disclosure may include integration with any combination of the following, as will be discussed below: electrocardiogram (ECG) signaling systems, ultrasound systems, fiber optic shape sensing techniques, tip location techniques, tip confirmation techniques, impedance/conductance sensing, confirmation of catheter advancement techniques (e.g., a fluctuating body of implementation stops/changes in fluctuation as catheter tip is advanced over this body), blood pressure, and/or blood flow direction identification. It should be noted that embodiments containing an optical fiber core either advancing in, or integrated with, a body of implementation and void of other detection systems may be compatible for use with a magnetic resonance imaging system.

In some embodiments, as an optic fiber is relatively flexible, the body of implementation may be reinforced through, for example, one or more layers of reinforcing or layering material, where such reinforcement may provide a degree of stiffness to the length of the body of implementation. In some such embodiments, the amount of reinforcement may vary along the length of the body of implementation such that degree of stiffness varies accordingly. For example, in one exemplary embodiment, the amount of reinforcement provided may be a first amount for a first portion of the body of implementation and a second, less amount of a second portion (e.g., where the second portion is the distal tip). In such an example, the level of stiffness would be less at the distal tip than for the remaining length of the body of implementation. Such an embodiment would provide for greater flexibility at the distal tip thereby enabling a greater range of motion motivated by blood flow, turbulence, etc. The greater range of motion may be measured by the optic fiber or other sensors as described herein. As a result, such an exemplary embodiment may be better suited to measure movement at the distal tip of the body of implementation than embodiments having a uniform stiffness along the length of the body of implementation.

Additionally, the body of implementation may include one or more protrusions that extend from the body of implementation that are configured to amplify the forces being experienced by the body of implementation. In some embodiments, the protrusions may be deployable during advancement of the body of implementation in the vasculature of the patient. For instance, logic of the console may be configured to receive user input initiating deployment such that, in response, the logic transmits a signal that causes deployment (e.g., a flap may be extended from body of implementation in a direction substantially perpendicular to the direction of the anticipated (or detected) force or motion. In such embodiments, the protrusions may experience greater fluctuations with each passing volume of blood, vessel spasm, etc., as compared to a body of implementation without such protrusions.

Some embodiments of the disclosure are directed to a medical device system for detecting a current location of a distal tip of a medical device within a patient vasculature. In some embodiments, the system includes the medical device configured to operate in a first modality for obtaining first data indicative of a first location within the patient vasculature, and a console including one or more processors and a non-transitory computer-readable medium having stored thereon logic, when executed by the one or more processors, causes operations including: obtaining second data that is indicative of a second location within the patient vasculature, performing a confirmation process that includes determining whether the second location corresponds to the first location within a predetermined threshold, and when the second location is determined to correspond to the first location within the predetermined threshold, determining that the first location accurately indicates the current location of the distal tip of the medical device.

The first modality may be a fiber optic modality, and wherein the medical device comprises an optical fiber having one or more of core fibers, each of the one or more core fibers including a plurality of sensors distributed along a longitudinal length of a corresponding core fiber and each sensor of the plurality of sensors being configured to (i) reflect a light signal of a different spectral width based on received incident light, and (ii) change a characteristic of the reflected light signal based on strain experienced by the optical fiber. The operations may further include: providing a broadband incident light signal to the optical fiber, receiving reflected light signals of different spectral widths of the broadband incident light by one or more of the plurality of sensors, and processing the reflected light signals associated with the one or more of core fibers to determine the first data indicative of a first location.

The first modality may be any of a fiber optic modality, a magnetically-based tip location system (TLS) modality, or an electrocardiogram (ECG) monitoring system modality. The second data may represent fluctuations of the distal tip of the medical device and the second data may be obtained through a second modality, wherein the second modality is any of a fiber optic modality, a magnetically-based tip location system (TLS) modality, or an electrocardiogram (ECG) monitoring system modality, and wherein the second modality is different than the first modality. The second data may include one or more of: a shape of the medical device determined from fiber optic data, a path taken by the medical device while advancing through the patient vasculature, an insertion length of the medical device, a temperature measured by the medical device, a diameter of a vessel within the patient vasculature, fluctuation data representing fluctuations of the distal tip of the medical device, a pressure measured by the medical device, ECG data, a direction of blood flow within the patient vasculature, or imaging data being one of an intravascular ultrasound, a fluoroscopy image, or a magnetic resonance image (MRI). The medical device may be one of an introducer wire, a guidewire, a stylet, a stylet within a needle, a needle, or a catheter.

Other embodiments of the disclosure are directed to a method for detecting a current location of a distal tip of a medical device within a patient vasculature and non-transitory computer-readable medium having stored thereon logic that, when executed by one or more processors, causes operations of the method. The operations of the method may be those referenced above as performed by either the medical device and/or the console with respect to some embodiments of the system of the disclosure.

These and other features of the concepts provided herein will become more apparent to those of skill in the art in view of the accompanying drawings and following description, which disclose particular embodiments of such concepts in greater detail.

BRIEF DESCRIPTION OF THE DRAWINGS

Embodiments of the disclosure are illustrated by way of example and not by way of limitation in the figures of the accompanying drawings, in which like references indicate similar elements and in which:

FIG. 3A is a first exemplary embodiment of the stylet of FIG. 1A supporting both an optical and electrical signaling in accordance with some embodiments;

FIG. 3B is a cross sectional view of the stylet of FIG. 3A in accordance with some embodiments;

FIG. 4A is a second exemplary embodiment of the stylet of FIG. 1B in accordance with some embodiments;

FIG. 4B is a cross sectional view of the stylet of FIG. 4A in accordance with some embodiments;

FIG. 12A shows an embodiment of a medical device for localization of a body lumen juncture in accordance with some embodiments;

FIG. 12B shows another embodiment of a medical device for localization of a body lumen juncture in accordance with some embodiments.

DETAILED DESCRIPTION

Figure 1A:
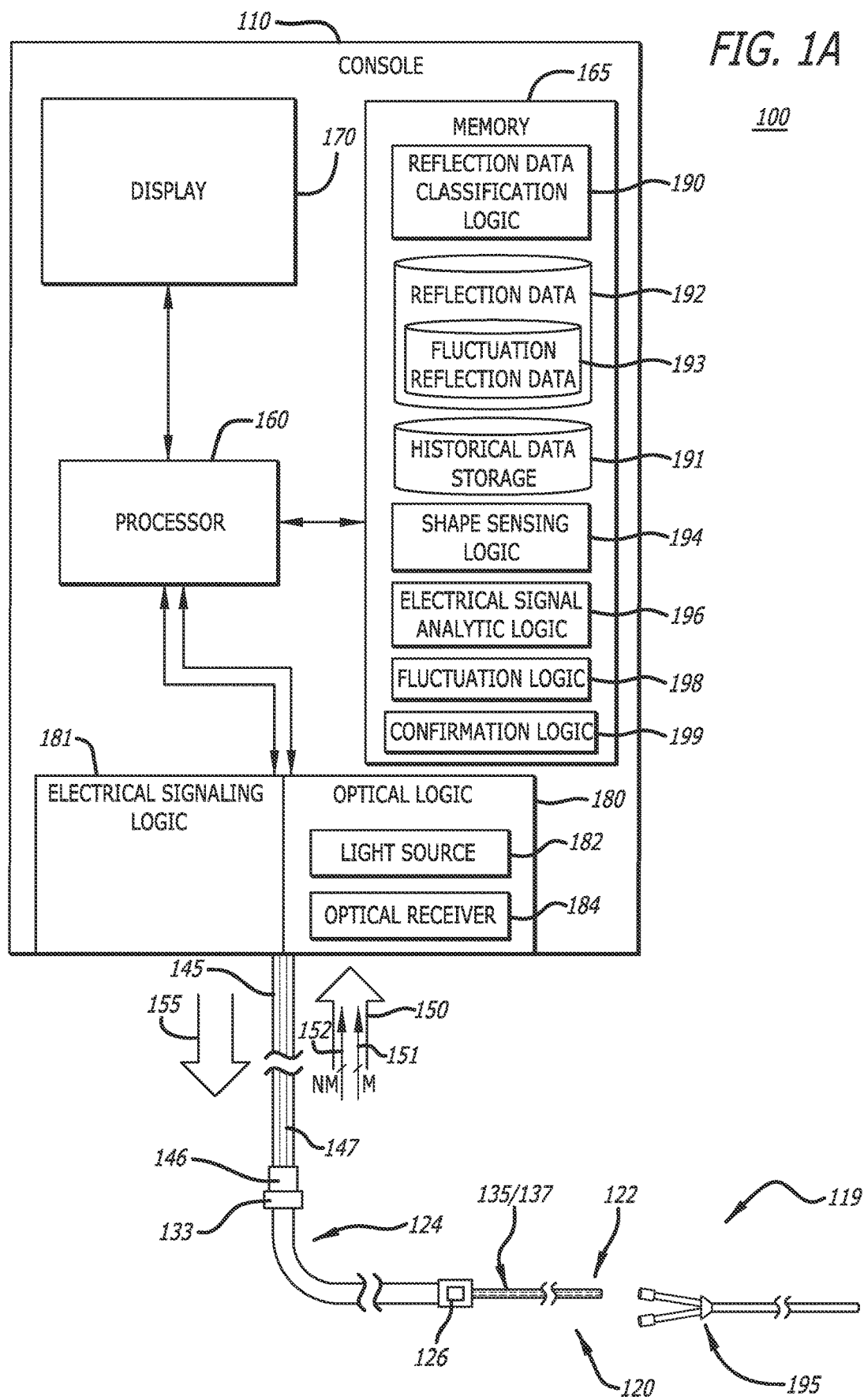
FIG. 1A is an illustrative embodiment of a medical instrument monitoring system including a medical instrument with optic shape sensing and fiber optic-based oximetry capabilities in accordance with some embodiments.

Before some particular embodiments are disclosed in greater detail, the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal end portion" of, for example, a probe disclosed herein includes a portion of the probe intended to be near a clinician when the probe is used on a patient. Likewise, a "proximal length" of, for example, the probe includes a length of the probe intended to be near the clinician when the probe is used on the patient. A "proximal end" of, for example, the probe includes an end of the probe intended to be near the clinician when the probe is used on the patient. The proximal portion, the proximal end portion, or the proximal length of the probe can include the proximal end of the probe; however, the proximal portion, the proximal end portion, or the proximal length of the probe need not include the proximal end of the probe. That is, unless context suggests otherwise, the proximal portion, the proximal end portion, or the proximal length of the probe is not a terminal portion or terminal length of the probe.

With respect to "distal," a "distal portion" or a "distal end portion" of, for example, a probe disclosed herein includes a portion of the probe intended to be near or in a patient when the probe is used on the patient. Likewise, a "distal length" of, for example, the probe includes a length of the probe intended to be near or in the patient when the probe is used on the patient. A "distal end" of, for example, the probe includes an end of the probe intended to be near or in the patient when the probe is used on the patient. The distal portion, the distal end portion, or the distal length of the probe can include the distal end of the probe; however, the distal portion, the distal end portion, or the distal length of the probe need not include the distal end of the probe. That is, unless context suggests otherwise, the distal portion, the distal end portion, or the distal length of the probe is not a terminal portion or terminal length of the probe.

The term "logic" may be representative of hardware, firmware or software that is configured to perform one or more functions. As hardware, the term logic may refer to or include circuitry having data processing and/or storage functionality. Examples of such circuitry may include, but are not limited or restricted to a hardware processor (e.g., microprocessor, one or more processor cores, a digital signal processor, a programmable gate array, a microcontroller, an application specific integrated circuit "ASIC", etc.), a semiconductor memory, or combinatorial elements.

Additionally, or in the alternative, the term logic may refer to or include software such as one or more processes, one or more instances, Application Programming Interface(s) (API), subroutine(s), function(s), applet(s), servlet(s), routine(s), source code, object code, shared library/dynamic link library (dll), or even one or more instructions. This software may be stored in any type of a suitable non-transitory storage medium, or transitory storage medium (e.g., electrical, optical, acoustical or other form of propagated signals such as carrier waves, infrared signals, or digital signals). Examples of a non-transitory storage medium may include, but are not limited or restricted to a programmable circuit; non-persistent storage such as volatile memory (e.g., any type of random-access memory "RAM"); or persistent storage such as non-volatile memory (e.g., read-only memory "ROM", power-backed RAM, flash memory, phase-change memory, etc.), a solid-state drive, hard disk drive, an optical disc drive, or a portable memory device. As firmware, the logic may be stored in persistent storage.

I. Fiber Optic Shape Sensing

Referring to FIG. 1A, an illustrative embodiment of a medical instrument monitoring system including a medical instrument with optic shape sensing and fiber optic-based oximetry capabilities is shown in accordance with some embodiments. As shown, the system 100 generally includes a console 110 and a stylet assembly 119 communicatively coupled to the console 110. For this embodiment, the stylet assembly 119 includes an elongate probe (e.g., stylet) 120 on its distal end 122 and a console connector 133 on its proximal end 124, where the stylet 120 is configured to advance within a patient vasculature either through, or in conjunction with, a catheter 195. The console connector 133 enables the stylet assembly 119 to be operably connected to the console 110 via an interconnect 145 including one or more optical fibers 147 (hereinafter, "optical fiber(s)") and a conductive medium terminated by a single optical/electric connector 146 (or terminated by dual connectors). Herein, the connector 146 is configured to engage (mate) with the console connector 133 to allow for the propagation of light between the console 110 and the stylet assembly 119 as well as the propagation of electrical signals from the stylet 120 to the console 110.

An exemplary implementation of the console 110 includes a processor 160, a memory 165, a display 170 and optical logic 180, although it is appreciated that the console 110 can take one of a variety of forms and may include additional components (e.g., power supplies, ports, interfaces, etc.) that are not directed to aspects of the disclosure. An illustrative example of the console 110 is illustrated in U.S. Publication No. 2019/0237902, the entire contents of which are incorporated by reference herein. The processor 160, with access to the memory 165 (e.g., non-volatile memory or non-transitory, computer-readable medium), is included to control functionality of the console 110 during operation. As shown, the display 170 may be a liquid crystal diode (LCD) display integrated into the console 110 and employed as a user interface to display information to the clinician, especially during a catheter placement procedure (e.g., cardiac catheterization). In another embodiment, the display 170 may be separate from the console 110. Although not shown, a user interface is configured to provide user control of the console 110.

For both embodiments, the content depicted by the display 170 may change according to which mode the stylet 120 is configured to operate: optical, tip location system ("TLS") (magnetically-based via permanent magnet(s) or electromagnet(s)), ECG, or another modality. In optical mode, the content rendered by the display 170 may constitute a two-dimensional (2D) or three-dimensional (3D) representation of the physical state (e.g., length, shape, form, and/or orientation) of the stylet 120 computed from characteristics of reflected light signals 150 returned to the console 110. The reflected light signals 150 constitute light of a specific spectral width of broadband incident light 155 reflected back to the console 110. According to one embodiment of the disclosure, the reflected light signals 150 may pertain to various discrete portions (e.g., specific spectral widths) of broadband incident light 155 transmitted from and sourced by the optical logic 180, as described below According to one embodiment of the disclosure, an activation control 126, included on the stylet assembly 119, may be used to set the stylet 120 into a desired operating mode and selectively alter operability of the display 170 by the clinician to assist in medical device placement. For example, based on the modality of the stylet 120, the display 170 of the console 110 can be employed for optical modality-based guidance during catheter advancement through the vasculature or TLS modality to determine the physical state (e.g., length, form, shape, orientation, etc.) of the stylet 120. In one embodiment, information from multiple modes, such as optical, TLS or ECG for example, may be displayed concurrently (e.g., at least partially overlapping in time).

Referring still to FIG. 1A, the optical logic 180 is configured to support operability of the stylet assembly 119 and enable the return of information to the console 110, which may be used to determine the physical state associated with the stylet 120 along with monitored electrical signals such as ECG signaling via an electrical signaling logic 181 that supports receipt and processing of the received electrical signals from the stylet 120 (e.g., ports, analog-to-digital conversion logic, etc.). The physical state of the stylet 120 may be based on changes in characteristics of the reflected light signals 150 received at the console 110 from the stylet 120. The characteristics may include shifts in wavelength caused by strain on certain regions of the core fibers integrated within an optical fiber core 135 positioned within or operating as the stylet 120, as shown below. As discussed herein, the optical fiber core 135 may be comprised of core fibers $137_1$-$137_M$ (M=1 for a single core, and M≥2 for a multi-core), where the core fibers $137_1$-$137_M$ may collectively be referred to as core fiber(s) 137. Unless otherwise specified or the instant embodiment requires an alternative interpretation, embodiments discussed herein will refer to a multi-core optical fiber 135. From information associated with the reflected light signals 150, the console 110 may determine (through computation or extrapolation of the wavelength shifts) the physical state of the stylet 120, and that of the catheter 195 configured to receive the stylet 120.

According to one embodiment of the disclosure, as shown in FIG. 1A, the optical logic 180 may include a light source 182 and an optical receiver 184. The light source 182 is configured to transmit the incident light 155 (e.g., broadband) for propagation over the optical fiber(s) 147 included in the interconnect 145, which are optically connected to the multi-core optical fiber core 135 within the stylet 120. In one embodiment, the light source 182 is a tunable swept laser, although other suitable light sources can also be employed in addition to a laser, including semi-coherent light sources, LED light sources, etc.

The optical receiver 184 is configured to: (i) receive returned optical signals, namely reflected light signals 150 received from optical fiber-based reflective gratings (sensors) fabricated within each core fiber of the multi-core optical fiber 135 deployed within the stylet 120, and (ii) translate the reflected light signals 150 into reflection data (from repository 192), namely data in the form of electrical signals representative of the reflected light signals including wavelength shifts caused by strain. The reflected light signals 150 associated with different spectral widths may include reflected light signals 151 provided from sensors positioned in the center core fiber (reference) of the multi-core optical fiber 135 and reflected light signals 152 provided from sensors positioned in the periphery core fibers of the multi-core optical fiber 135, as described below. Herein, the optical receiver 184 may be implemented as a photodetector, such as a positive-intrinsic-negative "PIN" photodiode, avalanche photodiode, or the like.

As shown, both the light source 182 and the optical receiver 184 are operably connected to the processor 160, which governs their operation. Also, the optical receiver 184 is operably coupled to provide the reflection data (from repository 192) to the memory 165 for storage and processing by reflection data classification logic 190. The reflection data classification logic 190 may be configured to: (i) identify which core fibers pertain to which of the received reflection data (from repository 192) and (ii) segregate the reflection data stored with a repository 192 provided from reflected light signals 150 pertaining to similar regions of the stylet 120 or spectral widths into analysis groups. The reflection data for each analysis group is made available to shape sensing logic 194 for analytics.

According to one embodiment of the disclosure, the shape sensing logic 194 is configured to compare wavelength shifts measured by sensors deployed in each periphery core fiber at the same measurement region of the stylet 120 (or same spectral width) to the wavelength shift at a center core fiber of the multi-core optical fiber 135 positioned along central axis and operating as a neutral axis of bending. From these analytics, the shape sensing logic 194 may determine the shape the core fibers have taken in 3D space and may further determine the current physical state of the catheter 195 in 3D space for rendering on the display 170.

According to one embodiment of the disclosure, the shape sensing logic 194 may generate a rendering of the current physical state of the stylet 120 (and potentially the catheter 195), based on heuristics or run-time analytics. For example, the shape sensing logic 194 may be configured in accordance with machine-learning techniques to access a data store (library) with pre-stored data (e.g., images, etc.) pertaining to different regions of the stylet 120 (or catheter 195) in which reflected light from core fibers have previously experienced similar or identical wavelength shifts. From the pre-stored data, the current physical state of the stylet 120 (or catheter 195) may be rendered. Alternatively, as another example, the shape sensing logic 194 may be configured to determine, during run-time, changes in the physical state of each region of the multi-core optical fiber 135 based on at least: (i) resultant wavelength shifts experienced by different core fibers within the optical fiber 135, and (ii) the relationship of these wavelength shifts generated by sensors positioned along different periphery core fibers at the same cross-sectional region of the multi-core optical fiber 135 to the wavelength shift generated by a sensor of the center core fiber at the same cross-sectional region. It is contemplated that other processes and procedures may be performed to utilize the wavelength shifts as measured by sensors along each of the core fibers within the multi-core optical fiber 135 to render appropriate changes in the physical state of the stylet 120 (and/or catheter 195), especially to enable guidance of the stylet 120, when positioned at a distal tip of the catheter 195, within the vasculature of the patient and at a desired destination within the body.

The console 110 may further include electrical signaling logic 181, which is positioned to receive one or more electrical signals from the stylet 120. The stylet 120 is configured to support both optical connectivity as well as electrical connectivity. The electrical signaling logic 181 receives the electrical signals (e.g., ECG signals) from the stylet 120 via the conductive medium. The electrical signals may be processed by electrical signal logic 196, executed by the processor 160, to determine ECG waveforms for display.

Additionally, the console 110 includes a fluctuation logic 198 that is configured to analyze at least a subset of the wavelength shifts measured by sensors deployed in each of the core fibers 137. In particular, the fluctuation logic 198 is configured to analyze wavelength shifts measured by sensors of core fibers 137, where such corresponds to an analysis of the fluctuation of the distal tip of the stylet 120 (or "tip fluctuation analysis"). In some embodiments, the fluctuation logic 198 analyzes the wavelength shifts measured by sensors at a distal end of the core fibers 137. The tip fluctuation analysis includes at least a correlation of detected movements of the distal tip of the stylet 120 (or other medical device or instrument) with experiential knowledge comprising previously detected movements (fluctuations), and optionally, other current measurements such as ECG signals. The experiential knowledge may include previously detected movements in various locations within the vasculature (e.g., SVC, Inferior Vena Cava (IVC), right atrium, azygos vein, other blood vessels such as arteries and veins) under normal, healthy conditions and in the presence of defects (e.g., vessel constriction, vasospasm, vessel occlusion, etc.). Thus, the tip fluctuation analysis may result in a confirmation of tip location and/or detection of a defect affecting a blood vessel.

It should be noted that the fluctuation logic 198 need not perform the same analyses as the shape sensing logic 194. For instance, the shape sensing logic 194 determines a 3D shape of the stylet 120 by comparing wavelength shifts in outer core fibers of a multi-core optical fiber to a center, reference core fiber. The fluctuation logic 198 may instead correlate the wavelength shifts to previously measured wavelength shifts and optionally other current measurements without distinguishing between wavelength shifts of outer core fibers and a center, reference core fiber as the tip fluctuation analysis need not consider direction or shape within a 3D space.

In some embodiments, e.g., those directed at tip location confirmation, the analysis of the fluctuation logic 198 may utilize electrical signals (e.g., ECG signals) measured by the electrical signaling logic 181. For example, the fluctuation logic 198 may compare the movements of a subsection of the stylet 120 (e.g., the distal tip) with electrical signals indicating impulses of the heart (e.g., the heartbeat). Such a comparison may reveal whether the distal tip is within the SVC or the right atrium based on how closely the movements correspond to a rhythmic heartbeat.

In various embodiments, a display and/or alert may be generated based on the fluctuation analysis. For instance, the fluctuation logic 198 may generate a graphic illustrating the detected fluctuation compared to previously detected tip fluctuations and/or the anatomical movements of the patient body such as rhythmic pulses of the heart and/or expanding and contracting of the lungs. In one embodiment, such a graphic may include a dynamic visualization of the present medical device moving in accordance with the detected fluctuations adjacent to a secondary medical device moving in accordance with previously detected tip fluctuations. In some embodiments, the location of a subsection of the medical device may be obtained from the shape sensing logic 194 and the dynamic visualization may be location-specific (e.g., such that the previously detected fluctuations illustrate expected fluctuations for the current location of the subsection). In alternative embodiments, the dynamic visualization may illustrate a comparison of the dynamic movements of the subsection to one or more subsections moving in accordance with previously detected fluctuations of one or more defects affecting the blood vessel.

According to one embodiment of the disclosure, the fluctuation logic 198 may determine whether movements of one or more subsections of the stylet 120 indicate a location of a particular subsection of the stylet 120 or a defect affecting a blood vessel and, as a result, of the catheter 195, based on heuristics or run-time analytics. For example, the fluctuation logic 198 may be configured in accordance with machine-learning techniques to access a data store (library) with pre-stored data (e.g., experiential knowledge of previously detected tip fluctuation data, etc.) pertaining to different regions (subsections) of the stylet 120. Specifically, such an embodiment may include processing of a machine-learning model trained using the experiential knowledge, where the detected fluctuations serve as input to the trained model and processing of the trained model results in a determination as to how closely the detected fluctuations correlate to one or more locations within the vasculature of the patient and/or one or more defects affecting a blood vessel.

In some embodiments, the fluctuation logic 198 may be configured to determine, during run-time, whether movements of one or more subsections of the stylet 120 (and the catheter 195) indicate a location of a particular subsection of the stylet 120 or a defect affecting a blood vessel, based on at least (i) resultant wavelength shifts experienced by the core fibers 137 within the one or more subsections, and (ii) the correlation of these wavelength shifts generated by sensors positioned along different core fibers at the same cross-sectional region of the stylet 120 (or the catheter 195) to previously detected wavelength shifts generated by corresponding sensors in a core fiber at the same cross-sectional region. It is contemplated that other processes and procedures may be performed to utilize the wavelength shifts as measured by sensors along each of the core fibers 137 to render appropriate movements in the distal tip of the stylet 120 and/or the catheter 195.

The console 110 may also include a confirmation logic 199 stored on the non-transitory, computer-readable medium ("storage" or "memory") 165 that is, upon execution by the processor 160, configured to perform operations intended to confirm the location of the distal tip of a medical instrument that is advancing within a patient vasculature. More specifically, the confirmation logic 199 is configured to receive data indicative of a location within the patient vasculature and determine whether the data indicate the same or substantially the same location (e.g., within a threshold distance) or indicate differing locations. For instance, the confirmation logic 199 may receive a first location as determined by a first modality (e.g., fiber optic shape sensing) and fluctuation data measured by a second modality (e.g., internal impedance). The confirmation logic 199 is configured to determine whether the impedance fluctuation data is indicative of the first location determined via fiber optic shape sensing. In such an example, the confirmation logic 199 may retrieve stored fluctuation data corresponding to the first location and compare the stored fluctuation data with the impedance fluctuation data. The confirmation logic 199 determines that the impedance fluctuation data confirms that the distal tip is at the first location as determined by the first modality when the stored fluctuation data and the impedance fluctuation data are equivalent or within a threshold of each other. The confirmation logic 199 may receive various forms of data and perform various operations to confirm whether the data indicate the same or substantially the same location. Further examples will be discussed below. It should be understood that any operations discussed below with respect to performing location confirmation may be performed by the confirmation logic 199. Additionally, any reference to obtaining stored or "historical" data such as stored lumen profiles or stored ECG data may be stored in historical data storage 191.

Figure 1B:
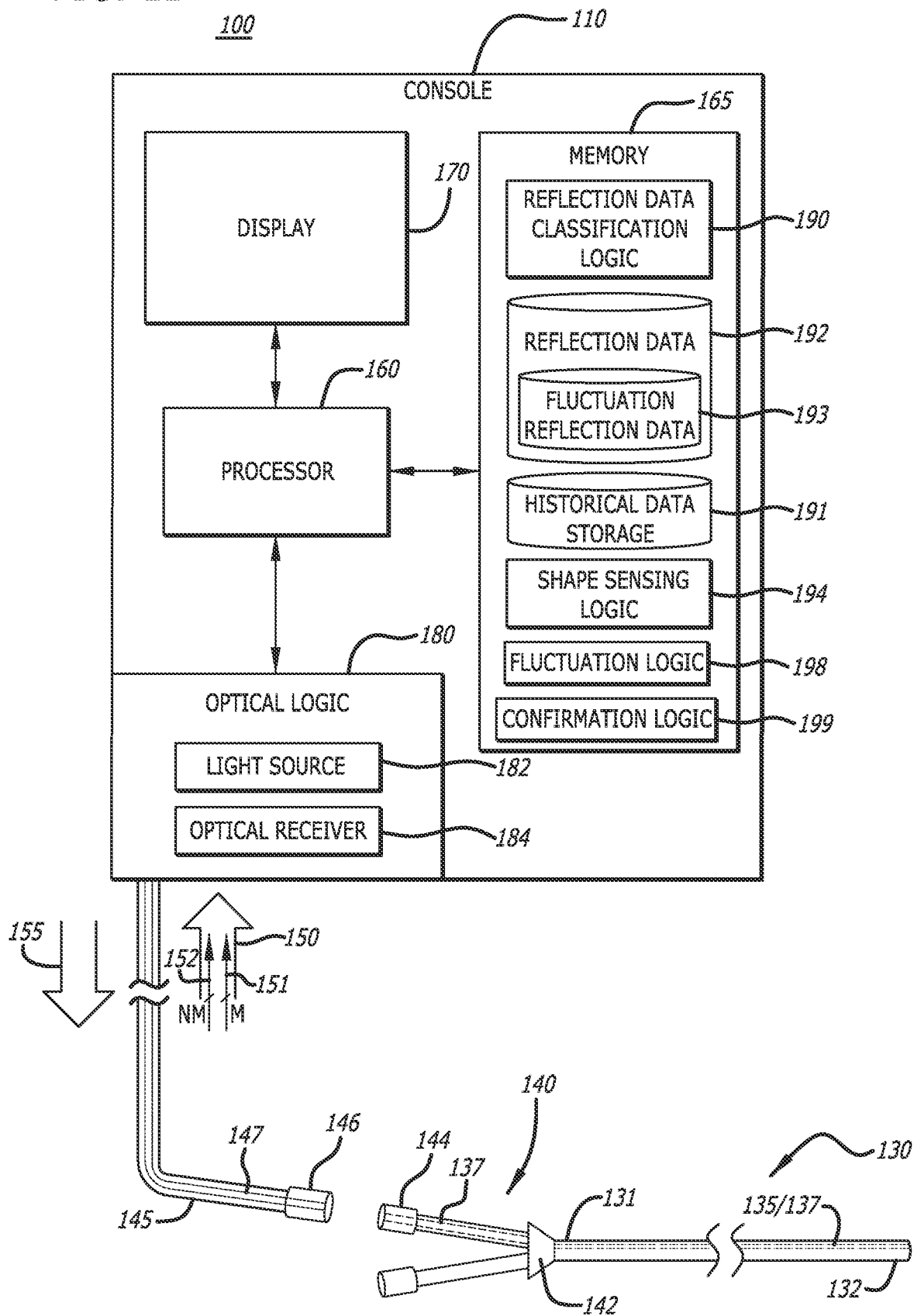
FIG. 1B is an alternative illustrative embodiment of the medical instrument monitoring system 100 in accordance with some embodiments.

Referring to FIG. 1B, an alternative exemplary embodiment of a medical instrument monitoring system 100 is shown. Herein, the medical instrument monitoring system 100 features a console 110 and a medical instrument 130 communicatively coupled to the console 110. For this embodiment, the medical instrument 130 corresponds to a catheter, which features an integrated tubing with two or more lumen extending between a proximal end 131 and a distal end 132 of the integrated tubing. The integrated tubing (sometimes referred to as "catheter tubing") is in communication with one or more extension legs 140 via a bifurcation hub 142. An optical-based catheter connector 144 may be included on a proximal end of at least one of the extension legs 140 to enable the catheter 130 to operably connect to the console 110 via an interconnect 145 or another suitable component. Herein, the interconnect 145 may include a connector 146 that, when coupled to the optical-based catheter connector 144, establishes optical connectivity between one or more optical fibers 147 (hereinafter, "optical fiber(s)") included as part of the interconnect 145 and core fibers 137 deployed within the catheter 130 and integrated into the tubing. Alternatively, a different combination of connectors, including one or more adapters, may be used to optically connect the optical fiber(s) 147 to the core fibers 137 within the catheter 130. The core fibers 137 deployed within the catheter 130 as illustrated in FIG. 1B include the same characteristics and perform the same functionalities as the core fibers 137 deployed within the stylet 120 of FIG. 1A.

The optical logic 180 is configured to support graphical rendering of the catheter 130, most notably the integrated tubing of the catheter 130, based on characteristics of the reflected light signals 150 received from the catheter 130. The characteristics may include shifts in wavelength caused by strain on certain regions of the core fibers 137 integrated within (or along) a wall of the integrated tubing, which may be used to determine (through computation or extrapolation of the wavelength shifts) the physical state of the catheter 130, notably its integrated tubing or a portion of the integrated tubing such as a tip or distal end of the tubing to read fluctuations (real-time movement) of the tip (or distal end).

More specifically, the optical logic 180 includes a light source 182. The light source 182 is configured to transmit the broadband incident light 155 for propagation over the optical fiber(s) 147 included in the interconnect 145, which are optically connected to multiple core fibers 137 within the catheter tubing. Herein, the optical receiver 184 is configured to: (i) receive returned optical signals, namely reflected light signals 150 received from optical fiber-based reflective gratings (sensors) fabricated within each of the core fibers 137 deployed within the catheter 130, and (ii) translate the reflected light signals 150 into reflection data (from repository 192), namely data in the form of electrical signals representative of the reflected light signals including wavelength shifts caused by strain. The reflected light signals 150 associated with different spectral widths include reflected light signals 151 provided from sensors positioned in the center core fiber (reference) of the catheter 130 and reflected light signals 152 provided from sensors positioned in the outer core fibers of the catheter 130, as described below.

As noted above, the shape sensing logic 194 is configured to compare wavelength shifts measured by sensors deployed in each outer core fiber at the same measurement region of the catheter (or same spectral width) to the wavelength shift at the center core fiber positioned along central axis and operating as a neutral axis of bending. From these analytics, the shape sensing logic 190 may determine the shape the core fibers have taken in 3D space and may further determine the current physical state of the catheter 130 in 3D space for rendering on the display 170.

According to one embodiment of the disclosure, the shape sensing logic 194 may generate a rendering of the current physical state of the catheter 130, especially the integrated tubing, based on heuristics or run-time analytics. For example, the shape sensing logic 194 may be configured in accordance with machine-learning techniques to access a data store (library) with pre-stored data (e.g., images, etc.) pertaining to different regions of the catheter 130 in which the core fibers 137 experienced similar or identical wavelength shifts. From the pre-stored data, the current physical state of the catheter 130 may be rendered. Alternatively, as another example, the shape sensing logic 194 may be configured to determine, during run-time, changes in the physical state of each region of the catheter 130, notably the tubing, based on at least (i) resultant wavelength shifts experienced by the core fibers 137 and (ii) the relationship of these wavelength shifts generated by sensors positioned along different outer core fibers at the same cross-sectional region of the catheter 130 to the wavelength shift generated by a sensor of the center core fiber at the same cross-sectional region. It is contemplated that other processes and procedures may be performed to utilize the wavelength shifts as measured by sensors along each of the core fibers 137 to render appropriate changes in the physical state of the catheter 130.

Figure 2:
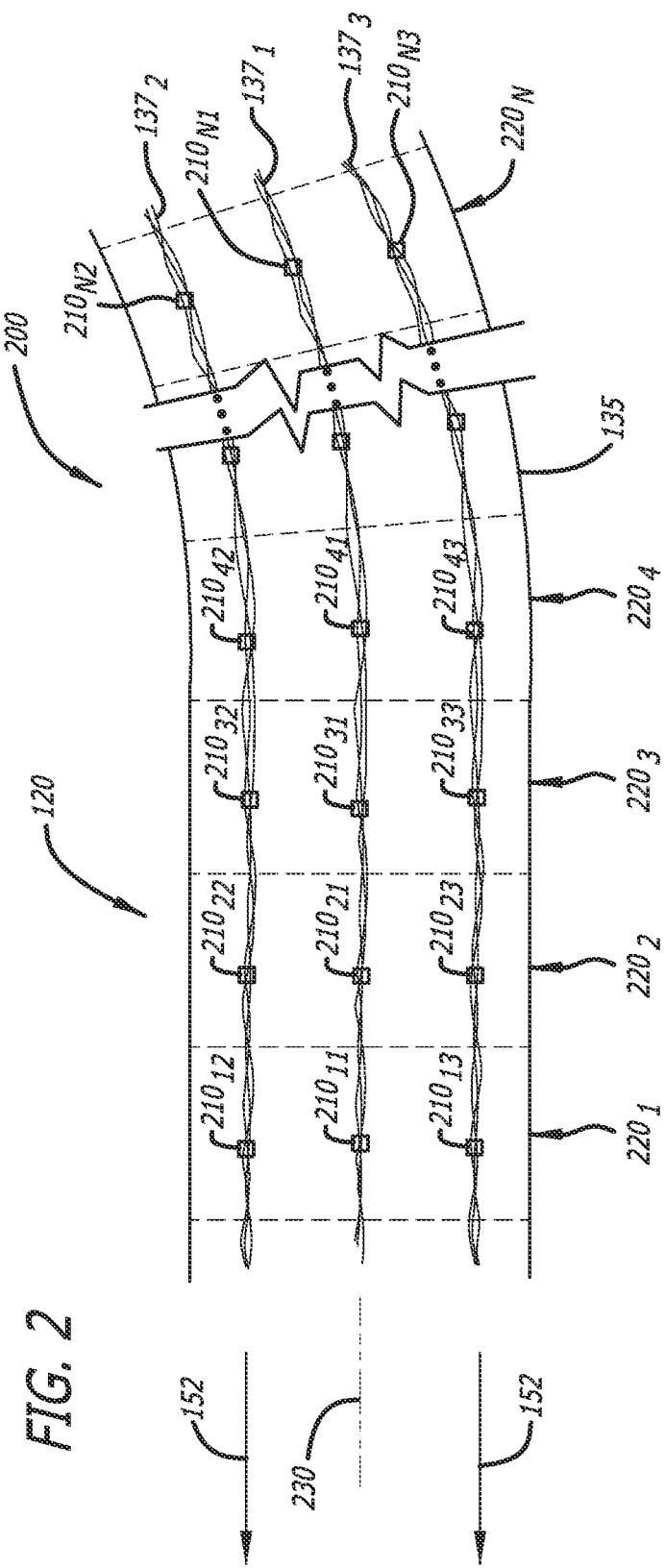
FIG. 2 is an exemplary embodiment of a structure of a section of the multi-core optical fiber included within the stylet 120 of FIG. 1A in accordance with some embodiments.

Referring to FIG. 2, an exemplary embodiment of a structure of a section of the multi-core optical fiber included within the stylet 120 of FIG. 1A is shown in accordance with some embodiments. The multi-core optical fiber section 200 of the multi-core optical fiber 135 depicts certain core fibers $137_1$-$137_M$ (M≥2, M=4 as shown, see FIG. 3A) along with the spatial relationship between sensors (e.g., reflective gratings) $210_{11}$-$210_{NM}$ (N≥2; M≥2) present within the core fibers $137_1$-$137_M$, respectively. As noted above, the core fibers $137_1$-$137_M$ may be collectively referred to as "the core fibers 137."

As shown, the section 200 is subdivided into a plurality of cross-sectional regions $220_1$-$220_N$, where each cross-sectional region $220_1$-$220_N$ corresponds to reflective gratings $210_{11}$-$210_{14}$ ... $210_{N1}$-$210_{N4}$. Some or all of the cross-sectional regions $220_1$ ... $220_N$ may be static (e.g., prescribed length) or may be dynamic (e.g., vary in size among the regions $220_1$ ... $220_N$). A first core fiber $137_1$ is positioned substantially along a center (neutral) axis 230 while core fiber $137_2$ may be oriented within the cladding of the multi-core optical fiber 135, from a cross-sectional, front-facing perspective, to be position on "top" the first core fiber $137_1$. In this deployment, the core fibers $137_3$ and $137_4$ may be positioned "bottom left" and "bottom right" of the first core fiber $137_1$. As examples, FIGS. 3A-4B provides illustrations of such.

Referencing the first core fiber $137_1$ as an illustrative example, when the stylet 120 is operative, each of the reflective gratings $210_1$-$210_N$ reflects light for a different spectral width. As shown, each of the gratings $210_{1i}$-$210_{Ni}$ (1≤i≤M) is associated with a different, specific spectral width, which would be represented by different center frequencies of $f_1 \ldots f_N$, where neighboring spectral widths reflected by neighboring gratings are non-overlapping according to one embodiment of the disclosure.

Herein, positioned in different core fibers $137_2$-$137_3$ but along at the same cross-sectional regions $220$-$220_N$ of the multi-core optical fiber 135, the gratings $210_{12}$-$210_{N2}$ and $210_{13}$-$210_{N3}$ are configured to reflect incoming light at same (or substantially similar) center frequency. As a result, the reflected light returns information that allows for a determination of the physical state of the optical fibers 137 (and the stylet 120) based on wavelength shifts measured from the returned, reflected light. In particular, strain (e.g., compression or tension) applied to the multi-core optical fiber 135 (e.g., at least core fibers $137_2$-$137_3$) results in wavelength shifts associated with the returned, reflected light. Based on different locations, the core fibers $137_1$-$137_4$ experience different types and degree of strain based on angular path changes as the stylet 120 advances in the patient.

For example, with respect to the multi-core optical fiber section 200 of FIG. 2, in response to angular (e.g., radial) movement of the stylet 120 is in the left-veering direction, the fourth core fiber $137_4$ (see FIG. 3A) of the multi-core optical fiber 135 with the shortest radius during movement (e.g., core fiber closest to a direction of angular change) would exhibit compression (e.g., forces to shorten length). At the same time, the third core fiber $137_3$ with the longest radius during movement (e.g., core fiber furthest from the direction of angular change) would exhibit tension (e.g., forces to increase length). As these forces are different and unequal, the reflected light from reflective gratings $210_{N2}$ and $210_{N3}$ associated with the core fibers $137_2$ and $137_3$ will exhibit different changes in wavelength. The differences in wavelength shift of the reflected light signals 150 can be used to extrapolate the physical configuration of the stylet 120 by determining the degrees of wavelength change caused by compression/tension for each of the periphery fibers (e.g., the second core fiber $137_2$ and the third core fiber $137_3$) in comparison to the wavelength of the reference core fiber (e.g., first core fiber $137_1$) located along the neutral axis 230 of the multi-core optical fiber 135. These degrees of wavelength change may be used to extrapolate the physical state of the stylet 120. The reflected light signals 150 are reflected back to the console 110 via individual paths over a particular core fiber $137_1$-$137_M$.

Referring to FIG. 3A, a first exemplary embodiment of the stylet of FIG. 1A supporting both an optical and electrical signaling is shown in accordance with some embodiments. Herein, the stylet 120 features a centrally located multi-core optical fiber 135, which includes a cladding 300 and a plurality of core fibers $137_1$-$137_M$ (M≥2; M=4) residing within a corresponding plurality of lumens $320_1$-$320_M$. While the multi-core optical fiber 135 is illustrated within four (4) core fibers $137_1$-$137_4$, a greater number of core fibers $137_1$-$137_M$ (M>4) may be deployed to provide a more detailed three-dimensional sensing of the physical state (e.g., shape, etc.) of the multi-core optical fiber 135 and the stylet 120 deploying the optical fiber 135.

For this embodiment of the disclosure, the multi-core optical fiber 135 is encapsulated within a concentric braided tubing 310 positioned over a low coefficient of friction layer 335. The braided tubing 310 may feature a "mesh" construction, in which the spacing between the intersecting conductive elements is selected based on the degree of rigidity desired for the stylet 120, as a greater spacing may provide a lesser rigidity, and thereby, a more pliable stylet 120.

According to this embodiment of the disclosure, as shown in FIGS. 3A-3B, the core fibers $137_1$-$137_4$ include (i) a central core fiber $137_1$ and (ii) a plurality of periphery core fibers $137_2$-$137_4$, which are maintained within lumens $320_1$-$320_4$ formed in the cladding 300. According to one embodiment of the disclosure, one or more of the lumens $320_1$-$320_4$ may be configured with a diameter sized to be greater than the diameter of the core fibers $137_1$-$137_4$. By avoiding a majority of the surface area of the core fibers $137_1$-$137_4$ from being in direct physical contact with a wall surface of the lumens $320_1$-$320_4$, the wavelength changes to the incident light are caused by angular deviations in the multi-core optical fiber 135 thereby reducing influence of compression and tension forces being applied to the walls of the lumens $320_1$-$320_M$, not the core fibers $137_1$-$137_M$ themselves.

As further shown in FIGS. 3A-3B, the core fibers $137_1$-$137_4$ may include central core fiber $137_1$ residing within a first lumen $320_1$ formed along the first neutral axis 230 and a plurality of core fibers $137_2$-$137_4$ residing within lumens $320_2$-$320_4$ each formed within different areas of the cladding 300 radiating from the first neutral axis 230. In general, the core fibers $137_2$-$137_4$, exclusive of the central core fiber $137_1$, may be positioned at different areas within a cross-sectional area 305 of the cladding 300 to provide sufficient separation to enable three-dimensional sensing of the multi-core optical fiber 135 based on changes in wavelength of incident light propagating through the core fibers $137_2$-$137_4$ and reflected back to the console for analysis.

For example, where the cladding 300 features a circular cross-sectional area 305 as shown in FIG. 3B, the core fibers $137_2$-$137_4$ may be positioned substantially equidistant from each other as measured along a perimeter of the cladding 300, such as at "top" (12 o'clock), "bottom-left" (8 o'clock) and "bottom-right" (4 o'clock) locations as shown. Hence, in general terms, the core fibers $137_2$-$137_4$ may be positioned within different segments of the cross-sectional area 305. Where the cross-sectional area 305 of the cladding 300 has a distal tip 330 and features a polygon cross-sectional shape (e.g., triangular, square, rectangular, pentagon, hexagon, octagon, etc.), the central core fiber $137_1$ may be located at or near a center of the polygon shape, while the remaining core fibers $137_2$-$137_M$ may be located proximate to angles between intersecting sides of the polygon shape.

Referring still to FIGS. 3A-3B, operating as the conductive medium for the stylet 120, the braided tubing 310 provides mechanical integrity to the multi-core optical fiber 135 and operates as a conductive pathway for electrical signals. For example, the braided tubing 310 may be exposed to a distal tip of the stylet 120. The cladding 300 and the braided tubing 310, which is positioned concentrically surrounding a circumference of the cladding 300, are contained within the same insulating layer 350. The insulating layer 350 may be a sheath or conduit made of protective, insulating (e.g., non-conductive) material that encapsulates both for the cladding 300 and the braided tubing 310, as shown.

Referring to FIG. 4A, a second exemplary embodiment of the stylet of FIG. 1A is shown in accordance with some embodiments. Referring now to FIG. 4A, a second exemplary embodiment of the stylet 120 of FIG. 1A supporting both an optical and electrical signaling is shown. Herein, the stylet 120 features the multi-core optical fiber 135 described above and shown in FIG. 3A, which includes the cladding 300 and the first plurality of core fibers $137_1$-$137_M$ (M≥3; M=4 for embodiment) residing within the corresponding plurality of lumens $320_1$-$320_M$. For this embodiment of the disclosure, the multi-core optical fiber 135 includes the central core fiber $137_1$ residing within the first lumen $320_1$ formed along the first neutral axis 230 and the second plurality of core fibers $137_2$-$137_4$ residing within corresponding lumens $320_2$-$320_4$ positioned in different segments within the cross-sectional area 305 of the cladding 300. Herein, the multi-core optical fiber 135 is encapsulated within a conductive tubing 400. The conductive tubing 400 may feature a "hollow" conductive cylindrical member concentrically encapsulating the multi-core optical fiber 135.

Referring to FIGS. 4A-4B, operating as a conductive medium for the stylet 120 in the transfer of electrical signals (e.g., ECG signals) to the console, the conductive tubing 400 may be exposed up to a tip 410 of the stylet 120. For this embodiment of the disclosure, a conductive epoxy 420 (e.g., metal-based epoxy such as a silver epoxy) may be affixed to the tip 410 and similarly joined with a termination/connection point created at a proximal end 430 of the stylet 120. The cladding 300 and the conductive tubing 400, which is positioned concentrically surrounding a circumference of the cladding 300, are contained within the same insulating layer 440. The insulating layer 440 may be a protective conduit encapsulating both for the cladding 300 and the conductive tubing 400, as shown.

Figure 5A:
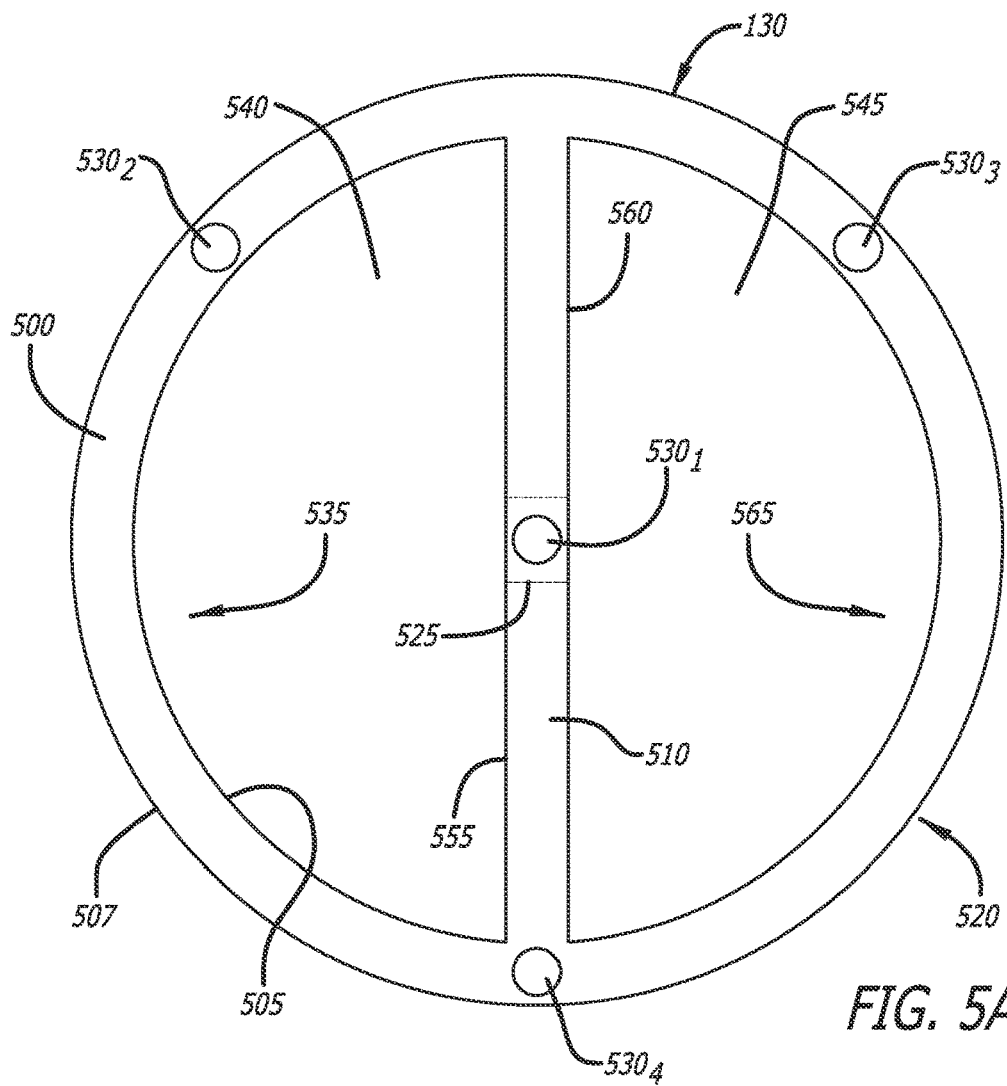
FIG. 5A is an elevation view of a first illustrative embodiment of a catheter including integrated tubing, a diametrically disposed septum, and micro-lumens formed within the tubing and septum in accordance with some embodiments.

Referring to FIG. 5A, an elevation view of a first illustrative embodiment of a catheter including integrated tubing, a diametrically disposed septum, and micro-lumens formed within the tubing and septum is shown in accordance with some embodiments. Herein, the catheter 130 includes integrated tubing, the diametrically disposed septum 510, and the plurality of micro-lumens $530_1$-$530_4$ which, for this embodiment, are fabricated to reside within the wall 500 of the integrated tubing of the catheter 130 and within the septum 510. In particular, the septum 510 separates a single lumen, formed by the inner surface 505 of the wall 500 of the catheter 130, into multiple lumens, namely two lumens 540 and 545 as shown. Herein, the first lumen 540 is formed between a first arc-shaped portion 535 of the inner surface 505 of the wall 500 forming the catheter 130 and a first outer surface 555 of the septum 510 extending longitudinally within the catheter 130. The second lumen 545 is formed between a second arc-shaped portion 565 of the inner surface 505 of the wall 500 forming the catheter 130 and a second outer surfaces 560 of the septum 510.

According to one embodiment of the disclosure, the two lumens 540 and 545 have approximately the same volume. However, the septum 510 need not separate the tubing into two equal lumens. For example, instead of the septum 510 extending vertically (12 o'clock to 6 o'clock) from a front-facing, cross-sectional perspective of the tubing, the septum 510 could extend horizontally (3 o'clock to 9 o'clock), diagonally (1 o'clock to 7 o'clock; 10 o'clock to 4 o'clock) or angularly (2 o'clock to 10 o'clock). In the later configuration, each of the lumens 540 and 545 of the catheter 130 would have a different volume.

With respect to the plurality of micro-lumens $530_1$-$530_4$, the first micro-lumen $530_1$ is fabricated within the septum 510 at or near the cross-sectional center 525 of the integrated tubing. For this embodiment, three micro-lumens $530_2$-$530_4$ are fabricated to reside within the wall 500 of the catheter 130. In particular, a second micro-lumen $530_2$ is fabricated within the wall 500 of the catheter 130, namely between the inner surface 505 and outer surface 507 of the first arc-shaped portion 535 of the wall 500. Similarly, the third micro-lumen $530_3$ is also fabricated within the wall 500 of the catheter 130, namely between the inner and outer surfaces 505/507 of the second arc-shaped portion 555 of the wall 500. The fourth micro-lumen $530_4$ is also fabricated within the inner and outer surfaces 505/507 of the wall 500 that are aligned with the septum 510.

According to one embodiment of the disclosure, as shown in FIG. 5A, the micro-lumens $530_2$-$530_4$ are positioned in accordance with a "top-left" (10 o'clock), "top-right" (2 o'clock) and "bottom" (6 o'clock) layout from a front-facing, cross-sectional perspective. Of course, the micro-lumens $530_2$-$530_4$ may be positioned differently, provided that the micro-lumens $530_2$-$530_4$ are spatially separated along the circumference 520 of the catheter 130 to ensure a more robust collection of reflected light signals from the outer core fibers $570_2$-$570_4$ when installed. For example, two or more of micro-lumens (e.g., micro-lumens $530_2$ and $530_4$) may be positioned at different quadrants along the circumference 520 of the catheter wall 500.

Figure 5B:
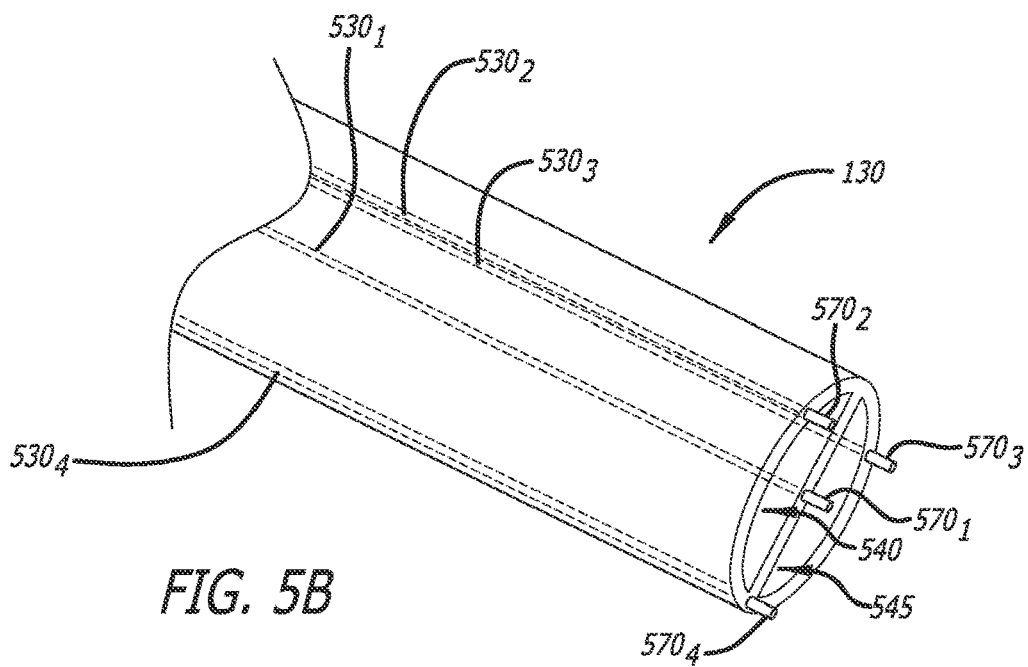
FIG. 5B is a perspective view of the first illustrative embodiment of the catheter of FIG. 5A including core fibers installed within the micro-lumens in accordance with some embodiments.

Referring to FIG. 5B, a perspective view of the first illustrative embodiment of the catheter of FIG. 5A including core fibers installed within the micro-lumens is shown in accordance with some embodiments. According to one embodiment of the disclosure, the second plurality of micro-lumens $530_2$-$530_4$ are sized to retain corresponding outer core fibers $570_2$-$570_4$, where the diameter of each of the second plurality of micro-lumens $530_2$-$530_4$ may be sized just larger than the diameters of the outer core fibers $570_2$-$570_4$. The size differences between a diameter of a single core fiber and a diameter of any of the micro-lumen $530_1$-$530_4$ may range between 0.001 micrometers (μm) and 1000 μm, for example. As a result, the cross-sectional areas of the outer core fibers $570_2$-$570_4$ would be less than the cross-sectional areas of the corresponding micro-lumens $530_2$-$530_4$. A "larger" micro-lumen (e.g., micro-lumen $530_2$) may better isolate external strain being applied to the outer core fiber $570_2$ from strain directly applied to the catheter 130 itself. Similarly, the first micro-lumen $530_1$ may be sized to retain the center core fiber $570_1$, where the diameter of the first micro-lumen $530_1$ may be sized just larger than the diameter of the center core fiber $570_1$.

As an alternative embodiment of the disclosure, one or more of the micro-lumens $530_1$-$530_4$ may be sized with a diameter that exceeds the diameter of the corresponding one or more core fibers $570_1$-$570_4$. However, at least one of the micro-lumens $530_1$-$530_4$ is sized to fixedly retain their corresponding core fiber (e.g., core fiber retained with no spacing between its lateral surface and the interior wall surface of its corresponding micro-lumen). As yet another alternative embodiment of the disclosure, all the micro-lumens $530_1$-$530_4$ are sized with a diameter to fixedly retain the core fibers $570_1$-$570_4$.

Figure 6A:
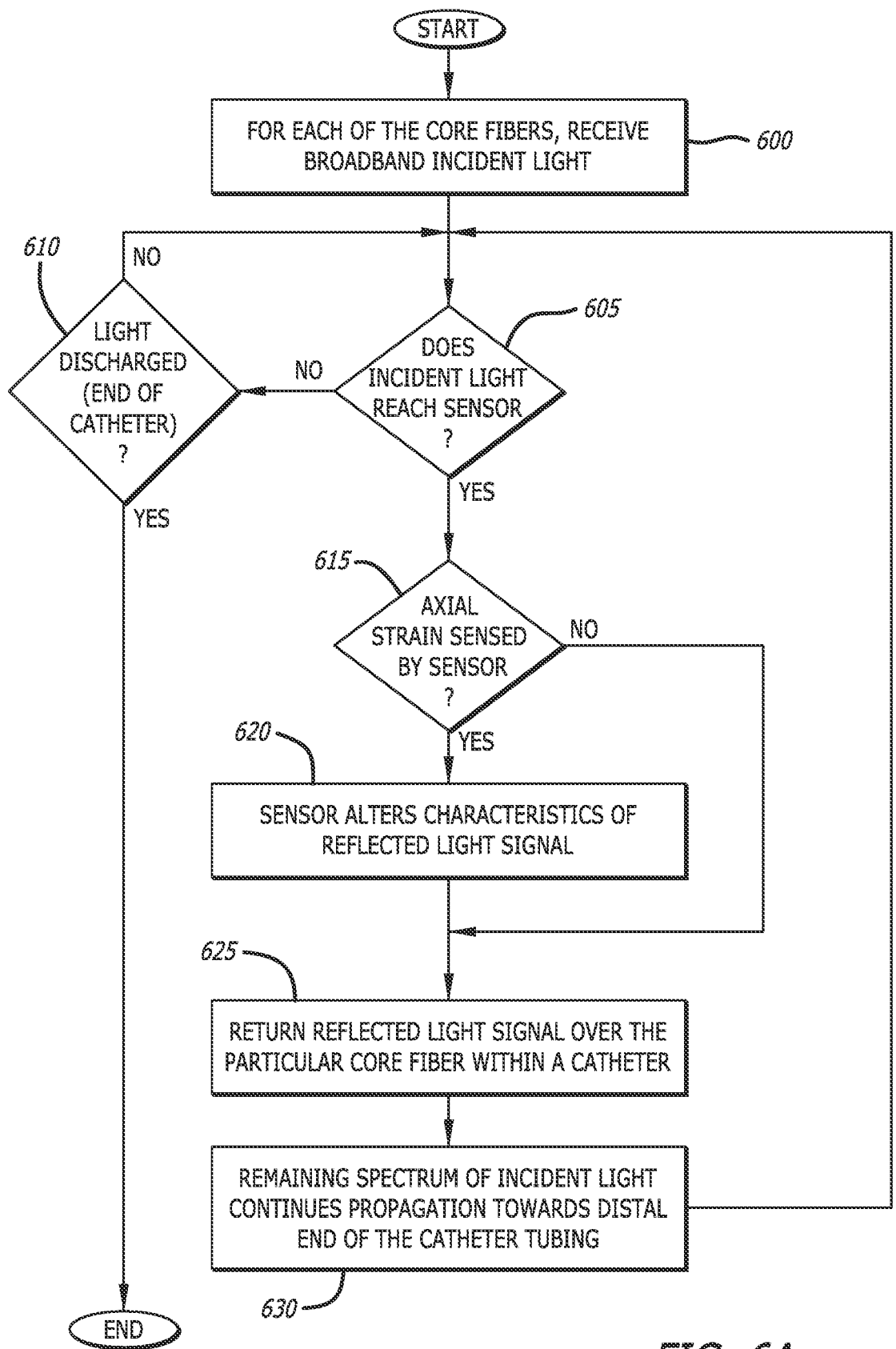
FIGS. 6A-6B are flowcharts of the methods of operations conducted by the medical instrument monitoring system of FIGS. 1A-1B to achieve optic 3D shape sensing in accordance with some embodiments.
Figure 6B:
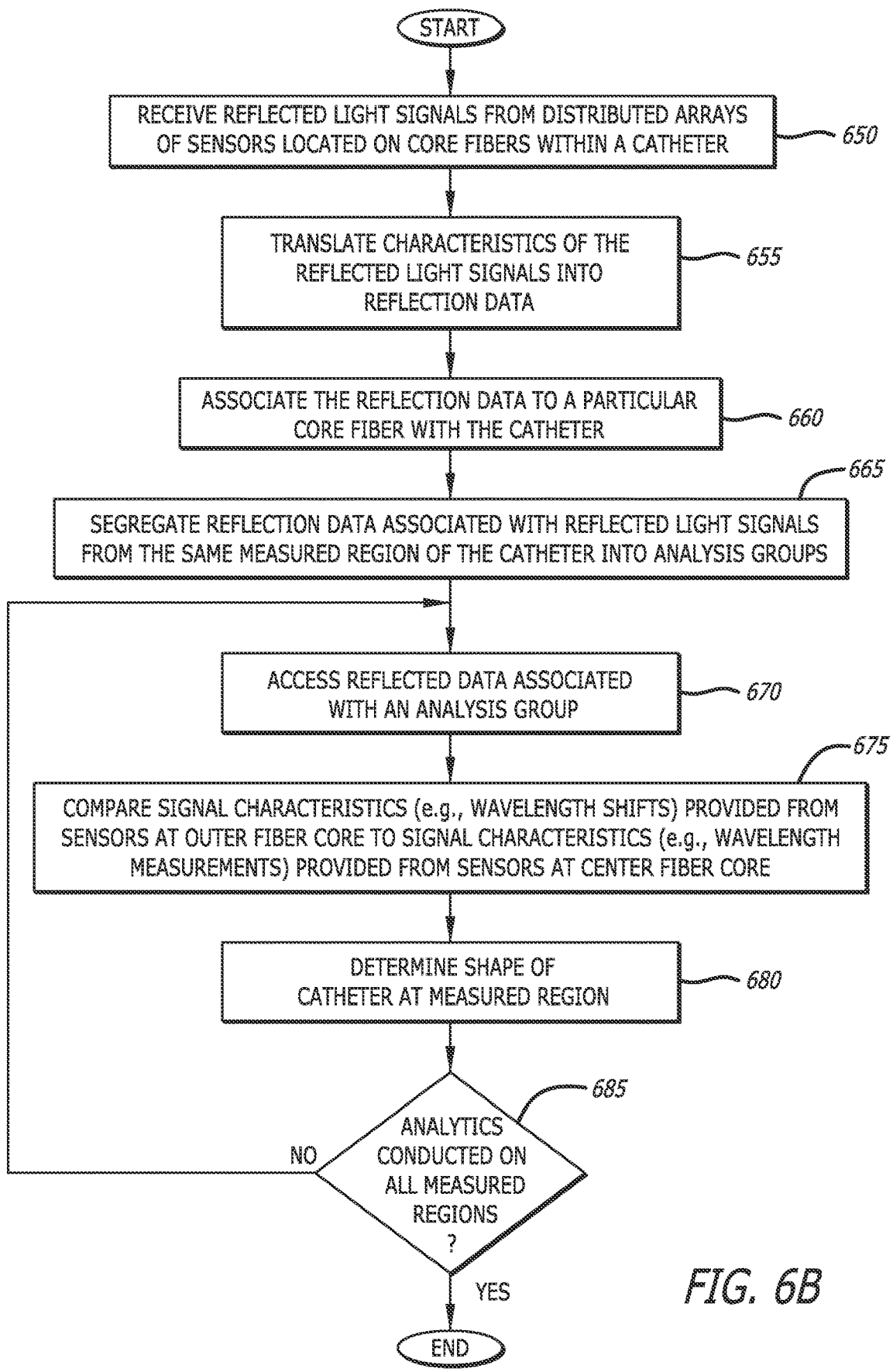

Referring to FIGS. 6A-6B, flowcharts of methods of operations conducted by the medical instrument monitoring system of FIGS. 1A-1B to achieve optic 3D shape sensing are shown in accordance with some embodiments. Herein, the catheter includes at least one septum spanning across a diameter of the tubing wall and continuing longitudinally to subdivide the tubing wall. The medial portion of the septum is fabricated with a first micro-lumen, where the first micro-lumen is coaxial with the central axis of the catheter tubing. The first micro-lumen is configured to retain a center core fiber. Two or more micro-lumen, other than the first micro-lumen, are positioned at different locations circumferentially spaced along the wall of the catheter tubing. For example, two or more of the second plurality of micro-lumens may be positioned at different quadrants along the circumference of the catheter wall.

Furthermore, each core fiber includes a plurality of sensors spatially distributed along its length between at least the proximal and distal ends of the catheter tubing. This array of sensors is distributed to position sensors at different regions of the core fiber to enable distributed measurements of strain throughout the entire length or a selected portion of the catheter tubing. These distributed measurements may be conveyed through reflected light of different spectral widths (e.g., specific wavelength or specific wavelength ranges) that undergoes certain wavelength shifts based on the type and degree of strain.

According to one embodiment of the disclosure, as shown in FIG. 6A, for each core fiber, broadband incident light is supplied to propagate through a particular core fiber (block 600). Unless discharged, upon the incident light reaching a sensor of a distributed array of sensors measuring strain on a particular core fiber, light of a prescribed spectral width associated with the first sensor is to be reflected back to an optical receiver within a console (blocks 605-610). Herein, the sensor alters characteristics of the reflected light signal to identify the type and degree of strain on the particular core fiber as measured by the first sensor (blocks 615-620). According to one embodiment of the disclosure, the alteration in characteristics of the reflected light signal may signify a change (shift) in the wavelength of the reflected light signal from the wavelength of the incident light signal associated with the prescribed spectral width. The sensor returns the reflected light signal over the core fiber and the remaining spectrum of the incident light continues propagation through the core fiber toward a distal end of the catheter tubing (blocks 625-630). The remaining spectrum of the incident light may encounter other sensors of the distributed array of sensors, where each of these sensors would operate as set forth in blocks 605-630 until the last sensor of the distributed array of sensors returns the reflected light signal associated with its assigned spectral width and the remaining spectrum is discharged as illumination.

Referring now to FIG. 6B, during operation, multiple reflected light signals are returned to the console from each of the plurality of core fibers residing within the corresponding plurality of micro-lumens formed within a catheter, such as the catheter of FIG. 1B. In particular, the optical receiver receives reflected light signals from the distributed arrays of sensors located on the center core fiber and the outer core fibers and translates the reflected light signals into reflection data, namely electrical signals representative of the reflected light signals including wavelength shifts caused by strain (blocks 650-655). The reflection data classification logic is configured to identify which core fibers pertain to which reflection data and segregate reflection data provided from reflected light signals pertaining to a particular measurement region (or similar spectral width) into analysis groups (block 660-665).

Each analysis group of reflection data is provided to shape sensing logic for analytics (block 670). Herein, the shape sensing logic compares wavelength shifts at each outer core fiber with the wavelength shift at the center core fiber positioned along central axis and operating as a neutral axis of bending (block 675). From these analytics, on all analytic groups (e.g., reflected light signals from sensors in all or most of the core fibers), the shape sensing logic may determine the shape the core fibers have taken in three-dimensional space, from which the shape sensing logic can determine the current physical state of the catheter in three-dimension space (blocks 680-685).

Figure 7:
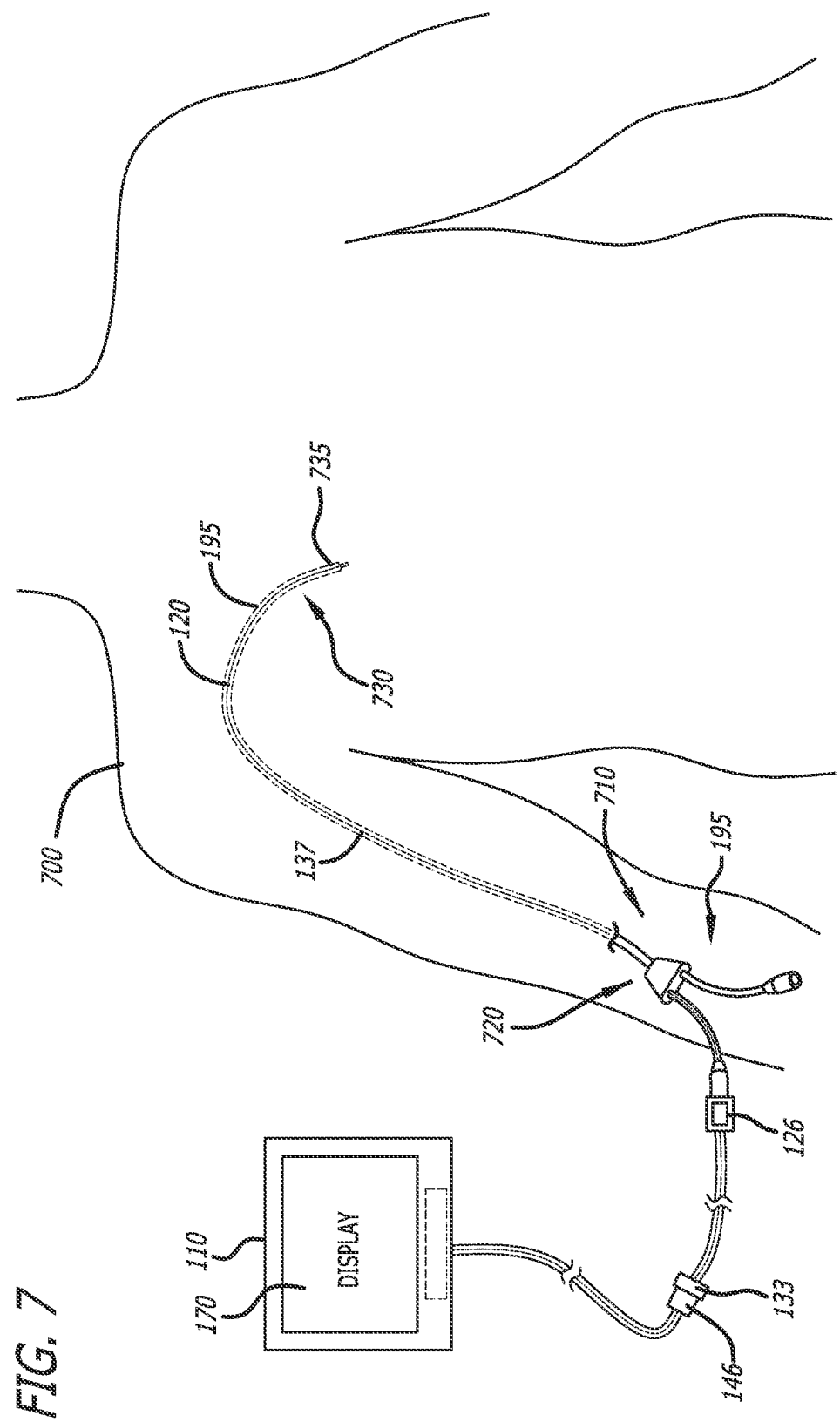
FIG. 7 is an exemplary embodiment of the medical instrument monitoring system of FIG. 1A during operation and insertion of the catheter into a patient in accordance with some embodiments.

Referring to FIG. 7, an exemplary embodiment of the medical instrument monitoring system of FIG. 1A during operation and insertion of the catheter into a patient are shown in accordance with some embodiments. Herein, the catheter 195 generally includes integrated tubing with a proximal portion 720 that generally remains exterior to the patient 700 and a distal portion 730 that generally resides within the patient vasculature after placement is complete, where the catheter 195 enters the vasculature at insertion site 710. The stylet 120 may be advanced through the catheter 195 to a desired position within the patient vasculature such that a distal end (or tip) 735 of the stylet 120 (and hence a distal end of the catheter 195) is proximate the patient's heart, such as in the lower one-third (⅓) portion of the Superior Vena Cava ("SVC") for example. For this embodiment, various instruments may be placed at the distal end 735 of the stylet 120 and/or the catheter 195 to measure pressure of blood in a certain heart chamber and in the blood vessels, view an interior of blood vessels, or the like.

The console connector 133 enables the stylet 120 to be operably connected to the console 110 via the interconnect 145 (FIG. 1A). Herein, the connector 146 is configured to engage (mate) with the console connector 133 to allow for the propagation of light between the console 110 and the stylet assembly 119 (particularly the stylet 120) as well as the propagation of electrical signals from the stylet 120 to the console 110

During advancement of the stylet 120, the distal tip 735 typically fluctuates due to, among other factors, blood flow and blood pressure within the blood vessel. These fluctuations may be movements by a distal portion of the stylet 120 in any direction. Typically, the movements are relatively minor compared to the overall advancement of the stylet 120 (and the catheter 195); however, such movements are detectable by the sensors of the core fibers integrated into the stylet 120.

Figure 8:
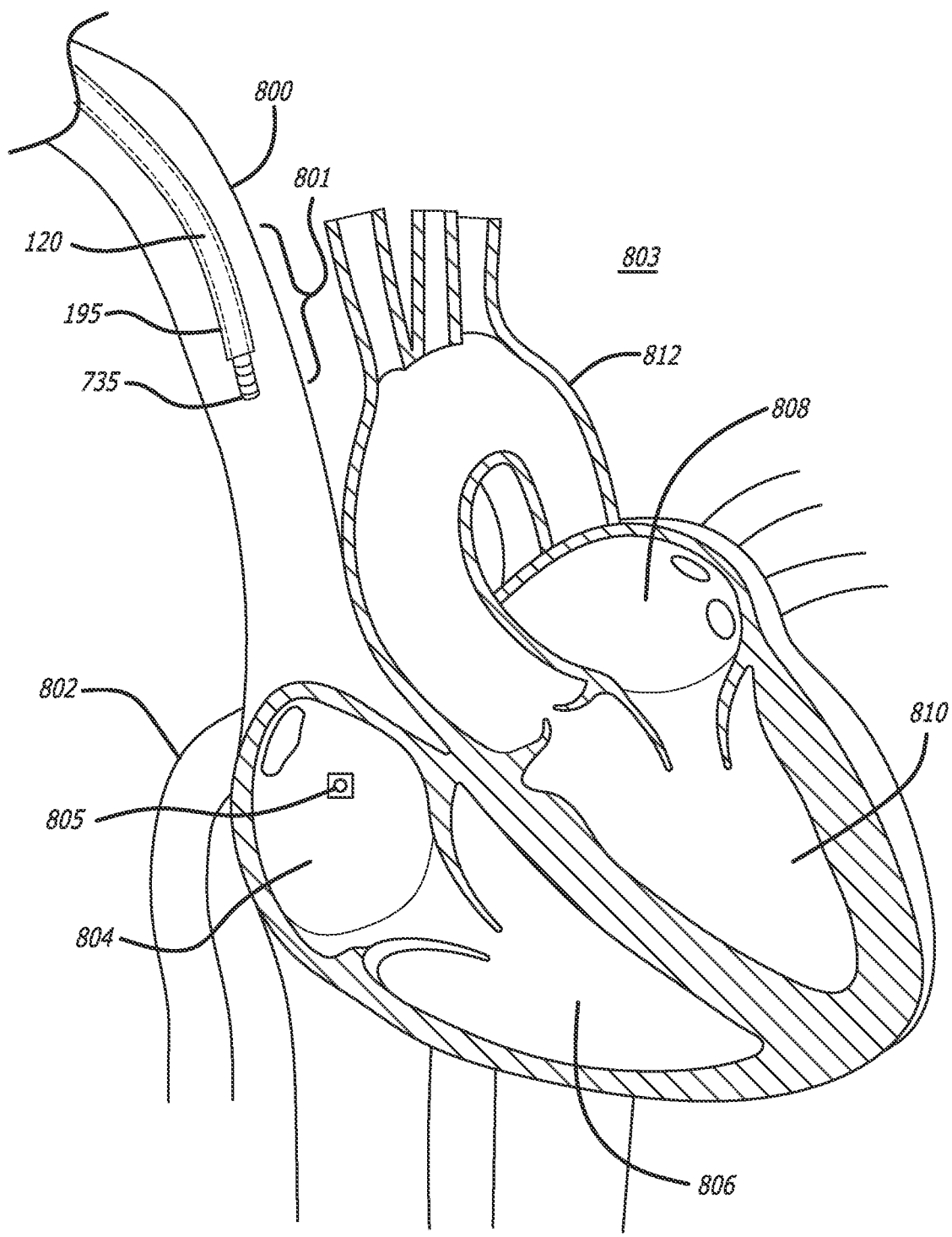
FIG. 8 is a detailed view of a stylet disposed within the Superior Vena Cava (SVC) advancing toward the right atrium of a patient in accordance with some embodiments.

The fluctuations may vary based on the blood vessel in which the stylet 120 (and catheter 195) is advancing due to one or more of the physical properties of the blood vessel, the location of the blood vessel (and its proximity to the patient's heart), and any defects affecting the blood vessel (e.g., vessel constriction, vasospasm, occlusion, etc.). As will be discussed in further detail below, the volume of the blood vessel may affect the fluctuations (e.g., a larger diameter may provide for greater fluctuation). Similarly, the turbulence of the blood flow generally affects the fluctuations (e.g., higher turbulence typically equates to greater fluctuation). Relatedly, the proximity of the distal tip 735 to the patient's heart may affect the fluctuations due to the turbulent blood flow emanating from the right atrium of the heart and flowing through the SVC (see FIG. 8). The blood pressure within the blood vessel may also affect tip fluctuations. Further, various defects may affect the fluctuations of the distal tip 735 and cause fluctuations that vary from those expected when the stylet 120 is advancing through a healthy blood vessel. FIGS. 8B-8D provide examples of the stylet 120 advancing toward various defects.

a. Fiber Optic Fluctuation Detection

Referring now to FIG. 8, a detailed view of a stylet disposed within the Superior Vena Cava (SVC) advancing toward the right atrium of a patient is shown in accordance with some embodiments. FIG. 8 illustrates a detailed perspective of the vasculature proximate to the heart 803 of a patient as well as the anatomy of the heart 803. Specifically, as the stylet 120 approaches the right atrium 804 through the SVC 800, the stylet 120 may either advance into the right atrium 804 or into the azygos vein 802. The stylet 120 is often used to locate a particular point in the vasculature at which point the catheter 195 may be used to administer a medical procedure or medicament, where this point may be referred to as the "target site" 805.

In some embodiments, the tip fluctuation logic 198 is configured to confirm the location of the distal tip 735 of the stylet 120 (which, in turn, corresponds to the distal tip of the catheter 195, within a predetermined distance such as approximately 1-2 cm) as the catheter 195 and the stylet 120 advance through a patient's vasculature toward a target site 805. According to one embodiment of the disclosure, the tip fluctuation logic 198 is configured to analyze a subset of the wavelength shifts measured by sensors deployed in each of the core fibers 137, for example, the sensors included in the distal portion 801 of the stylet 120. In some embodiments, the distal portion 801 includes a plurality of sensors such as 50, 30, 10, 5, 3, etc. It should be noted that the disclosure is not limited to the recited number of sensors and such a recitation should be understood to merely provide exemplary examples. Further, in some embodiments, the number of sensors included in the distal portion 501 and thus utilized by the tip fluctuation logic 198 may be dynamically configurable during run-time. Thus, a user may provide user input to the console 110 to adjust the number of sensors utilized by the tip fluctuation logic 198. As a result, a user may alter the specificity of the analysis performed by the tip fluctuation logic 198 during run-time (e.g., where utilization of a fewer number of sensors may correspond to an analysis that is more specific as to fluctuation at the distal tip 735).

In particular, the tip fluctuation logic 198 is configured to analyze wavelength shifts measured by the sensors of core fibers 137 located within the distal portion 801, where such corresponds to a tip fluctuation analysis as discussed above. With reference to FIG. 8, as the distal tip 735 of the stylet 120 advances through the SVC 800 toward the target site 805 within the right atrium 804, the sensors within the distal portion 801 may detect an increase in movements, corresponding to an increase in tip fluctuations. The increase in tip fluctuations may be caused by the turbulence of the blood flow exiting the SVC and entering the right atrium (thus, the stylet 120 is advancing in a direction of the blood flow). Thus, the increase in fluctuations may provide the tip fluctuation logic 198 one indication that the distal tip 735 is approaching the right atrium 804.

In one embodiment, the tip fluctuation logic 198 may be configured to correlate the wavelength shifts received from the sensors within the distal portion 801 with data from the experiential knowledge repository 193 corresponding to previously detected wavelength shifts received from sensors within a similar distal portion of a stylet. Based on the correlation, the tip fluctuation logic 198 may determine the distal tip 735 is within the SVC 800, within a certain distance to the right atrium 804 or the target site 805, or within the right atrium 804. In one instance, the determination may be based on whether the correlation results indicate that the correlation between the detected wavelength shifts and any of the previously detected wavelength shifts corresponding to the SVC 800, the target site 805 or the right atrium 804 is greater than or equal to a threshold.

In other embodiments, the detected wavelength shifts received from the sensors within the distal portion 801 may be utilized by the tip fluctuation logic 198 as input to a trained machine-learning model that, upon processing, provides a correlation to one or more of previously detected fluctuations corresponding to the SVC 800, the target site 805 or the right atrium 804. A similar threshold determination may then be made by the tip fluctuation logic 198 as referenced above.

In embodiments in which ECG signals may be obtained by the stylet 120 (or the catheter 195), the ECG signals may provide an indication as to the rhythmic pulses of the heart 803. The tip fluctuation logic 198 may compare the rhythmic pulses as indicated by the ECG signals to the detected wavelength shifts received from the sensors within the distal portion 801 to determine whether the detected wavelength shifts indicate movement that correlates to the rhythmic pulses by at least a threshold.

In some embodiments, the tip confirmation may be used in combination with the shape sensing functionality discussed above in which the shape sensing logic 194 determines the current physical state of the stylet 120 (and hence the catheter 195) in 3D space for rendering on the display 170. Further, in some embodiments, the catheter 195 and/or the stylet 120 may incorporate a pressure sensor configured to detect the blood pressure within the blood vessel (or heart chamber) in which the distal tip 735 is placed. The detected blood pressure may also be utilized in the correlations discussed herein such that the tip fluctuation logic 198 may correlate the detected blood pressure with previously detected blood pressures to aid in the determination of the placement of the distal tip 735 and/or detection of a defect affecting the blood vessel.

As one example, the tip fluctuation logic 198 may detect, or provide data for detection of, placement of the distal tip 735 in the Azygos vein 802. For instance, the tip fluctuation logic 198 may detect fluctuations correlating to placement within the SVC 800 and subsequently detect a decrease in fluctuations such that the detected fluctuations no longer correlate to placement with the SVC 800 but instead correlate to placement within the Azygos vein 802. For example, upon detection of a decrease in fluctuations, the tip fluctuation logic 198 may perform a correlation between the detected fluctuations and previously detected fluctuations known to correspond to the Azygos vein. The decrease in fluctuations of the distal tip 735 within the Azygos vein compared to the within the SVC 800 may be due to the smaller diameter of the Azygos vein 802, and less turbulent blood flow within the Azygos vein 802.

This detection may be optionally confirmed through detection of the direction of blood flow as well as ECG imaging, magnetic/electromagnetic signature tracking and/or impedance/conductance measuring, as discussed below. As one example of a confirmation operation performed by the confirmation logic 199, when the distal tip 735 of the stylet 120 advances into the Azygos vein 802 and such is detected through analysis of the reflected light signals by the shape sensing logic 194, the confirmation logic 199 may obtain measurement data indicating the direction of the blood flow with respect to the advancement of the distal tip 735. The confirmation logic 199 may then compare the direction of the blood flow with the expected direction of blood flow within the Azygos vein 802 (which is the placement of the distal tip 735 as determined by the shape sensing logic 194. When the expected direction of blood flow matches the detected direction of blood flow, the confirmation logic 199 confirms the placement of the distal tip 735 as determined through analysis of the reflected light signals.

In some embodiments, the tip fluctuation logic 198 may generate a graphic illustrating the detected tip fluctuation compared to previously detected tip fluctuations and/or the rhythmic impulses of the heart. In one embodiment, such a graphic may include a dynamic visualization of the present distal tip moving in accordance with the detected tip fluctuations adjacent to a distal tip moving in accordance with previously detected tip fluctuations.

As will be discussed below, systems, methods, and apparatuses of the disclosure may utilize the tip fluctuation data as detected through analyses of the reflected light signals in a confirmation process that includes operations of confirming a placement of the distal tip 735 through comparison with measurements (e.g., tip fluctuations) obtained through other modalities such as magnetic/electromagnetic signature tracking and/or internal impedance/conductance measurements.

II. Magnetic/Electromagnetic Fluctuation Detection

Figure 9:
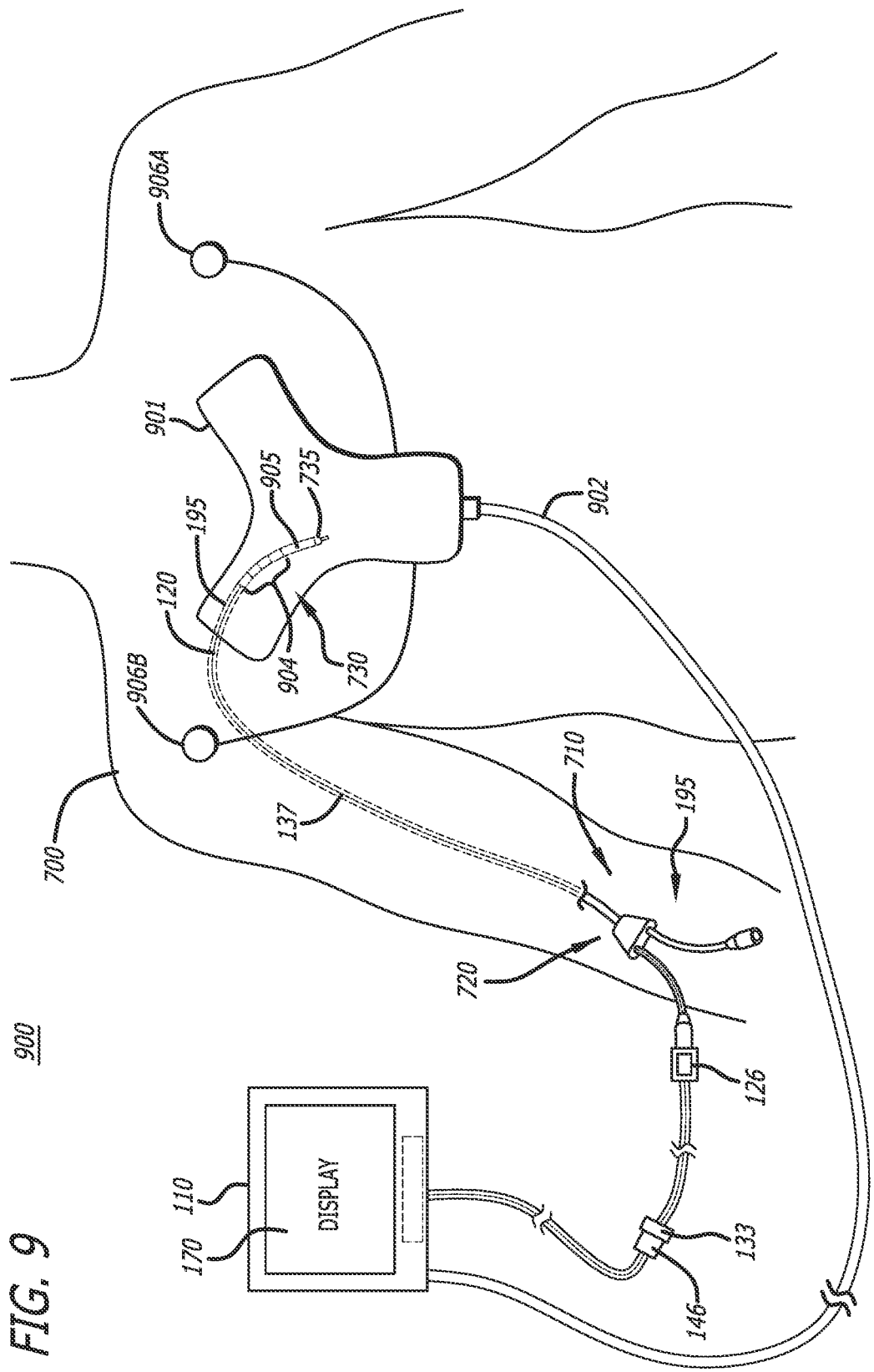
FIG. 9 is an exemplary embodiment of the medical instrument monitoring system of FIG. 1A modified to include a magnetic assembly for the magnetically-based modality and an ECG sensor assembly for sensing ECG signals produced by the SA node during operation and insertion of the medical instrument into a patient in accordance with some embodiments.

Referring to now FIG. 9, an exemplary embodiment of the medical instrument monitoring system of FIG. 1A modified to include a magnetic assembly for the magnetically-based TLS modality and an ECG sensor assembly for sensing ECG signals produced by the SA node during operation and insertion of the medical instrument into a patient is shown in accordance with some embodiments, which is referred to the medical instrument monitoring system 900. The components provided in the system 900 have the same or similar functionalities as discussed with respect to the system 100 unless otherwise described below. For instance, the stylet 120 in the 900 may include additional features and functionalities as the stylet 120 as discussed with respect to the system 100.

In this embodiment, the stylet 120, in addition to including a magnetic assembly 904 for the magnetically-based TLS modality, includes an ECG sensor assembly 905 proximate its distal end and including a portion that is co-terminal with the distal end of the catheter tip for sensing ECG signals produced by the SA node. In contrast to the previous embodiment, the stylet 120 is operably connected to the console 110 and configured to permit ECG signals detected by the ECG sensor assembly included on a distal portion of the stylet 120 to be conveyed to the console 110 during confirmation of the catheter tip location as part of the ECG signal-based tip confirmation modality. For instance, a portion of the stylet 120 (such as a casing or core wire) may be configured to provide a conductive pathway from the distal portion of the stylet 120 to the console 110.

Reference and ground ECG lead/electrode pairs 906A-906B attach to the body of the patient 700 and are operably attached to the TLS sensor 901 to enable the filtering out of high-level electrical activity unrelated to the electrical activity of the SA node of the heart, thus enabling the ECG-based tip confirmation functionality. Together with the reference and ground signals received from the ECG lead/electrode pairs 606A-906B placed on the patient's skin, the ECG signals sensed by the ECG sensor assembly of the stylet 120 are received by the TLS sensor 901 positioned on the chest of the patient 700. The processor 160 of the console 110 can process the ECG signal data to produce an electrocardiogram waveform on the display 170. In an alternative embodiment, the stylet 120 may be tethered to the TLS sensor 901, where an illustrative example of such is illustrated in U.S. Pat. No. 8,388,541, the entire contents of which are incorporated by reference herein.

Figure 10A:
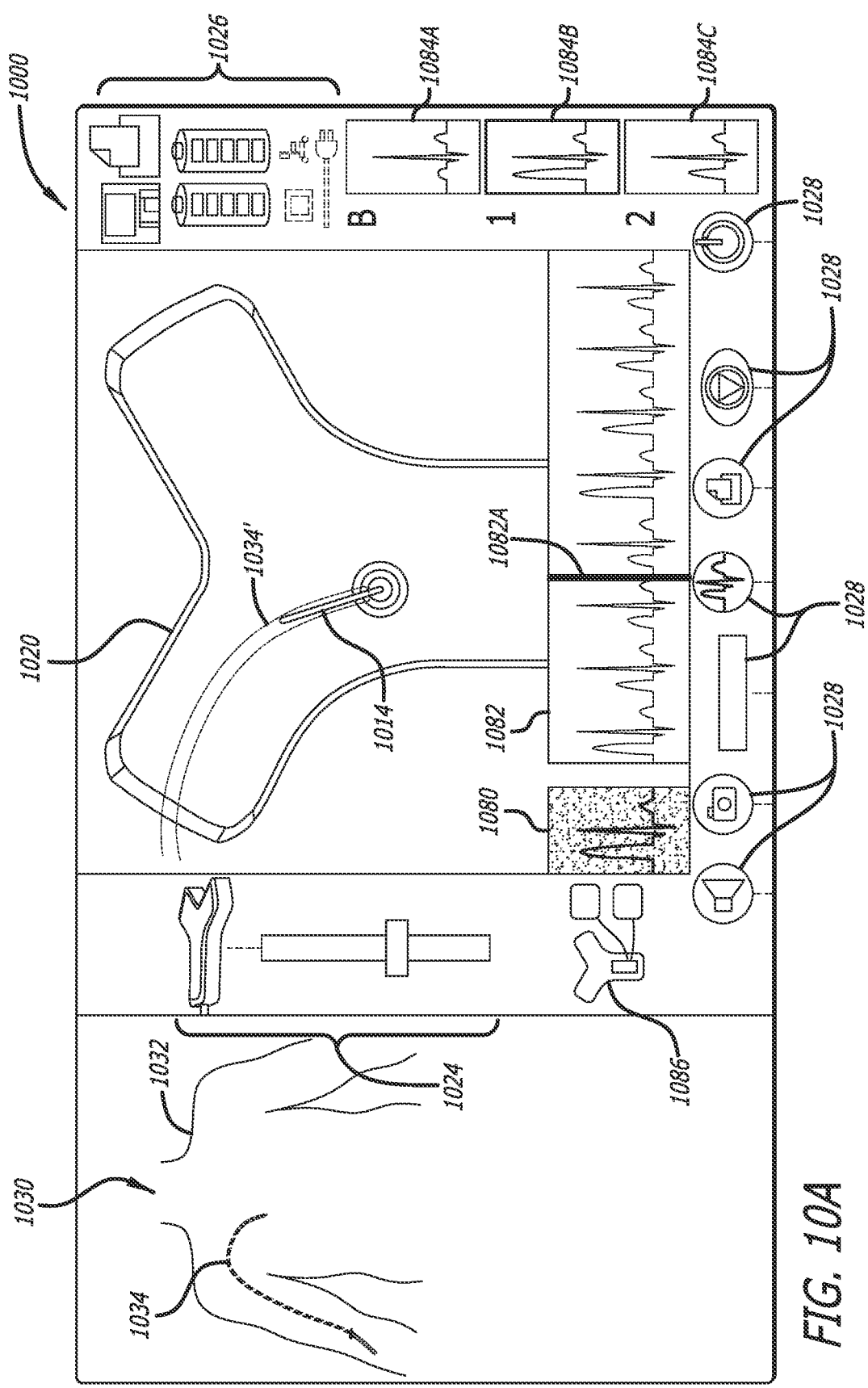
FIG. 10A is an illustrative display depicted on a display screen of a console during medical instrument placement within a patient in accordance with some embodiments.

Thus, as it is advanced through the patient vasculature, the stylet 120 may advance under the TLS sensor 901, which is positioned on the chest of the patient 700, where the TLS sensor 901 is configured to detect the position of the magnetic assembly of the stylet 120, which is substantially co-terminal with the distal tip of the catheter 195. The detection by the TLS sensor 901 of the stylet magnetic assembly 904 is depicted on the display 170 during ECG mode (FIG. 10A). The display 110 further depicts, during ECG mode, an ECG electrocardiogram waveform produced as a result of patient heart's electrical activity as detected by the ECG sensor assembly of the stylet 120. In greater detail, the ECG electrical activity of the SA node, including the P-wave of the waveform, is detected by the ECG sensor assembly of the stylet and forwarded to the console 110. The ECG electrical activity is then processed for depiction on the display 170 and a clinician placing the catheter 195 can then observe the ECG data to determine placement of the distal tip 735 of the stylet 120 (which is substantially co-terminal with the distal tip of the catheter 195), such as proximate the SA node in one embodiment. In one embodiment, the console 110 which includes the electronic components, such as the processor 160, necessary to receive and process the signals detected by the stylet ECG sensor assembly 905 (FIGS. 10B-10F). The stylet ECG sensor assembly 905 includes at least the distal end of the core wire 1038 and the conductive material 1042, where the core wire 1038 may run the length of the stylet 120 and communicatively couple to the console 110. The core wire 1038 may be stainless steel or a memory material such as, in one embodiment, a nickel and titanium-containing alloy commonly known by the acronym "nitinol."

In one embodiment, once the catheter 195 has been introduced into the patient vasculature via the insertion site 710, the TLS mode of the system 900 can be employed to advance the catheter 195 and stylet 120 toward an intended destination, e.g., proximate the SA node. Upon approaching the region of the heart, the system 900 can be switched to ECG mode to enable ECG signals emitted by the SA node to be detected. As the stylet-loaded catheter 195 is advanced toward the heart of the patient 700, the electrically conductive ECG sensor assembly 905, including the distal end of the core wire 1038 and the conductive material 1042, begins to detect the electrical impulses produced by the SA node. As such, the ECG sensor assembly 905 serves as an electrode for detecting the ECG signals. The elongate core wire 1038 proximal to the core wire distal end serves as a conductive pathway to convey the electrical impulses produced by the SA node and received by the ECG sensor assembly 905, which is then conveyed to the console 110.

The ECG signal can then be processed and depicted on the system display 170 and monitored by a clinician. When the received ECG signal matches a desired profile, the clinician can determine that the catheter distal tip (substantially co-terminal to the distal tip 735 of the stylet 120) has reached a desired position with respect to the SA node. As mentioned, in one embodiment, this desired position lies within the lower one-third (⅓rd) portion of the SVC.

The ECG sensor assembly 905 and magnetic assembly 904 are configured to work in concert in assisting a clinician in placing a catheter 195 within the vasculature. Generally, the magnetic assembly 904 of the stylet 120 assists the clinician in generally navigating the vasculature from initial insertion so as to place the distal end of the catheter 195 in the general region of the heart. The ECG sensor assembly 905 can then be employed to guide the distal end of the catheter 195 (via the stylet 120) to the desired location within the SVC by enabling the clinician to observe changes in the ECG signals produced by the heart as the ECG sensor assembly 905 approaches the SA node.

Once the stylet 120 (and catheter 195) have been positioned as desired, the catheter 195 may be secured in place and the stylet 120 removed from the catheter 195. It is noted here that the stylet 120 may include one of a variety of configurations in addition to what is explicitly described herein. In one embodiment, the stylet 120 may attach directly to the TLS sensor instead of a direct attachment to the console 110.

Referring to FIG. 10A, an illustrative display depicted on a display screen of a console during medical instrument placement within a patient is shown in accordance with some embodiments. The screenshot 1000 displays aspects of ECG signal data on the display 160 when the system 900 is in ECG mode. The screenshot 1000 includes elements of the TLS modality, including a representative image 1020 of the TLS sensor 901, and can the icon 1014 corresponding to the position of the distal tip 735 of the stylet 120 during transit through the patient vasculature. The screenshot 1000 further includes a window 1080 in which the current ECG waveform captured by the ECG sensor assembly of the stylet 120 and processed by the system 900 is displayed. The window 1080 is continually refreshed as new waveforms are detected.

Window 1082 includes a successive depiction of the most recent detected ECG waveforms, and includes a refresh bar 1082A, which moves laterally to refresh the waveforms as they are detected. Window 1084A is used to display a baseline ECG waveform, captured before the ECG sensor assembly 905 is brought into proximity with the SA node, for comparison purposes to assist the clinician in determining when the desired catheter tip location has been achieved. Windows 1084B and 1084C can be filed by user-selected detected ECG waveforms (e.g., when the user pushes a predetermined button on a probe, not shown, or the console 110). The waveforms in the windows 1084B and 1084C remain until overwritten by new waveforms as a result of user selection via button pushes or other input. The depth scale 1024, status/action indicia 1026, and button icons 1028 are included on the display 170. An integrity indicator 1086 is also included on the display 170 to give an indication of whether the ECG lead/electrode pairs 906A-906B are operably connected to the TLS sensor 901.

The display 170 may be configured to depict elements of the TLS, ECG, and fiber optic modalities simultaneously on a single screen, thus offering the clinician ample data to assist in placing the catheter distal tip in a desired position. For instance, the display portion 1030 includes an image of a representative patient 1032 (which may be customized based on particularized input that corresponds to a patient (e.g., male, female, height, body measurements, etc.) and an image 1034 of the stylet 120 (and/or the catheter 195) within the patient vasculature. Note further that in one embodiment a printout of the screenshot or selected ECG, TLS, or fiber optic data can be saved, printed, or otherwise preserved by the system 900 to enable documentation of proper catheter placement. Additionally, an optional image 1034' may be included as an overlay or underlay to the image 1020 such that a clinician may visualize the location data for the fiber optic and TLS modalities together to confirm data from the two modalities correspond to one another.

Figure 10B:
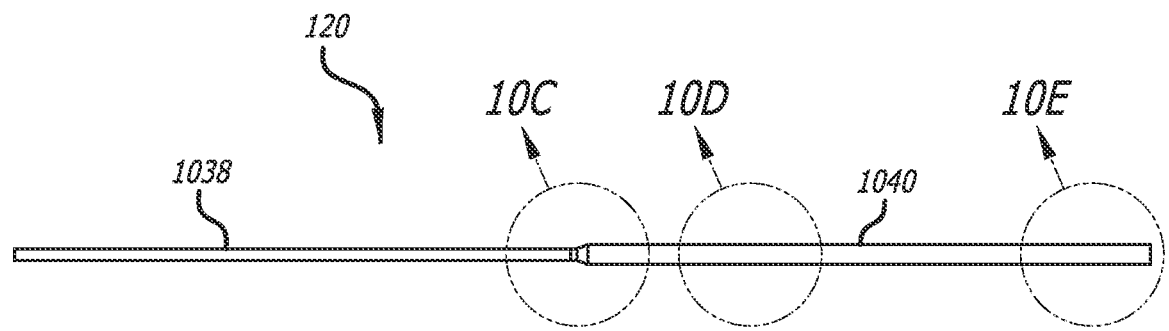
FIGS. 10B-10F are illustrative various views of portions of the an exemplary medical instrument deployed by the medical instrument monitoring system of FIG. 9 in accordance with some embodiments.
Figure 10C:
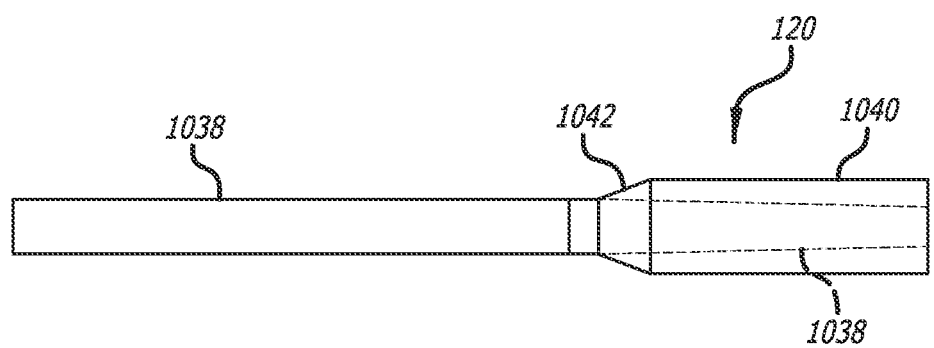
Figure 10D:
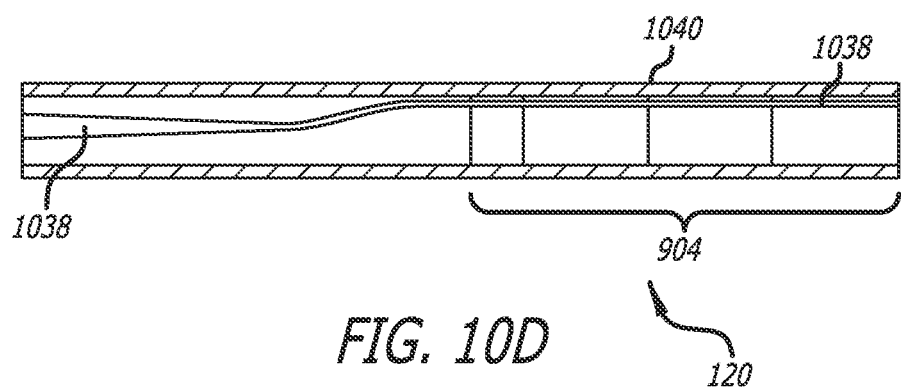
Figure 10E:
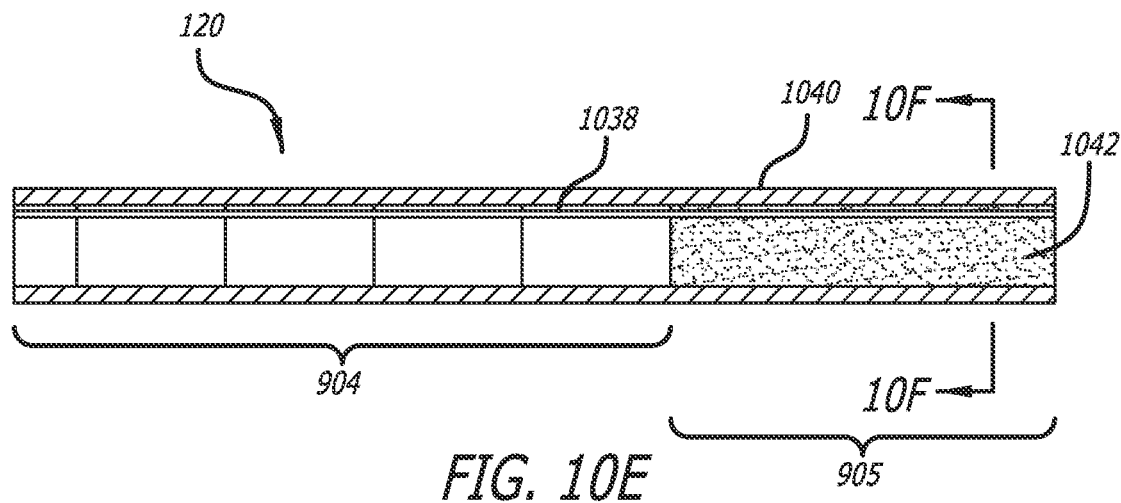

Referring now to FIGS. 10B-10F, illustrative various views of portions of an exemplary medical instrument deployed by the medical instrument monitoring system of FIG. 9 are shown in accordance with some embodiments. As seen in FIGS. 10B-10C, a distal portion of the core wire 1038 is gradually tapered, or reduced in diameter, distally from a junction point 1042. A sleeve 1040 is slid over the reduced-diameter core wire portion. Though of relatively greater diameter here, the sleeve in another embodiment can be sized to substantially match the diameter of the proximal portion of the stylet core wire. The stylet 120 further includes a magnetic assembly disposed proximate the distal end of the stylet 120 thereof for use during TLS mode. The magnetic assembly in the illustrated embodiment includes a plurality of magnetic elements 904 interposed between an outer surface of the reduced-diameter core wire 1038 and an inner surface of the sleeve 1040 proximate the distal tip 735 of the stylet 120. In the present embodiment, the magnetic elements 904 include 20 ferromagnetic magnets of a solid cylindrical shape stacked end-to-end in a manner. In other embodiments, however, the magnetic element(s) may vary from this design in not only shape, but also composition, number, size, magnetic type, and position in the stylet. For example, in one embodiment the plurality of magnets of the magnetic assembly is replaced with an electromagnetic coil that produces a magnetic field for detection by the TLS sensor. These and other variations are therefore contemplated by embodiments of the present invention.

The magnetic elements 904 are employed in the stylet 120 distal portion 730 to enable the position of the distal tip 735 to be observable relative to the TLS sensor 901 placed on the chest of the patient 700. As has been mentioned, the TLS sensor 901 is configured to detect the magnetic field of the magnetic elements 904 as the stylet 120 advances with the catheter 195 through the patient vasculature. In this way, a clinician placing the catheter 195 is able to generally determine the location of the distal end of the catheter 195 within the patient vasculature and detect when catheter malposition is occurring, such as advancement of the catheter 195 along an undesired vein, for instance.

The stylet 120 further includes the afore-mentioned ECG sensor assembly 905, according to one embodiment. The ECG sensor assembly 905 enables the stylet 120, disposed in a lumen of the catheter 195 during insertion, to be employed in detecting an intra-atrial ECG signal produced by an SA or other node of the patient's heart, thereby allowing for navigation of the distal tip of the catheter 195 to a predetermined location within the vasculature proximate the patient's heart. Thus, the ECG sensor assembly serves as an aide in confirming proper placement of the catheter distal tip.

Figure 10F:
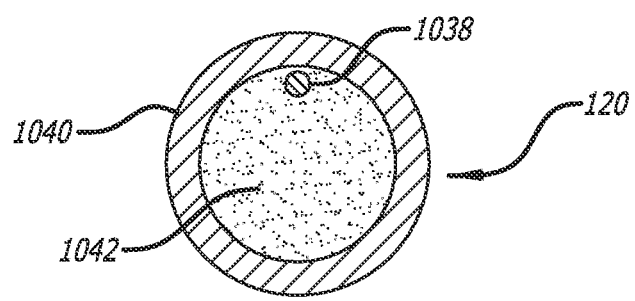

In the embodiment illustrated in FIGS. 9-10F, the ECG sensor assembly includes a distal portion of the core wire 1038 disposed proximate the stylet distal end. The core wire 1038, being electrically conductive, enables ECG signals to be detected by the distal end thereof and transmitted proximally along the core wire 1038. A conductive material 1046, such as a conductive epoxy, fills a distal portion of the sleeve 1040 adjacent the distal termination of the core wire 1038 so as to be in conductive communication with the distal end of the core wire 1038. This in turn increases the conductive surface of the distal end of the stylet 120 so as to improve its ability to detect ECG signals.

Before catheter placement, the stylet 120 is loaded into a lumen of the catheter 195. Note that the stylet 120 can come preloaded in the catheter lumen from the manufacturer, or loaded into the catheter by the clinician prior to catheter insertion. The stylet 120 is disposed within the catheter lumen such that the distal end of the stylet 120 is substantially co-terminal with the distal tip of the catheter 195, thus placing the distal tips of both the stylet 120 and the catheter 195 in substantial alignment with one another. The co-terminality of the catheter 195 and stylet 120 enables the magnetic assembly to function with the TLS sensor 901 in TLS mode to track the position of the catheter distal tip as it advances within the patient vasculature, as has been described. Note, however, that for the tip confirmation functionality of the system 900, the distal end of the stylet 120 need not be co-terminal with the catheter distal end. Rather, all that is required is that a conductive path between the vasculature and the ECG sensor assembly, in this case the core wire 1038, be established such that electrical impulses of the SA node or other node of the patient's heart can be detected. This conductive path in one embodiment can include various components including saline solution, blood, etc.

In one embodiment, once the catheter 195 has been introduced into the patient vasculature via the insertion site 710 (FIG. 9) the TLS mode of the system 900 can be employed as already described to advance the catheter distal tip toward its intended destination proximate the SA node. Upon approaching the region of the heart, the system 900 can be switched to ECG mode to enable ECG signals emitted by the SA node to be detected as discussed above.

As discussed above, the system 900 provides multiple modalities that provide data indicative of a location of a tip of a medical instrument. Namely, the system 900 provides a fiber optic modality providing fiber optic shape sensing capabilities, a magnetically based TLS modality that provides location information through tracking of a plurality of magnets or an electromagnetic coil disposed at the distal end of the medical instrument, and an ECG modality that provides location information through detection of electrical impulses emitted by the SA node by conductive material disposed near the distal end of the medical instrument. Thus, the system 900 may utilize the information obtained from two or more modalities to confirm a determined or detected location of the distal tip 735 of the stylet (which is substantially co-terminal with the distal tip of the catheter 195).

In one embodiment, the fiber optic modality may be used to determine a location of the distal tip 735 of the stylet 120 based on operations based by the shape sensing logic 194 as discussed above. The determined location may then be confirmed through the detection of fluctuations of the distal tip 735 by gratings disposed at the distal portion 730 of the stylet 120, where the detected fluctuations are be compared to stored (historical) fluctuation data for the determined location and confirmation occurs when the detected fluctuations have a profile that corresponds to a stored profile of detected fluctuations for the determined location. The correspondence may refer to a similarity between the two profiles within a threshold (e.g., 80% correspondence, 90% correspondence, etc.). In one embodiment, a profile may refer to fluctuations per second (or other time period) and/or a magnitude of fluctuation (e.g., movement in different directions).

Additionally, or in the alternative, the location as determined by the fiber optic modality via operations of the shape sensing logic 194 may be confirmed in a similar manner using the data obtained by the TLS modality and/or the ECG modality. For instance, as seen in FIG. 10A, a graphical depiction of the TLS modality data and the fiber optic shape sensing data may be depicted to enable a clinician to visualize whether the data from the two modalities correspond to the same or substantially the same location for the distal tip of the stylet 120. Additionally, fluctuations of the distal tip detected by the magnetic assembly 904 detected may be compared to stored (historical) fluctuation data for the determined location (e.g., as previously obtained by via a TLS modality) to determine whether the two correspond to the same or substantially the same location (e.g., within a threshold distance) based on a similarity of the fluctuation profiles as referenced above. When the profiles are the same or substantially the same (e.g., 80% similarity, 90% similarity, etc.), the TLS modality data is determined to confirm the location as determined by the fiber optic modality.

In a similar manner, stored ECG data for the determined location may be compared to detected ECG data and when the two ECG data are the same or substantially the same (e.g., 80% similarity, 90% similarity, etc.), the ECG data is determined to confirm the location as determined by the fiber optic modality.

In other embodiments, a location of the distal tip may be determined by selecting the location that was determined by a majority (or other threshold number or percentage) of the modalities. In another embodiment, each modality may be associated with a predetermined weight (e.g., provided by an expert, such as a medical professional) where the location of the distal tip is determined by a weighted sum of each location determined by the modalities such that the location having the greatest weight is determined to be the location of the distal tip. In some instances, the determined location must meet or exceed a confidence threshold prior to being provided to a user (e.g., rendered on the display screen 170 of the console 110 or other display mechanism). Alternatively, the weights of each location determined by the modalities by be provided.

Additional descriptions of the components of the system 900 may be found in U.S. Pat. No. 8,388,541, the entire contents of which are incorporated by reference herein.

III. Impedance/Conductance Fluctuation Detection

Referring now to FIGS. 11A-12B, certain embodiments disclosed herein include a number of steps for localizing a junction or other structure within a body lumen, including providing an embodiment of systems 1100, 1102 as disclosed herein; introducing a catheter (and/or a catheter/stylet pairing) into the body lumen; providing electrical current flow to the body lumen through the catheter (or stylet); measuring a first conductance value at a first location in the body lumen; moving the catheter (and/or stylet) to a second location in the body lumen; measuring a second conductance value at a second location in the body lumen; and determining a profile of the body lumen based on the first conductance value of the first location and the second conductance value of the second location. The profile of the body lumen resulting from such embodiments may include relative conductances and/or relative cross-sectional areas.

For other embodiments, the actual values for the lumen conductance or cross-sectional area are determined by further injecting a known volume of a first solution having a first conductivity into the body lumen; injecting a second solution having a second conductivity into the body lumen, wherein the second solution has a second volume and wherein the second conductivity does not equal the first conductivity; measuring a second conductance value at the first location in the body lumen; calculating the conductance at the first location in the body lumen; measuring a first conductance value at a second location in the body lumen; and calculating the conductance at the second location in the body lumen. The determination of the profile of the body lumen may be based on the conductance of the first location, the conductance of the second location, and the conductivities of the first and second solutions.

Figure 11A:
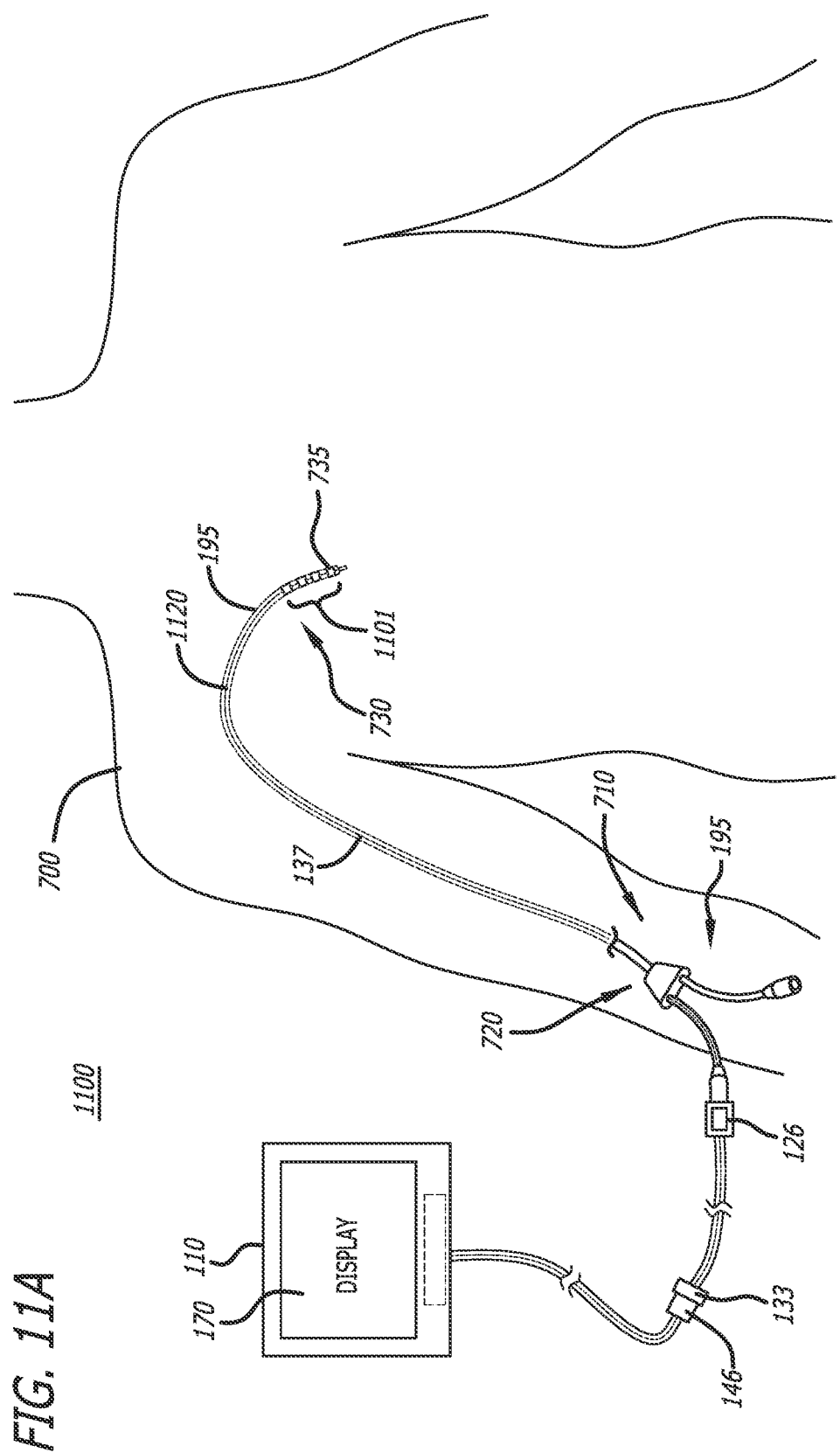
FIG. 11A is an exemplary embodiment of the medical instrument monitoring system of FIG. 1A modified to include a plurality of electrodes at a distal end of a stylet during operation and insertion of the catheter into a patient in accordance with some embodiments.

Referring now to FIG. 11A, an exemplary embodiment of the medical instrument monitoring system of FIG. 1A modified to include a plurality of electrodes at a distal end of a stylet during operation and insertion of the catheter into a patient is shown in accordance with some embodiment. The system 1100 illustrates a modified version of system 100 of FIG. 1A in which the stylet 1120 includes a plurality of electrodes 1101 positioned at the distal portion 730. The system 1100 is configured to operate in one or more modalities includes a fiber optic modality that operates in the manner discussed above and/or an impedance/conductance modality deploying the plurality of electrodes 1101. Additional detail as to the configuration as deployment of the plurality of electrodes 1101 is discussed below with respect to FIGS. 12A-12B.

Figure 11B:
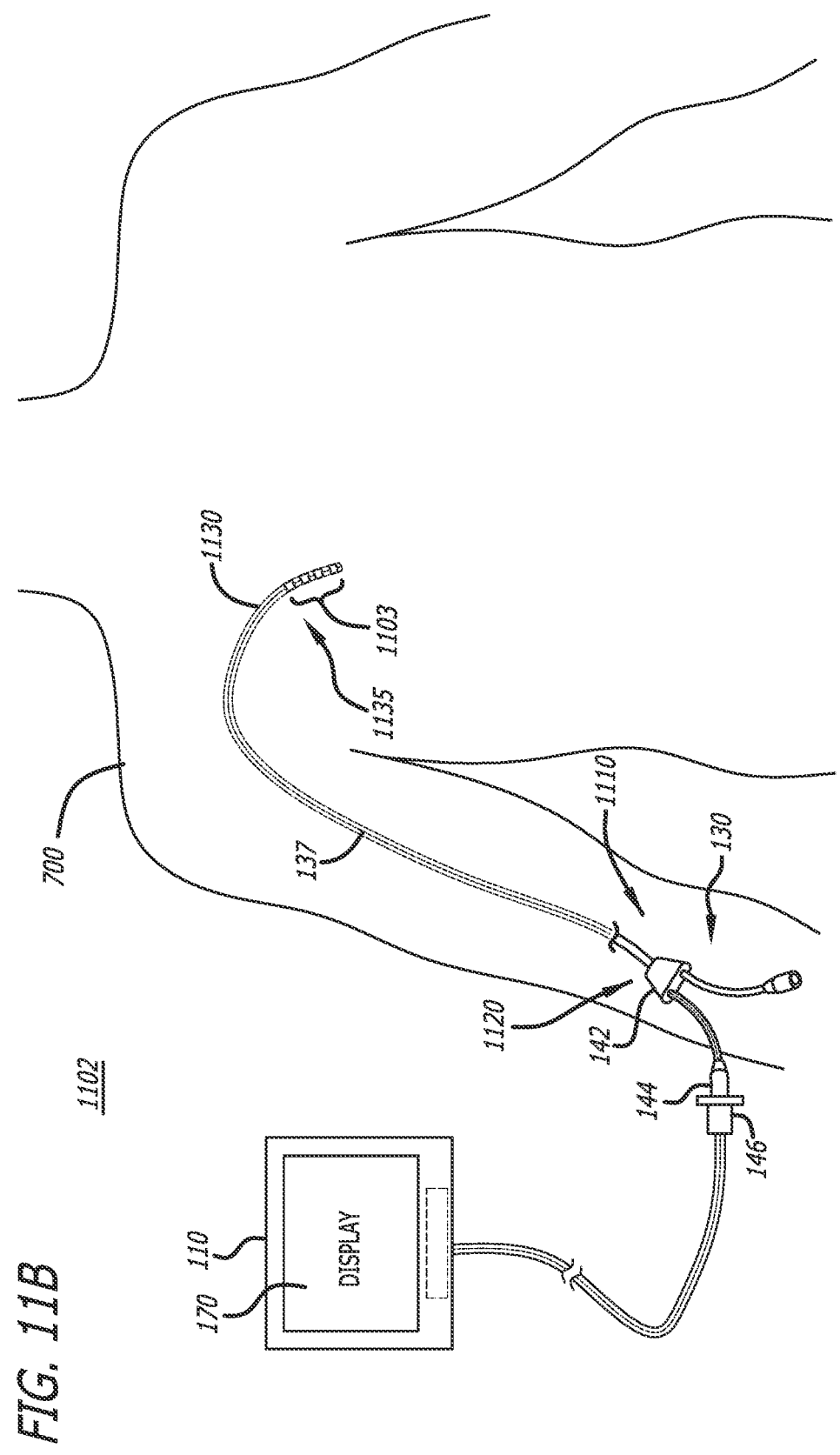
FIG. 11B is an exemplary embodiment of the medical instrument monitoring system of FIG. 1A modified to include a plurality of electrodes at a distal end of the catheter during operation and insertion of the catheter into a patient in accordance with some embodiments.

Referring now to FIG. 11B, an exemplary embodiment of the medical instrument monitoring system of FIG. 1B modified to include a plurality of electrodes at a distal end of the catheter during operation and insertion of the catheter into a patient is shown in accordance with some embodiments. The system 1102 illustrates a modified version of system 100 of FIG. 1B in which the catheter 1130 includes a plurality of electrodes 1102 positioned at the distal portion 1135. The system 1102 is configured to operate in one or more modalities includes a fiber optic modality that operates in the manner discussed above and/or an impedance/conductance modality deploying the plurality of electrodes 1103. Additional detail as to the configuration as deployment of the plurality of electrodes 1103 is discussed below with respect to FIGS. 12A-12B.

FIG. 12A shows an embodiment of a medical device for localization of a body lumen juncture is shown in accordance with some embodiments. A conductance or impedance catheter measures conductance within a body lumen using a number of electrodes. The conductance medical device 1200 is configured to localize a body lumen junction using conductance measurements, where the medical device 1200 represents either the stylet 1120 or the catheter 1130. Medical device 1200 has a proximal end 1205 and a distal end 1210, which is suitable for introduction into a body lumen. In addition, medical device 1200 includes a pair of excitation electrodes 1215 (which represent a first subset of either the electrodes 1101, 1103) and a pair of detection electrodes 1220 (which represent a second subset of either the electrodes 1101, 1103). Each of excitation electrodes 1215 and detection electrodes 1220 has a proximal end that is capable of attachment to a processing system (e.g., the console 110) and a distal end that is located on medical device 1200 between proximal end 1205 and distal end 1210. The distal ends of detection electrodes 1220 are located on medical device 1200 between the distal ends of excitation electrodes 1215. Excitation electrodes 1215 are configured to emit a measured electrical charge into the body lumen, while detection electrodes 1220 detect the amount of the charge that travels through a fluid within the body lumen. The processing system calculates the change in electrical charge to determine the conductance through the lumen at any given location in the lumen.

As shown in FIG. 12A, electrodes 1215 and 1220 are located at distal end 1210 of medical device 1200. However, the positioning of the electrodes is not limited to this distal end portion but may be anywhere on the catheter that can assist in providing conductance information to the clinician. Furthermore, multiple sets of electrodes (not shown) may also be used to provide additional information used for mapping the interior anatomical structure of an internal organ, vessel, or other body lumen.

Referring now to FIG. 12B, a second embodiment of a medical device for localization of a body lumen juncture is shown in accordance with some embodiments. As discussed above, the embodiment of FIG. 12A includes at least two detection electrodes and two excitation electrodes. However, in the embodiment shown in FIG. 12B, only two electrodes are used (at least two electrodes to an electrode set, where multiple sets may be used as discussed above). Catheter 1225 has a proximal end 1230 and a distal end 1235, as well as a first electrode 1240 and a second electrode 1245. Each of electrodes 1240 and 1245 has a proximal end (not shown) and a distal end located on catheter 1225 between proximal end 1230 and distal end 1235. Because catheter 1225 has only two electrodes, each electrode must serve both the excitation function and the detection function. To enable a single electrode to send and measure the electric charge, a delay must be added to the circuit. Additionally, a bipolar catheter must be stationary at the time of measurement, requiring the clinician to obtain a profile by moving the catheter to a desired location, stopping and taking a measurement, and then moving the catheter again. By contrast, tetrapolar catheters may take a continuous conductance measurement as the catheter is pulled or pushed through the body lumen, thereby giving a more detailed profile as compared to bipolar catheters.

Although at least some embodiments can properly measure lumen conductance in the presence of a bodily fluid (such as blood) within the lumen, certain other embodiments may use fluids injected into the body lumen to properly calculate lumen conductance and/or cross-sectional area, as explained herein. Therefore, some embodiments include a channel through which fluid is injected into the body lumen.

In one embodiment, the fiber optic modality may be used to determine a location of the distal tip 735 of the stylet 120 and the determined location may then be confirmed through the detection of fluctuations of the distal tip 735 as discussed above. Additionally, or in the alternative, the location as determined by the fiber optic modality may be confirmed using the data obtained by the conductance modality. For instance, the conductance modality is configured to determine a profile of a lumen based on detecting conductance values at multiple locations within the lumen, where the profile of the body lumen may include relative conductances and/or relative cross-sectional areas.

In a first embodiment, the location determined by the fiber optic modality may be confirmed using the conductance modality by accessing a stored (previously generated) lumen profile corresponding to the location determined by the fiber optic modality. When the stored lumen profile is the same or substantially the same as the lumen profile as determined by the conductance modality, the location determined by the fiber optic modality is confirmed.

In a second embodiment, when the location determined by the fiber optic modality is within the patient heart, the location may be confirmed using the conductance modality by continuously detecting the cross-sectional area of the lumen in which the distal tip of the medical instrument is disposed (e.g., a chamber of the heart) such that the rhythmic beating of the heart will result in a cross-sectional area that continuously changes in concert with the rhythmic beating. Thus, the confirmation logic 199 may determine that the continuously changing cross-sectional area of the lumen corresponds to an area within the heart, which corresponds to the location determined by the fiber optic modality and thus, confirms the location determined by the fiber optic modality is accurate.

As discussed above, in other embodiments, a location of the distal tip may be determined by selecting the location that was determined by a majority (or other threshold number or percentage) of the modalities. In another embodiment, each modality may be associated with a predetermined weight (e.g., provided by an expert, such as a medical professional) where the location of the distal tip is determined by a weighted sum of each location determined by the modalities such that the location having the greatest weight is determined to be the location of the distal tip. In some instances, the determined location must meet or exceed a confidence threshold prior to being provided to a user (e.g., rendered on the display screen 170 of the console 110 or other display mechanism). Alternatively, the weights of each location determined by the modalities by be provided.

Additional descriptions of the components of the systems 1100, 1102 may be found in in U.S. Pat. No. 10,172,538, the entire contents of which are incorporated by reference herein.

IV. Methodologies for Location Confirmation

As noted above, any of the systems, methods, and apparatuses illustrated in FIGS. 1A-12B may be used to determine a location of a distal tip of a medical instrument advancing within a patient vasculature. Further, any of the systems, methods, and apparatuses may be used in combination such that the location determined via a first modality may be used to confirm the location determined via a second modality. Additionally, three or more modalities may be utilized with each used to determine a location of the distal tip of the medical instrument within the patient vasculature such that the combination thereof may be utilized to determine a location.

For example, in one embodiment, a location of the distal tip may be determined by selecting the location that was determined by a majority (or other threshold number or percentage) of the modalities. In another embodiment, each modality may be associated with a predetermined weight (e.g., provided by an expert, such as a medical professional) where the location of the distal tip is determined by a weighted sum of each location determined by the modalities such that the location having the greatest weight is determined to be the location of the distal tip. In some instances, the determined location must meet or exceed a confidence threshold prior to being provided to a user (e.g., rendered on the display screen 170 of the console 110 or other display mechanism). Alternatively, the weights of each location determined by the modalities by be provided.

Although a plurality of systems, methods, and apparatuses providing various combinations of modalities are illustrated in and described with respect to FIGS. 1A-12B, the following discusses several additional parameters that may be utilized by the confirmation logic 199 to confirm the location of the distal tip of the medical instrument as determined by any of the modalities discussed above with respect to FIGS. 1A-12B.

As noted above, when a plurality of modalities are utilized to obtain data that is indicative of a location of a distal tip of a medical instrument, the data of one modality may be used to confirm a location determined by a different modality. Also disclosed, when a plurality of modalities are used to obtain such data, a weighting system may be utilized where a weight may be associated with the location determined by each modality such that a weighted set of locations may be provided to a clinician, the location having the greatest weight may be provided to the clinician, and/or locations having a weight above a predetermined confidence threshold may be provided to the clinician. As used herein, the weights associated with each modality and the corresponding locations may refer to a confidence in the particular modality in accurately determining the location of the distal tip of the medical instrument.

As an alternative to using a plurality of modalities, or in addition thereto, certain data may be utilized in a similar in confirming the accuracy of a location of the distal tip of medical instrument as determined by a particular modality or by a plurality of modalities. Discussed below are examples of such data where the data may be obtained through a modality discussed above but not correspond merely to the location of distal tip of medical instrument while other of the data are measurements obtained through various sensors that may be deployed by any of the systems described above (e.g., a pressure sensor, Doppler, or other imaging systems such as magnetic resonance imaging (MM)).

In some embodiments, as discussed above, the fiber optic modality may be utilized to determine a position of the distal tip of the medical instrument as well as the shape of the medical instrument (e.g., a current physical state of the medical instrument may be determined). The fiber optic modality may also be configured to enable determination of the path of the distal tip of a medical instrument. Such determinations may be made by analyses performed by the shape sensing logic 194. The location of the distal tip of the medical instrument, the shape of the medical instrument, and/or the path of the medical instrument within the patient vasculature may be utilized to confirm a location as determined by any of the modalities discussed above. For example, the TLS modality may obtain data that is indicative of the distal tip of the medical instrument being disposed within a particular chamber of the heart (e.g., based on tip fluctuation detection and/or a location of the magnetic assembly 904 detected by the TLS sensor 901. Any of the data determined by the fiber optic modality discussed above may be utilized to confirm the location of the distal tip as indicated by the TLS modality. As an illustrative example, the determined shape of the medical instrument may be used to confirm the location by the confirmation logic 199 through performance of operations including comparing shape of the medical instrument to a known anatomy of a patient vasculature and determining an expected location therefrom. When the location determined by the TLS modality is the same or substantially the same (within a predetermined distance range) as the expected location, the confirmation logic 199 determines the expected location confirms the location determined from the data of the TLS modality. As should be understood with respect to each example provided here, when the location determined by the TLS modality is not the same or even substantially the same (e.g., outside of a predetermined distance range) as the expected location, the confirmation logic 199 determines the expected location does not confirm the location determined by the TLS modality.

In other embodiments, an insertion length of the medical instrument may be utilized to confirm a location determined as a result of data obtained through any modality discussed above. For instance, a patient vasculature has a known anatomy such that a distance from an insertion point to a location within the patient vasculature may be determined. Thus, the confirmation logic 199 may utilize the insertion length (length of the medical instrument disposed within the patient vasculature) to determine an expected location based on correlation of the insertion length to the known vasculature anatomy. When the expected location corresponds to the location as determined by a modality discussed above, the confirmation logic 199 determines the expected location confirms the location determined from the data of the modality. In some embodiments, the shape sensing data (e.g., path of the medical instrument and/or shape of the medical instrument may be utilized to determine an expected location from the insertion length as path or shape inform the confirmation logic 199 as to the path to measure through the patient vasculature). In some embodiments, the insertion length may be determined through user input of a length as indicated by markings on an exterior of the medical instrument (or catheter) and/or through the fiber optic modality which may obtain information indicative of a temperature or pressure change on certain gratings.

Additionally, a temperature measured by the medical instrument may be indicative of certain locations within the patient vasculature. In some embodiments, the fiber optic modality may obtain temperature data at certain gratings (e.g., gratings located a distal portion of the medical instrument) and/or a medical instrument may include a dedicated temperature sensor at a distal end. The measured temperature may be compared to an expected temperature (e.g., stored or historical data) for the location determined by a modality discussed above. When the expected temperature is the same or substantially the same as the measured temperature, the confirmation logic 199 determines the measured temperature confirms the location determined from the data of the modality.

Further, vessel diameter measurements may be obtained, e.g., through the impedance/conductance modality discussed above. In some embodiments, a plurality of vessel diameter measurements may be obtained (e.g., at regular intervals) such that the measurements obtained over time may be compared to determine whether the diameter of the vessel in which the distal tip is disposed is increasing or decreasing as the medical instrument advances. The determination as to whether the vessel is increasing or decreasing in diameter may be referred to as the relative vessel diameter. Stated differently, the measurements over time enable the systems disclosed herein to determine whether the vessel diameter is getting bigger or smaller as the medical instrument advances. The measured relative vessel diameter may be compared to an expected relative vessel diameter (e.g., stored or historical data) for the location determined by a modality discussed above. When the expected relative vessel diameter is the same or substantially the same as the measured relative vessel diameter, the confirmation logic 199 determines the measured relative vessel diameter confirms the location determined from the data of the modality.

Similarly, in some embodiments, a single vessel diameter measurement ("absolute vessel diameter" measurement) may be utilized in confirming a location determined by a modality discussed above. For example, the measured absolute vessel diameter may be compared to an expected absolute vessel diameter (e.g., stored or historical data) for the location determined by a modality discussed above. When the expected absolute vessel diameter is the same or substantially the same as the measured absolute vessel diameter, the confirmation logic 199 determines the measured absolute vessel diameter confirms the location determined from the data of the modality.

Additionally, a pressure measured by the medical instrument may be indicative of certain locations within the patient vasculature. In some embodiments, the fiber optic modality may obtain pressure data at certain gratings (e.g., gratings located a distal portion of the medical instrument) and/or a medical instrument may include a dedicated pressure sensor at a distal end. The measured pressure may be compared to an expected pressure (e.g., stored or historical data) for the location determined by a modality discussed above. When the expected pressure is the same or substantially the same as the measured pressure, the confirmation logic 199 determines the measured pressure confirms the location determined from the data of the modality.

In some embodiments, flow character of an infusate, measured as a sensed temperature change based on flow of an infusate, may be indicative of certain locations within the patient vasculature. More specifically, relative to the temperature of the blood (or generally an internal body temperature), an infusate will be distinguishable based on its temperature (e.g., likely cooler than the temperature of the blood or internal body temperature) and thus detectable via temperature sensing via any of the methods discussed above. Depending on the location of the medical instrument, the flow of the infusate away from the distal tip will vary. For example, in a vein, blood flow will pull the infusate away from the distal tip resulting in a rapid temperature dispersion. In an artery, the infusate will flow back on the distal tip prolonging exposure to the cooler infusate over time. Going further, the rate at which detected temperature changes may provide insight into the flow of blood, diameter of vessel, rate of infusion, etc. Therefore, the measured flow character may be compared to an expected flow character (e.g., stored or historical data) for the location determined by a modality discussed above. When the expected flow character is the same or substantially the same as the measured flow character, the confirmation logic 199 determines the measured flow character confirms the location determined from the data of the modality.

Additionally, a direction of blood flow detected by the medical instrument may be indicative of certain locations within the patient vasculature. In some embodiments, ultrasound and Doppler may be utilized to obtain blood flow direct data. The blood flow direction may be compared to an expected blood flow direction (e.g., stored or historical data) for the location determined by a modality discussed above. When the expected blood flow direction is the same as the detected blood flow direction, the confirmation logic 199 determines the detected blood flow direction confirms the location determined from the data of the modality.

Finally, other imaging modalities may provide data that are indicative of certain locations within the patient vasculature. For instance, imaging modalities such as traditional ultrasound, intravascular ultrasound, fluoroscopy, and/or MRI may be used to obtain the data that are indicative of certain locations within the patient vasculature. The data may be live (e.g., obtain during by a clinician during a current procedure) and/or previously stored/recorded imaging data. The imaging modality data may be used to generate a graphic for display, e.g., on the display 170 (e.g., in a similar manner as shown in FIG. 10A where the imaging modality may replace the graphic generated from the TLS modality), such that a clinician may visually confirm the location as determined by any modality discussed above. In some embodiments, machine learning techniques may be utilized to determine whether the imaging data is predicted to correspond to a location determined by any modality discussed above. In such an embodiment, a machine learning model would be trained using historical imaging data where the trained machine learning model would be configured to provide a prediction as to a location within the patient vasculature that is captured in the imaging data. The trained machine learning model may also be configured to provide a score for a plurality of locations within the patient vasculature, where the score corresponds to a confidence. The location having the greatest score or indicated by the prediction provided by the machine learning algorithm may then be compared to the location indicated by any modality discussed above. When the location indicated by the imaging data is the same or substantially the same as the location determined by the modality discussed above, the confirmation logic 199 determines the imaging data confirms the location determined from the data of the modality.

Figure 13:
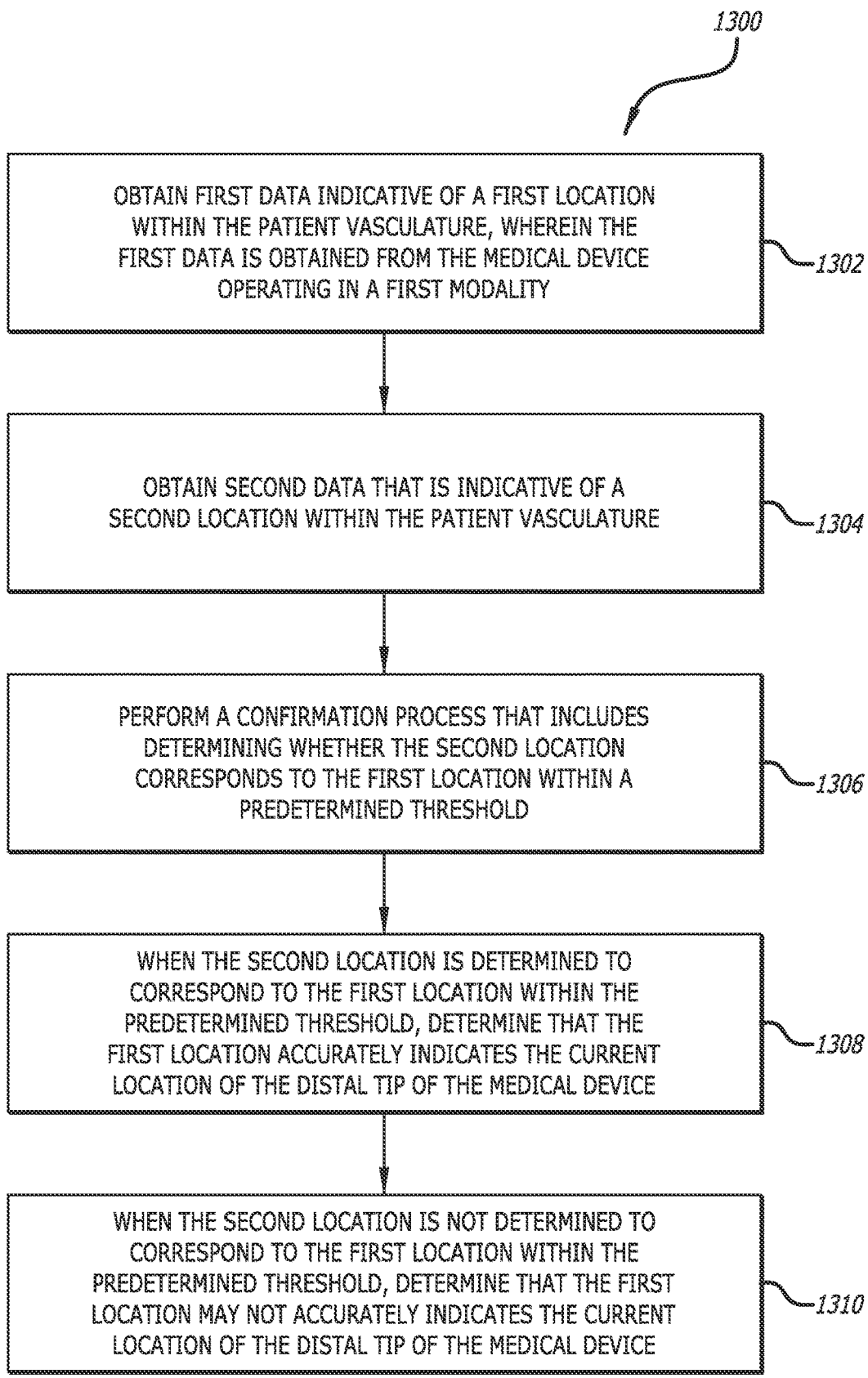
FIG. 13 is a flowchart of an illustrative methodology of detecting a current location of a distal tip of a medical device within a patient vasculature in accordance with some embodiments.

Referring now to FIG. 13, a flowchart of an illustrative methodology of detecting a current location of a distal tip of a medical device within a patient vasculature is shown in accordance with some embodiments. Each block illustrated in FIG. 13 represents an operation of the method 1300. It should be understood that not every operation illustrated in FIG. 13 is required. In fact, certain operations may be optional to complete aspects of the method 1300. The method 1300 begins with an operation of obtaining first data indicative of a first location within the patient vasculature, where the first data is obtained from the medical device operating in a first modality (block 1302). A second operation includes obtaining second data that is indicative of a second location within the patient vasculature (block 1304). Further, a third operation includes performing a confirmation process that includes determining whether the second location corresponds to the first location within a predetermined threshold (block 1306). Additional operations include when the second location is determined to correspond to the first location within the predetermined threshold, determining that the first location accurately indicates the current location of the distal tip of the medical device (block 1308) and when the second location is not determined to correspond to the first location within the predetermined threshold, determine that the first location may not accurately indicates the current location of the distal tip of the medical device (block 1310).

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A medical device system for detecting a current location of a distal tip of a medical device within a patient vasculature, the medical device system comprising:
   the medical device configured to operate in a first modality for obtaining first data being fiber optic data indicative of a first location within the patient vasculature; and
   a console including one or more processors and a non-transitory computer-readable medium having stored thereon logic, when executed by the one or more processors, causes operations including:
      obtaining second data being impedance fluctuation data through a second modality different than the first modality, and wherein the second data is indicative of a second location within the patient vasculature,
      performing a confirmation process that includes (i) retrieving stored impedance fluctuation data corresponding to the first location, wherein the stored impedance fluctuation data was previously obtained via the second modality, and (ii) comparing the stored impedance fluctuation data with the second data resulting in a determination as to whether the second location corresponds to the first location within a predetermined threshold, and
      when the second location is determined to correspond to the first location within the predetermined threshold, determining that the first location accurately indicates the current location of the distal tip of the medical device.

2. The medical device system of claim 1, wherein the first modality is a fiber optic modality, and wherein the medical device comprises an optical fiber having one or more core fibers, each of the one or more core fibers including a plurality of sensors distributed along a longitudinal length of a corresponding core fiber and each sensor of the plurality of sensors being configured to (i) reflect a light signal of a different spectral width based on received incident light, and (ii) change a characteristic of the reflected light signal based on strain experienced by the optical fiber.

3. The medical device system of claim 2, wherein the operations further include:
providing an incident light signal to the optical fiber,
receiving reflected light signals of different spectral widths of the incident light signal by one or more of the plurality of sensors, and
processing the reflected light signals associated with the one or more core fibers to determine the first data indicative of first location.

4. The medical device system of claim 1, wherein determining that the first location accurately indicates the current location of the distal tip of the medical device indicates the that the distal tip of the medical device is within a Superior Vena Cava (SVC) or a right atrium.

5. The medical device system of claim 4, wherein the second data represents fluctuations of the distal tip of the medical device.

6. The medical device system of claim 5, wherein the second data is obtained through the second modality, wherein the second modality is one of a magnetically-based tip location system (TLS) modality or an electrocardiogram (ECG) monitoring system modality, and wherein the second modality is different than the first modality.

7. The medical device system of claim 1, wherein the second data includes data obtained by one or more electrodes disposed on the medical device.

8. The medical device system of claim 1, wherein the medical device is one of an introducer wire, a guidewire, a stylet, the stylet within a needle, the needle, or a catheter.

9. A method for detecting a current location of a distal tip of a medical device within a patient vasculature, the method comprising:
obtaining first data being fiber optic data indicative of a first location within the patient vasculature, wherein the fiber optic data is obtained from the medical device operating in a first modality;
obtaining second data being impedance fluctuation data through a second modality different than the first modality, and wherein the second data is indicative of a second location within the patient vasculature,
performing a confirmation process that includes (i) retrieving stored impedance fluctuation data corresponding to the first location, wherein the stored impedance fluctuation data was previously obtained via the second modality, and (ii) comparing the stored impedance fluctuation data with the second data resulting in a determination as to whether the second location corresponds to the first location within a predetermined threshold, and
when the second location is determined to correspond to the first location within the predetermined threshold, determining that the first location accurately indicates the current location of the distal tip of the medical device.

10. The method of claim 9, wherein the first modality is a fiber optic modality, and wherein the medical device comprises an optical fiber having one or more core fibers, each of the one or more core fibers including a plurality of sensors distributed along a longitudinal length of a corresponding core fiber and each sensor of the plurality of sensors being configured to (i) reflect a light signal of a different spectral width based on received incident light, and (ii) change a characteristic of the reflected light signal based on strain experienced by the optical fiber.

11. The method of claim 10, further comprising:
providing an incident light signal to the optical fiber,
receiving reflected light signals of different spectral widths of the incident light signal by one or more of the plurality of sensors, and
processing the reflected light signals associated with the one or more core fibers to determine that the first data is indicative of the first location.

12. The method of claim 9, wherein determining that the first location accurately indicates the current location of the distal tip of the medical device indicates that the distal tip of the medical device is within a Superior Vena Cava (SVC) or a right atrium.

13. The method of claim 12, wherein the second data represents fluctuations of the distal tip of the medical device.

14. The method of claim 13, wherein the second data is obtained through the second modality, wherein the second modality is one of a magnetically-based tip location system (TLS) modality or an electrocardiogram (ECG) monitoring system modality, and wherein the second modality is different than the first modality.

15. The method of claim 9, wherein the second data includes data obtained by one or more electrodes disposed on the medical device.

16. The method of claim 9, wherein the medical device is one of an introducer wire, a guidewire, a stylet, the stylet within a needle, the needle, or a catheter.

17. A non-transitory computer-readable medium having stored thereon logic that, when executed by one or more processors, causes operations including:
obtaining first data being fiber optic data indicative of a first location within a patient vasculature, wherein the fiber optic data is obtained from a medical device operating in a first modality;
obtaining second data being impedance fluctuation data through a second modality different than the first modality, and wherein the second data is indicative of a second location within the patient vasculature,
performing a confirmation process that includes (i) retrieving stored impedance fluctuation data corresponding to the first location, wherein the stored impedance fluctuation data was previously obtained via the second modality, and (ii) comparing the stored impedance fluctuation data with the second data resulting in a determination as to whether the second location corresponds to the first location within a predetermined threshold, and
when the second location is determined to correspond to the first location within the predetermined threshold, determining that the first location accurately indicates a current location of a distal tip of the medical device.

18. The non-transitory computer-readable medium of claim 17, wherein the first modality is a fiber optic modality, and wherein the medical device comprises an optical fiber having one or more core fibers, each of the one or more core fibers including a plurality of sensors distributed along a longitudinal length of a corresponding core fiber and each sensor of the plurality of sensors being configured to (i) reflect a light signal of a different spectral width based on received incident light, and (ii) change a characteristic of the reflected light signal based on strain experienced by the optical fiber.

19. The non-transitory computer-readable medium of claim 18, wherein the operations further include:
   providing an incident light signal to the optical fiber,
   receiving reflected light signals of different spectral widths of the incident light by one or more of the plurality of sensors, and
   processing the reflected light signals associated with the one or more core fibers to determine the first data indicative of the first location.

20. The non-transitory computer-readable medium of claim 17, wherein determining that the first location accurately indicates the current location of the distal tip of the medical device indicates that the distal tip of the medical device is within a Superior Vena Cava (SVC) or a right atrium.

21. The non-transitory computer-readable medium of claim 20, wherein the second data represents fluctuations of the distal tip of the medical device.

22. The non-transitory computer-readable medium of claim 21, wherein the second data is obtained through the second modality, wherein the second modality is one of a magnetically-based tip location system (TLS) modality or an electrocardiogram (ECG) monitoring system modality, and wherein the second modality is different than the first modality.

23. The non-transitory computer-readable medium of claim 17, wherein the second data includes data obtained by one or more electrodes disposed on the medical device.

24. The non-transitory computer-readable medium of claim 17, wherein the medical device is one of an introducer wire, a guidewire, a stylet, the stylet within a needle, the needle, or a catheter.

* * * * *